US012569519B2

(12) United States Patent
Polansky

(10) Patent No.: US 12,569,519 B2
(45) Date of Patent: Mar. 10, 2026

(54) THERAPEUTIC METHODS AND COMPOSITIONS UTILIZING STROMAL VASCULAR FRACTION DERIVED FROM ADIPOSE TISSUE

(71) Applicant: Advanced Therapeutic Lab, Inc., New York, NY (US)

(72) Inventor: Glenn Polansky, New York, NY (US)

(73) Assignee: Advanced Therapeutic Lab, Inc., New York, NY (US)

( * ) Notice: Subject to any disclaimer, the term of this patent is extended or adjusted under 35 U.S.C. 154(b) by 0 days.

(21) Appl. No.: 17/525,312

(22) Filed: Nov. 12, 2021

(65) Prior Publication Data

US 2022/0211769 A1    Jul. 7, 2022

Related U.S. Application Data

(60) Provisional application No. 63/113,481, filed on Nov. 13, 2020.

(51) Int. Cl.

| | |
|---|---|
| *A61K 35/35* | (2015.01) |
| *A61K 9/00* | (2006.01) |
| *A61P 3/10* | (2006.01) |
| *A61P 9/00* | (2006.01) |
| *A61P 11/00* | (2006.01) |
| *A61P 21/00* | (2006.01) |
| *A61P 25/02* | (2006.01) |

(52) U.S. Cl.
CPC ............ *A61K 35/35* (2013.01); *A61K 9/0019* (2013.01)

(58) Field of Classification Search
CPC ....... A61K 35/35; A61K 9/0019; A61P 11/00; A61P 11/06; A61P 31/14
See application file for complete search history.

(56) References Cited

U.S. PATENT DOCUMENTS

| | | |
|---|---|---|
| 7,875,273 B2 | 1/2011 | Messina et al. |
| 8,361,459 B2 | 1/2013 | Messina et al. |
| 8,440,440 B2 | 5/2013 | Victor |
| 9,040,035 B2 | 5/2015 | Herzberg et al. |
| 9,629,879 B2 | 4/2017 | Corteling et al. |
| 9,844,514 B2 | 12/2017 | Williams et al. |
| 10,011,820 B2 | 7/2018 | LeBlanc et al. |
| 10,457,912 B2 | 10/2019 | Simpson et al. |
| 10,913,931 B1 | 2/2021 | Polansky |
| 11,066,647 B2 | 7/2021 | Chazenbalk |
| 11,236,324 B2 | 2/2022 | Bright et al. |
| 2010/0008992 A1 | 1/2010 | Ichim |
| 2012/0070420 A1 | 3/2012 | Mishra |
| 2014/0255356 A1 | 9/2014 | Victor |
| 2015/0147409 A1 | 5/2015 | March et al. |
| 2015/0159151 A1 | 6/2015 | Bright et al. |
| 2016/0030486 A1 | 2/2016 | Cimino et al. |
| 2021/0106627 A1 | 4/2021 | Cimino et al. |
| 2021/0147788 A1 | 5/2021 | Rizwani |
| 2021/0147806 A1 | 5/2021 | Polansky |
| 2021/0228644 A1 | 7/2021 | Reidling et al. |
| 2022/0096558 A1 | 3/2022 | Woods et al. |

FOREIGN PATENT DOCUMENTS

| | | |
|---|---|---|
| EP | 2379087 B1 | 8/2014 |
| JP | 2009161507 A | 7/2009 |
| WO | WO-2008116157 A2 | 9/2008 |
| WO | WO-2010060031 A1 | 5/2010 |
| WO | WO-2010071864 A1 | 6/2010 |
| WO | WO-2013030761 A1 | 3/2013 |
| WO | WO-2013076726 A1 | 5/2013 |
| WO | WO-2014000029 A1 | 1/2014 |
| WO | WO-2014015229 A1 | 1/2014 |
| WO | WO-2014036094 A1 | 3/2014 |
| WO | WO-2014138383 A1 | 9/2014 |
| WO | WO-2014152282 A1 | 9/2014 |
| WO | WO-2014169885 A1 | 10/2014 |
| WO | WO-2014179834 A1 | 11/2014 |

OTHER PUBLICATIONS

Comella et al (Safety Analysis of Autologous Stem Cell Therapy in a Variety of Degenerative Diseases and Injuries Using the Stromal Vascular Fraction. J Clin Med Res, vol. 11, 2017; cited in IDS dated Nov. 2, 2022) (Year: 2017).*
Cheng et al (Mesenchymal Stem Cell Administration in Patients with Chronic Obstructive Pulmonary Disease: State of the Science. Stem Cells Int, vol. 2017) (Year: 2017).*
Bora et al (Adipose tissue-derived stromal vascular fraction in regenerative medicine: a brief review on biology and translation. Stem Cell Research & Therapy, vol. 8, 2017) (Year: 2017).*
Karina et al (Safety of Technique and Procedure of Stromal Vascular Fraction Therapy: From Liposuction to Cell Administration. Scientifica, vol. 2020; cited in IDS dated Nov. 2, 2022) (Year: 2020).*
Oberbauer et al (Enzymatic and non-enzymatic isolation systems for adipose tissue-derived cells: current state of the art. Cell Regeneration, vol. 4, 2015) (Year: 2015).*
QSonica Sonicator catalog (copyright 2018). (Year: 2018).*
Comella et al (Autologous Stromal Vascular Fraction in the Intravenous Treatment of End-Stage Chronic Obstructive Pulmonary Disease: A Phase I Trial of Safety and Tolerability. J Clin Med Res., vol. 9, 2017). (Year: 2017).*
Astori et al ("In vitro" and multicolor phenotypic characterization of cell subpopulations identified in fresh human adipose tissue stromal vascular fraction and in the derived mesenchymal stem cells. Journal of translational medicine, vol. 5, 2007). (Year: 2007).*
Weiss et al (Proc Am Thorac Soc vol. 8. pp 223-272, 2011 (Year: 2011).*
Averyanov et al, Stem Cells Transl Med. 2020;9:6-16. (Year: 2020).*

(Continued)

*Primary Examiner* — Emily A Cordas
*Assistant Examiner* — Matasha Dhar
(74) *Attorney, Agent, or Firm* — Morgan, Lewis & Bockius LLP

(57) ABSTRACT

The invention provides methods and compositions utilizing stromal vascular fraction derived from adipose tissue to treat various medical disorders, such as pulmonary disorders, neurodegenerative disorders, brain injury, psychiatric disorders, metabolic disorders, and pain.

34 Claims, No Drawings

(56) References Cited

OTHER PUBLICATIONS

HBCOVID03, Jun. 15, 2020 (Year: 2020).*

Comella, K. et al., "Safety Analysis of Autologous Stem Cell Therapy in a Variety of Degenerative Diseases and Injuries Using the Stromal Vascular Fraction," *J.Clin. Med. Res.*, vol. 9, No. 11, pp. 935-942, (2017).

Eiro, N. et al., "The Coronavirus Pandemic (SARS-CoV-2): New Problems Demand New Solutions, the Alternative of Mesenchymal (Stem) Stromal Cells," *Frontiers in Cell and Developmental Biology*, vol. 8, article 645, (Jul. 2020).

Erickson, G.R. et al., "Chondrogenic potential of adipose tissue-derived stromal cells in vitro and in vivo," *Biochem. Biophys. Res. Commun.*, p. 763 (2002). (Abstract only).

Hicok, K.C. et al., "Human adipose-derived adult stem cells produce osteoid in vivo," *Tissue Eng.* p. 371 (2004). (Abstract only).

International Search Report and Written Opinion for International Patent Application No. PCT/US2021/059155, dated Feb. 7, 2022, 9 pages.

Karina, K. et al., "Safety of Technique and Procedure of Stromal Vascular Fraction Therapy: From Liposuction to Cell Administration," *Scientifica*, vol. 2020, (2020) article 2863624.

Koh, Y.J. et al., "Stromal Vascular Fraction From Adipose Tissue Forms Profound Vascular Network Through the Dynamic Reassembly of Blood Endothelial Cells," *Arterioscler. Thromb. Vasc. Biol.*, vol. 31, pp. 1141-1150 (2011).

Lander, E.B. et al., "Safety of stromal vascular fraction cells applications in chronic pain," *Techniques in Regional Anesthesia and Pain Management*, vol. 19, pp. 10-13, (2015).

Zuk, P.A. et al., "Human Adipose Tissue is a Source of Multipotent Stem Cells," *Molec. Biol. of the Cell*, vol. 13, pp. 4279-4295 (2002).

Zuk, P.A. et al., "Multilineage cells from human adipose tissue: implications for cell-based therapies," *Tissue Eng.*, p. 211 (2001). (Abstract only).

Amirkhani, M. A., et al., "A rapid sonication based method for preparation of stromal vascular fraction and mesenchymal stem cells from fat tissue," *BioImpacts*, 2016, vol. 6, No. 2, p. 99-104.

Clinicaltrials.gov posting dated Jan. 9, 2018 for NCT01849159.

Clinicaltrials.gov posting dated Jan. 9, 2018 for NCT02594839.

Clinicaltrials.gov posting dated Mar. 1, 2018 for NCT01440192.

Rogers, C. J. et al. "Rationale for the clinical use of adipose-derived mesenchymal stem cells for COVID-19 patients," *J. Transl. Med.*, vol. 18, Article 203 (2020).

Sanchez-Guijo, F. et al., "Adipose-derived mesenchymal stromal cells for the treatment of patients with severe SARS-CoV-2 pneumonia requiring mechanical ventilation. A proof of concept study," *EClinicalMedicine*, vol. 25, Article 100454 (2020).

* cited by examiner

THERAPEUTIC METHODS AND COMPOSITIONS UTILIZING STROMAL VASCULAR FRACTION DERIVED FROM ADIPOSE TISSUE

CROSS-REFERENCE TO RELATED APPLICATION

This application claims the benefit of and priority to U.S. Provisional Patent Application Ser. No. 63/113,481, filed Nov. 13, 2020, the contents of which are hereby incorporated by reference in their entirety.

FIELD OF THE INVENTION

The invention provides methods and compositions utilizing stromal vascular fraction derived from adipose tissue to treat various medical disorders, such as pulmonary disorders, neurodegenerative disorders, brain injury, psychiatric disorders, metabolic disorders, and pain.

BACKGROUND

Adipose tissues can be used as source of multipotent stem cells. See Zuk et al. (2002) *Mol Biol Cell.* 13: 4279-4295. Adipose tissue can be processed to generate stromal vascular fraction, which contains multiple types of cells, including, for example, preadipocytes, mesenchymal stem cells (MSC), endothelial progenitor cells, blood endothelial cells, fibroblasts, pericytes, T regulatory cells, and macrophages. See, for example, Koh et al. (2011) *Arterioscler Thromb Vasc Biol.* 31(5): 1141-50. Mesenchymal stem cells (MSC) can be differentiated into a variety of cell lineages including adipogenic, chondrogenic, myogenic, and osteogenic lineages. See, for example, Rodriguez et al. (2012) *International Archives of Medicine* 5: 1-9; Zuk et al. (2001) *Tissue Eng.* 7: 211-228; Hicok et al. (2004) *Tissue Eng.* 10: 371-380; and Erickson et al. (2002) *Biochem Biophys Res Commun.* 290: 763-769. The stromal vascular fraction can be administered to patients to provide medical benefits.

Patients suffering from medical disorders such as pulmonary disorders, neurodegenerative disorders, brain injury, psychiatric disorders, metabolic disorders, and pain could benefit from a minimally invasive therapy that provides relief of symptoms or even cure of the disorder. Pulmonary disorders such as chronic obstructive pulmonary disease, asthma, bronchitis, emphysema, and acute respiratory distress syndrome affect a substantial number of patients for which currently available treatments are either insufficient or cause undesirable adverse side effects. Similarly, there is an unmet need for more effective and/or safer therapies for treating neurodegenerative disorders, brain injury, and psychiatric disorders. Pain and metabolic disorders such as diabetes mellitus continue to adversely affect the quality of life for many patients, particularly elderly patients, and new therapeutic methods for treating these diseases are needed.

Accordingly, a need exists for improved treatments for pulmonary disorders, neurodegenerative disorders, brain injury, psychiatric disorders, metabolic disorders, pain and other disorders. The present invention addresses this need and provides other related advantages.

SUMMARY

The invention provides methods and compositions utilizing stromal vascular fraction derived from adipose tissue to treat various medical disorders, such as pulmonary disorders, neurodegenerative disorders, brain injury, psychiatric disorders, metabolic disorders, and pain. The methods provide particular treatment protocols useful for administering a stromal vascular fraction containing a large number of cells to patients. The treatment protocols describe intravenous administration procedures for administering an injectable pharmaceutical composition containing saline and stromal vascular fraction to patients in need of therapy, which often specify administering an injectable pharmaceutical composition containing saline and stromal vascular fraction to the patient on multiple days separated by a particular amount of time. Additional features of the methods, such as the number of cells administered to the patient, rate at which the injectable pharmaceutical composition is intravenously administered to the patient, characteristics of cells from the vascular stromal fraction being administered to the patient, and optional intravenous administration of saline to the patient prior to administration of an injectable pharmaceutical composition comprising saline and stromal vascular fraction, are described. Intravenous administration of saline to the patient prior to starting intravenous administration of an injectable pharmaceutical composition containing saline and stromal vascular fraction on a given day improves systemic distribution of stem cells in patient's circulatory system from the stromal vascular fraction, which provides benefits when treating disorders such as neurodegenerative disorders, brain injury, psychiatric disorders, metabolic disorders, and pain. Without prior intravenous administration of saline, stem cells from the intravenously administered stromal vascular fraction tend to congregate in the patient's lungs. Preferably, the stromal vascular fraction is obtained by processing adipose tissue obtained from the patient, and the adipose tissue is processed using a sonication procedure that does not use an enzyme or sonication probe. Absence of enzyme and a sonication probe reduces the risk of contaminating the stromal vascular fraction; purity of the stromal vascular fraction is particularly important when the stromal vascular fraction is to be administered to the patient by intravenous injection. These and other features of the methods and compositions are described in more detail below.

One aspect of the invention provides a method of treating a pulmonary disorder, comprising intravenously administering to a patient in need thereof a stromal vascular fraction according to the following dosing schedule, in order to treat the pulmonary disorder:

a. on the first day, intravenously administer to the patient in need thereof over a duration of about 35 minutes a first injectable pharmaceutical composition containing saline and an aliquot of stromal vascular fraction containing from about 0.7 billion to about 3 billion cells;

b. on the day after the first day, intravenously administer to the patient in need thereof over a duration of about 35 minutes a second injectable pharmaceutical composition containing saline and an aliquot of stromal vascular fraction containing from about 0.3 billion to about 2 billion cells;

c. on the second day after the first day, intravenously administer to the patient in need thereof over a duration of about 35 minutes a third injectable pharmaceutical composition containing saline and an aliquot of stromal vascular fraction containing from about 0.3 billion to about 2 billion cells; and d. on the third day after the first day, intravenously administer to the patient in need thereof over a duration of about 35 minutes a fourth injectable pharmaceutical composition containing saline and an aliquot of stromal vascular fraction containing from about 0.3 billion to about 2 billion cells;

wherein the stromal vascular fraction is derived from adipose tissue through sonication of lipoaspirate and without the use of an enzyme or sonication probe.

Another aspect of the invention provides a method of treating a neurodegenerative disorder, comprising intravenously administering to a patient in need thereof a stromal vascular fraction according to the following dosing schedule, in order to treat the neurodegenerative disorder:

a. on the first day:
   i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
   ii. intravenously administer to the patient in need thereof over a duration of about 30 minutes a second injectable pharmaceutical composition containing saline and an aliquot of stromal vascular fraction containing from about 0.2 billion to about 4 billion cells;

b. on the day that is about 30 days after the first day:
   i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
   ii. intravenously administer to the patient in need thereof over a duration of about 30 minutes a second injectable pharmaceutical composition containing saline and an aliquot of stromal vascular fraction containing from about 0.2 billion to about 4 billion cells;

c. on the day that is about 60 days after the first day:
   i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
   ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

Another aspect of the invention provides a method of treating a disorder selected from the group consisting of a brain injury and a psychiatric disorder, comprising intravenously administering to a patient in need thereof a stromal vascular fraction according to the following dosing schedule, in order to treat the disorder:

a. on the first day:
   i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

b. on the day that is about 30 days after the first day:
   i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
   ii. intravenously administer to the patient in need thereof over a duration of about 30 minutes a second injectable pharmaceutical composition containing saline and an aliquot of stromal vascular fraction containing from about 0.2 billion to about 4 billion cells; and c. on the day that is about 60 days after the first day:
   i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
   ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

Another aspect of the invention provides a method of treating a metabolic disorder, comprising intravenously administering to a patient in need thereof a stromal vascular fraction according to the following dosing schedule, in order to treat the metabolic disorder:

a. on the first day:
   i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
   ii. intravenously administer to the patient in need thereof over a duration of about 30 minutes a second injectable pharmaceutical composition containing saline and an aliquot of stromal vascular fraction containing from about 0.2 billion to about 4 billion cells;

b. on the day that is about 14 days after the first day:
   i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
   ii. intravenously administer to the patient in need thereof over a duration of about 30 minutes a second injectable pharmaceutical composition containing saline and an aliquot of stromal vascular fraction containing from about 0.2 billion to about 4 billion cells;

c. on the day that is about 35 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

d. on the day that is about 65 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells; and e. on the day that is about 95 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

Another aspect of the invention provides a method of treating pain, comprising intravenously administering to a patient in need thereof a stromal vascular fraction according to the following dosing schedule, in order to treat the pain:

a. on the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

b. on the day that is about 90 days after the first day:

i. intravenously administer to the patient in need thereof over a duration of about 45 minutes an a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells; and c. on the day that is about 210 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

Another aspect of the invention provides a method of treating pain, comprising intravenously administering to a patient in need thereof a stromal vascular fraction according to the following dosing schedule, in order to treat the pain:

a. on the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline an aliquot of stromal vascular fraction containing from about 0.2 billion to about 4 billion cells;

b. on the day that is about 30 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

c. on the day that is about 60 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

d. on the day that is about 90 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells; and e. on the day that is about 120 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

Another aspect of the invention provides a method for the treatment or prophylaxis of a coronavirus infection in a patient, comprising intravenously administering to said patient in need thereof a stromal vascular fraction according to the following dosing schedule:

a. on the first day, intravenously administer to the patient in need thereof over a duration of about 35 minutes a first injectable pharmaceutical composition containing saline and an aliquot of stromal vascular fraction containing from about 0.7 billion to about 3 billion cells;

b. on the day after the first day, intravenously administer to the patient in need thereof over a duration of about 35 minutes a second injectable pharmaceutical composition containing saline and an aliquot of stromal vascular fraction containing from about 0.3 billion to about 2 billion cells;

c. on the second day after the first day, intravenously administer to the patient in need thereof over a duration of about 35 minutes a third injectable pharmaceutical composition containing saline and an aliquot of stromal vascular fraction containing from about 0.3 billion to about 2 billion cells; and d. on the third day after the first day, intravenously administer to the patient in need thereof over a duration of about 35 minutes a fourth injectable pharmaceutical composition containing saline and an aliquot of stromal vascular fraction containing from about 0.3 billion to about 2 billion cells;

wherein the stromal vascular fraction is derived from adipose tissue through sonication of lipoaspirate and without the use of an enzyme or sonication probe.

Stromal vascular fraction used in the method is preferably obtained by processing adipose tissue obtained from the patient, wherein the adipose tissue is processed using a sonication procedure that does not use an enzyme or sonication probe. The population of cells in the stromal vascular fraction preferably has a cell viability of at least 90%, and more preferably at least 95%. One benefit of the methods described herein in that a large population of cells in a stromal vascular fraction can be obtained from the patient's adipose tissue and administered to the patient on the same day. For example, adipose tissue can be obtained from the patient, then processed to provide stromal vascular fraction, and then an aliquot of the stromal vascular fraction can be administered to the patient all the same day, sometimes even within 5, 6, 7, or 8 hours of starting the procedure for isolating adipose tissue from the patient.

Pharmaceutical compositions and medical kits for use in the therapeutic methods are provided. The pharmaceutical compositions are preferably injectable pharmaceutical compositions suitable for intravenous administration to the patient.

DETAILED DESCRIPTION

The invention provides methods and compositions utilizing stromal vascular fraction derived from adipose tissue to treat various medical disorders, such as pulmonary disorders, neurodegenerative disorders, brain injury, psychiatric disorders, metabolic disorders, and pain. The methods provide particular treatment protocols useful for administering a stromal vascular fraction containing a large number of cells to patients. The treatment protocols describe intravenous administration procedures for administering an injectable pharmaceutical composition containing saline and stromal vascular fraction to patients in need of therapy, which often specify administering an injectable pharmaceutical composition containing saline and stromal vascular fraction to the patient on multiple days separated by a particular amount of time. Additional features of the methods, such as the number of cells administered to the patient, rate at which the injectable pharmaceutical composition is intravenously administered to the patient, characteristics of cells from the vascular stromal fraction being administered to the patient, and optional intravenous administration of saline to the patient prior to administration of an injectable pharmaceutical composition comprising saline and stromal vascular fraction, are described. Intravenous administration of saline to the patient prior to starting intravenous administration of an injectable pharmaceutical composition containing saline and stromal vascular fraction on a given day improves systemic distribution of stem cells in patient's circulatory system from the stromal vascular fraction, which provides benefits when treating disorders such as neurodegenerative disorders, brain injury, psychiatric disorders, metabolic disorders, and pain. Without prior intravenous administration of saline, stem cells from the intravenously administered stromal vascular fraction tend to congregate in the patient's lungs. Preferably, the stromal vascular fraction is obtained by processing adipose tissue obtained from the patient, and the adipose tissue is processed using a sonication procedure that does not use an enzyme or sonication probe. Absence of enzyme and a sonication probe reduces the risk of contaminating the stromal vascular fraction; purity of the stromal vascular fraction is particularly important when the stromal vascular fraction is to be administered to the patient by intravenous injection. These and other features of the methods and compositions are described in more detail below. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims.

The terms "a" and "an" as used herein mean "one or more" and include the plural unless the context is inappropriate.

As used herein, the term "about" refers to within ±10% of the stated value. The invention encompasses embodiments where the value is within ±9%, ±8%, ±7%, ±6%, ±5%, ±4%, ±3%, ±2%, or ±1% of the stated value.

As used herein, the terms "subject" and "patient" are used interchangeably and refer to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a therapeutic agent to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "saline" refers to an aqueous solution comprising water and sodium chloride. In certain embodiments, the saline may be an aqueous solution containing 0.90% w/v NaCl. In certain embodiments, the saline may be an aqueous solution containing NaCl in an amount sufficient to provide an osmolality of 308 mOsm/L. Saline is desirably used for intravenous administration to patients, and saline may be used as a carrier in a pharmaceutical composition for intravenous administration to patient, such as a pharmaceutical composition containing stem cells. The saline may be isotonic, to facilitate tolerance when intravenously administered to a patient.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified.

I. Therapeutic Methods Using Stromal Vascular Fraction

The invention provides methods of treating various disorders by administering to the patient a stromal vascular fraction. Exemplary disorders for treatment include, for example, a pulmonary disorder, a neurodegenerative disorder, brain injury, psychiatric disorder, metabolic disorder, and pain. These are described in more detail below.

A. Methods for Treating a Pulmonary Disorder

One aspect of the invention provides methods for treating a pulmonary disorder. This is described in more detail below.

First Method

One aspect of the invention provides a method of treating a pulmonary disorder, comprising intravenously administering to a patient in need thereof a stromal vascular fraction according to the following dosing schedule, in order to treat the pulmonary disorder:

a. on the first day, intravenously administer to the patient in need thereof over a duration of about 35 minutes a first injectable pharmaceutical composition containing saline and an aliquot of stromal vascular fraction containing from about 0.7 billion to about 3 billion cells;

b. on the day after the first day, intravenously administer to the patient in need thereof over a duration of about 35 minutes a second injectable pharmaceutical composition containing saline and an aliquot of stromal vascular fraction containing from about 0.3 billion to about 2 billion cells;

c. on the second day after the first day, intravenously administer to the patient in need thereof over a duration of about 35 minutes a third injectable pharmaceutical composition containing saline and an aliquot of stromal vascular fraction containing from about 0.3 billion to about 2 billion cells; and d. on the third day after the first day, intravenously administer to the patient in need thereof over a duration of about 35 minutes a fourth injectable pharmaceutical composition containing saline and an aliquot of stromal vascular fraction containing from about 0.3 billion to about 2 billion cells;

wherein the stromal vascular fraction is derived from adipose tissue through sonication of lipoaspirate and without the use of an enzyme or sonication probe.

Second Method

Another aspect of the invention provides a method of treating a pulmonary disorder, comprising intravenously administering to a patient in need thereof a stromal vascular fraction according to the following dosing schedule, in order to treat the pulmonary disorder:

a. intravenously administer to the patient in need thereof a first injectable pharmaceutical composition containing saline and an aliquot of stromal vascular fraction; thereafter b. intravenously administer to the patient in need thereof a second injectable pharmaceutical composition containing saline and an aliquot of stromal vascular fraction; thereafter c. intravenously administer to the patient in need thereof a third injectable pharmaceutical composition containing saline and an aliquot of stromal vascular fraction; and thereafter d. intravenously administer to the patient in need thereof a fourth injectable pharmaceutical composition containing saline and an aliquot of stromal vascular fraction.

In certain embodiments, step (b) is performed at least one day after step (a). In certain embodiments, step (b) is performed one day after step (a). In certain embodiments, step (c) is performed at least one day after step (b). In certain embodiments, step (c) is performed one day after step (b). In certain embodiments, step (d) is performed at least one day after step (c). In certain embodiments, step (d) is performed one day after step (c).

In a more specific embodiment, the invention provides a method of treating a pulmonary disorder, comprising intravenously administering to a patient in need thereof a stromal vascular fraction according to the following dosing schedule, in order to treat the pulmonary disorder:

a. on the first day, intravenously administer to the patient in need thereof a first injectable pharmaceutical composition containing saline and an aliquot of stromal vascular fraction;

b. on the day after the first day, intravenously administer to the patient in need thereof a second injectable pharmaceutical composition containing saline and an aliquot of stromal vascular fraction;

c. on the second day after the first day, intravenously administer to the patient in need thereof a third injectable pharmaceutical composition containing saline and an aliquot of stromal vascular fraction; and d. on the third day after the first day, intravenously administer to the patient in need thereof a fourth injectable pharmaceutical composition containing saline and an aliquot of stromal vascular fraction.

In certain embodiments, the stromal vascular fraction is derived from adipose tissue through sonication of lipoaspirate and without the use of an enzyme or sonication probe.

In certain embodiments, in step (a), the injectable pharmaceutical composition is intravenously administered in less than about 60 minutes, 45 minutes, 35 minutes, 25 minutes, 15 minutes, or 10 minutes. In certain embodiments, in step (a), the injectable pharmaceutical composition is intravenously administered over from about 15 minutes to about 60 minutes, or from about 25 minutes to about 45 minutes. In certain embodiments, in step (a), the injectable pharmaceutical composition is intravenously administered over about 35 minutes.

In certain embodiments, in step (b), the injectable pharmaceutical composition is intravenously administered in less than about 60 minutes, 45 minutes, 35 minutes, 25 minutes, 15 minutes, or 10 minutes. In certain embodiments, in step (b), the injectable pharmaceutical composition is intravenously administered over from about 15 minutes to about 60 minutes, or from about 25 minutes to about 45 minutes. In certain embodiments, in step (b), the injectable pharmaceutical composition is intravenously administered over about 35 minutes.

In certain embodiments, in step (c), the injectable pharmaceutical composition is intravenously administered in less than about 60 minutes, 45 minutes, 35 minutes, 25 minutes, 15 minutes, or 10 minutes. In certain embodiments, in step (c), the injectable pharmaceutical composition is intravenously administered over from about 15 minutes to about 60 minutes, or from about 25 minutes to about 45 minutes. In certain embodiments, in step (c), the injectable pharmaceutical composition is intravenously administered over about 35 minutes.

In certain embodiments, in step (d), the injectable pharmaceutical composition is intravenously administered in less than about 60 minutes, 45 minutes, 35 minutes, 25 minutes, 15 minutes, or 10 minutes. In certain embodiments, in step (d), the injectable pharmaceutical composition is intravenously administered over from about 15 minutes to about 60 minutes, or from about 25 minutes to about 45 minutes. In certain embodiments, in step (d), the injectable pharmaceutical composition is intravenously administered over about 35 minutes.

Additional Exemplary Features of the First and Second Methods for Treating a Pulmonary Disorder Additional exemplary features that may characterize the First and Second Methods for treating a pulmonary disorder described herein are provided below and include, for example, characteristics of the injectable pharmaceutical compositions, pulmonary disorders to be treated, and results produced by the methods. A more thorough description of such features is provided below. The invention embraces all permutations and combinations of these features.

Injectable Pharmaceutical Compositions

The methods may be further characterized according to characteristics of the injectable pharmaceutical compositions, such as the number of cells in the stromal vascular fraction in the injectable pharmaceutical compositions, the volume of saline in the compositions, and the total volume of the injectable pharmaceutical compositions.

For example, in certain embodiments, the first injectable pharmaceutical composition contains saline and an aliquot of stromal vascular fraction containing from about 0.9 billion to about 1.5 billion cells. In certain embodiments, the second injectable pharmaceutical composition contains saline and an aliquot of stromal vascular fraction containing from about 0.4 billion to about 1 billion cells. In certain embodiments, the third injectable pharmaceutical composition contains saline and an aliquot of stromal vascular fraction containing from about 0.4 billion to about 1 billion cells. In certain embodiments, the fourth injectable pharmaceutical composition contains saline and an aliquot of stromal vascular fraction containing from about 0.4 billion to about 1 billion cells.

In certain embodiments, the first injectable pharmaceutical composition contains from about 240 mL to about 290 mL saline. In certain embodiments, the second injectable pharmaceutical composition contains from about 240 mL to about 290 mL saline. In certain embodiments, the third injectable pharmaceutical composition contains from about 240 mL to about 290 mL saline. In certain embodiments, the fourth injectable pharmaceutical composition contains from about 240 mL to about 290 mL saline.

In certain embodiments, the first injectable pharmaceutical composition has a volume of from about 330 mL to about 350 mL. In certain embodiments, the second injectable pharmaceutical composition has a volume of from about 290 mL to about 310 mL. In certain embodiments, the third injectable pharmaceutical composition has a volume of from about 290 mL to about 310 mL. In certain embodiments, the fourth injectable pharmaceutical composition has a volume of from about 290 mL to about 310 mL.

Additional Method Steps

The methods may be further characterized according to additional steps that the method further comprises. For example, in certain embodiments, the method further comprises the step of: prior to intravenously administering the first injectable pharmaceutical composition to the patient on the first day, adipose tissue is obtained from the patient and processed to provide stromal vascular fraction used in the first injectable pharmaceutical composition.

In certain embodiments, the method is characterized by the feature that saline is not intravenously administered to the patient immediately prior to intravenously administering the first injectable pharmaceutical composition. Intravenously administering the first injectable pharmaceutical composition to the patient at fast rate without immediately prior intravenous administration of saline results in a higher concentration of stem cells from the stromal vascular fraction in the patient's lungs, which provides benefits when treating a pulmonary disorder.

Pulmonary Disorders to be Treated

The methods may be further characterized according to the pulmonary disorder to be treated. For example, in certain embodiments, the pulmonary disorder is chronic obstructive pulmonary disease. In certain embodiments, the pulmonary disorder is asthma. In certain embodiments, the pulmonary disorder is bronchitis. In certain embodiments, the pulmonary disorder is chronic bronchitis. In certain embodiments, the pulmonary disorder is emphysema. In certain embodiments, the pulmonary disorder is acute respiratory distress syndrome. In certain embodiments, the pulmonary disorder is an infection by a coronavirus. In certain embodiments, the pulmonary disorder is an infection by severe acute respiratory syndrome coronavirus 2 (SARS-CoV-2). In certain embodiments, the coronavirus infection is an infection by severe acute respiratory syndrome coronavirus 2 (SARS-CoV-2). In certain embodiments, the coronavirus infection is an infection by a variant of SARS-CoV-2. In certain embodiments, the coronavirus infection is an infection by a variant of SARS-CoV-2 having the spike protein of SARS-CoV-2. In certain embodiments, the coronavirus infection is an infection by SARS-CoV-2 or a variant thereof selected from B.1.617.2, Cluster 5, Lineage B.1.1.207, Lineage B.1.1.7, Variant of Concern 202102/02, Lineage B.1.1.317, Lineage B.1.1.318, Lineage B.1.351, Lineage B.1.429, Lineage B.1.525, Lineage P.1 (also known as Lineage B.1.1.28), D614G, E484K, N501Y, S477G/N, and P681H.

In certain embodiments, the pulmonary disorder is pneumonia or pleural effusion. In certain embodiments, the pulmonary disorder is edema. In certain embodiments, the pulmonary disorder is bronchitis. In certain embodiments, the pulmonary disorder is chronic bronchitis. In certain embodiments, the pulmonary disorder is pneumonia.

Results Produced by the Methods

The methods may be further characterized according to the results produced by the methods. For example, in certain embodiments, the patient experiences at least a 25% reduction in symptoms from the pulmonary disorder within 1 week after the first day of the treatment method. In certain embodiments, the patient experiences at least a 50% reduction in symptoms from the pulmonary disorder within 1 week after the first day of the treatment method.

B. Methods for Treating a Neurodegenerative Disorder

Another aspect of the invention provides methods for treating a neurodegenerative disorder. This is described in more detail below.

First Method

Another aspect of the invention provides a method of treating a neurodegenerative disorder, comprising intravenously administering to a patient in need thereof a stromal vascular fraction according to the following dosing schedule, in order to treat the neurodegenerative disorder:

a. on the first day:
    i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
    ii. intravenously administer to the patient in need thereof over a duration of about 30 minutes a second injectable pharmaceutical composition containing saline and an aliquot of stromal vascular fraction containing from about 0.2 billion to about 4 billion cells;
  b. on the day that is about 30 days after the first day:
    i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
    ii. intravenously administer to the patient in need thereof over a duration of about 30 minutes a second injectable pharmaceutical composition containing saline and an aliquot of stromal vascular fraction containing from about 0.2 billion to about 4 billion cells; and
  c. on the day that is about 60 days after the first day:
    i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
    ii. intravenously administer to the patient in need thereof over a duration of about 30 minutes a second injectable pharmaceutical composition containing saline and an aliquot of stromal vascular fraction containing from about 0.2 billion to about 4 billion cells;
  wherein the stromal vascular fraction is derived from adipose tissue through sonication of lipoaspirate and without the use of an enzyme or sonication probe.

Second Method

Another aspect of the invention provides a method of treating a neurodegenerative disorder, comprising intravenously administering to a patient in need thereof a stromal vascular fraction according to the following dosing schedule, in order to treat the neurodegenerative disorder:

a. on the first day:
    i. intravenously administer to the patient in need thereof a first injectable pharmaceutical composition containing saline and an aliquot of stromal vascular fraction; and thereafter
    ii. intravenously administer to the patient in need thereof a second injectable pharmaceutical composition containing saline and an aliquot of stromal vascular fraction;
  b. on a day that is at least 5 days after the first day:
    i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction; and c. on a day that is at least 10 days after the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction.

In certain embodiments, step (b) is performed on a day that is at least 20 days after the first day. In certain embodiments, step (b) is performed on a day that is at least 30 days after the first day. In certain embodiments, step (b) is performed on a day that is at about 30 days after the first day. In certain embodiments, step (b) is performed on a day that is from about 25 days to about 35 days after the first day. In certain embodiments, step (c) is performed on a day that is at least 50 days after the first day. In certain embodiments, step (c) is performed on a day that is at least 60 days after the first day. In certain embodiments, step (c) is performed on a day that is from about 50 days to about 70 days after the first day. In certain embodiments, step (c) is performed on a day that is about 60 days after the first day.

In a more specific embodiment, the invention provides a method of treating a neurodegenerative disorder, comprising intravenously administering to a patient in need thereof a stromal vascular fraction according to the following dosing schedule, in order to treat the neurodegenerative disorder:

a. on the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction;

b. on the day that is about 30 days after the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction; and c. on the day that is about 60 days after the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction.

In a more specific embodiment, the invention provides a method of treating neuropathy, comprising intravenously administering to a patient in need thereof a stromal vascular fraction according to the following dosing schedule, in order to treat the neuropathy:

a. on the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

b. on the day that is about 30 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells; and c. on the day that is about 60 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

In certain embodiments, the stromal vascular fraction is derived from adipose tissue through sonication of lipoaspirate and without the use of an enzyme or sonication probe.

In certain embodiments, in step (a), the first injectable pharmaceutical composition is intravenously administered in less than about 70 minutes, 60 minutes, 50 minutes, 40 minutes, 30 minutes, 20 minutes, or 10 minutes. In certain embodiments, in step (a), the first injectable pharmaceutical composition is intravenously administered over from about 25 minutes to about 65 minutes, or from about 40 minutes to about 50 minutes. In certain embodiments, in step (a), the first injectable pharmaceutical composition is intravenously administered over about 45 minutes. In certain embodiments, in step (a), the second injectable pharmaceutical composition is intravenously administered in less than about 60 minutes, 50 minutes, 40 minutes, 30 minutes, 20 minutes, or 10 minutes. In certain embodiments, in step (a), the second injectable pharmaceutical composition is intravenously administered over from about 10 minutes to about 60 minutes, or from about 20 minutes to about 40 minutes. In certain embodiments, in step (a), the second injectable pharmaceutical composition is intravenously administered over about 30 minutes.

In certain embodiments, in step (b), the first injectable pharmaceutical composition is intravenously administered in less than about 70 minutes, 60 minutes, 50 minutes, 40 minutes, 30 minutes, 20 minutes, or 10 minutes. In certain embodiments, in step (b), the first injectable pharmaceutical composition is intravenously administered over from about 25 minutes to about 65 minutes, or from about 40 minutes to about 50 minutes. In certain embodiments, in step (b), the first injectable pharmaceutical composition is intravenously administered over about 45 minutes. In certain embodiments, in step (b), the second injectable pharmaceutical composition is intravenously administered in less than about 60 minutes, 50 minutes, 40 minutes, 30 minutes, 20 minutes, or 10 minutes. In certain embodiments, in step (b), the second injectable pharmaceutical composition is intravenously administered over from about 10 minutes to about 60 minutes, or from about 20 minutes to about 40 minutes. In certain embodiments, in step (b), the second injectable pharmaceutical composition is intravenously administered over about 30 minutes.

In certain embodiments, in step (c), the first injectable pharmaceutical composition is intravenously administered in less than about 70 minutes, 60 minutes, 50 minutes, 40 minutes, 30 minutes, 20 minutes, or 10 minutes. In certain embodiments, in step (c), the first injectable pharmaceutical composition is intravenously administered over from about 25 minutes to about 65 minutes, or from about 40 minutes to about 50 minutes. In certain embodiments, in step (c), the first injectable pharmaceutical composition is intravenously administered over about 45 minutes. In certain embodiments, in step (c), the second injectable pharmaceutical composition is intravenously administered in less than about 60 minutes, 50 minutes, 40 minutes, 30 minutes, 20 minutes, or 10 minutes. In certain embodiments, in step (c), the second injectable pharmaceutical composition is intravenously administered over from about 10 minutes to about 60 minutes, or from about 20 minutes to about 40 minutes. In certain embodiments, in step (c), the second injectable pharmaceutical composition is intravenously administered over about 30 minutes.

In certain embodiments, the method comprises intravenously administering to a patient in need thereof a stromal vascular fraction according to the following dosing schedule, in order to treat the neurodegenerative disorder:

a. on the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 1 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 1 billion cells;
b. on the day that is about 30 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of from about 0.2 billion to about 2 billion cells; and
c. on the day that is about 60 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.1 billion to about 1 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 1 billion cells;
wherein the stromal vascular fraction is derived from adipose tissue through sonication of lipoaspirate and without the use of an enzyme or sonication probe.

In certain embodiments, the method comprises intravenously administering to a patient in need thereof a stromal vascular fraction according to the following dosing schedule, in order to treat the neurodegenerative disorder:

a. on the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 2 billion cells;
b. on the day that is about 30 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 2 billion cells; and
c. on the day that is about 60 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 2 billion cells;
wherein the stromal vascular fraction is derived from adipose tissue through sonication of lipoaspirate and without the use of an enzyme or sonication probe.

In certain embodiments, the method comprises intravenously administering to a patient in need thereof a stromal vascular fraction according to the following dosing schedule, in order to treat the neurodegenerative disorder:

a. on the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and aliquot of stromal vascular fraction containing from about 0.2 billion to about 2 billion cells;
b. on the day that is about 30 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 2 billion cells; and
c. on the day that is about 60 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 2 billion cells;
  wherein the stromal vascular fraction is derived from adipose tissue through sonication of lipoaspirate and without the use of an enzyme or sonication probe.

In certain embodiments, the first injectable pharmaceutical composition contains from about 300 mL to about 450 mL of saline. In certain embodiments, the second injectable pharmaceutical composition contains from about 150 mL to about 250 mL of saline. In certain embodiments, the second injectable pharmaceutical composition contains from about 250 mL to about 300 mL of saline.

In certain embodiments, the first injectable pharmaceutical composition has a volume of from about 300 mL to about 450 mL. In certain embodiments, the first injectable pharmaceutical composition has a volume of from about 180 mL to about 220 mL. In certain embodiments, the first injectable pharmaceutical composition has a volume of about 200 mL.

In certain embodiments, the second injectable pharmaceutical composition has a volume of about 150 mL to about 500 mL. In certain embodiments, the second injectable pharmaceutical composition has a volume of about 250 mL to about 450 mL. In certain embodiments, the second injectable pharmaceutical composition has a volume of about 300 mL to about 420 mL. In certain embodiments, the second injectable pharmaceutical composition has a volume of about 300 mL to about 400 mL. In certain embodiments, the second injectable pharmaceutical composition has a volume of about 200 mL to about 300 mL. In certain embodiments, the second injectable pharmaceutical composition has a volume of about 150 mL to about 200 mL.

Additional Exemplary Features of the First and Second Methods for Treating a Neurodegenerative Disorder Additional exemplary features that may characterize the First and Second Methods for treating a neurodegenerative disorder described herein are provided below and include, for example, characteristics of the injectable pharmaceutical compositions, neurodegenerative disorders to be treated, and results produced by the methods. A more thorough description of such features is provided below. The invention embraces all permutations and combinations of these features.

Injectable Pharmaceutical Compositions

The methods may be further characterized according to characteristics of the injectable pharmaceutical compositions, such as the number of cells in the stromal vascular fraction in the injectable pharmaceutical compositions, the volume of saline in the injectable pharmaceutical compositions, and the total volume of the injectable pharmaceutical compositions. For example, in certain embodiments, the first injectable pharmaceutical composition contains saline and an aliquot of stromal vascular fraction containing from about 0.2 billion to about 0.8 billion cells. In certain embodiments, the first injectable pharmaceutical composition contains saline and an aliquot of stromal vascular fraction containing from about 0.2 billion to about 0.4 billion cells, from about 0.4 billion to about 0.6 billion cells, or from about 0.6 billion to about 0.8 billion cells. In certain embodiments, the second injectable pharmaceutical composition contains saline and an aliquot of stromal vascular fraction containing from about 0.5 billion to about 2.5 billion cells. In certain embodiments, the second injectable pharmaceutical composition contains saline and an aliquot of stromal vascular fraction containing from about 0.5 billion to about 1 billion cells, from about 1 billion to about 2 billion cells, or from about 2 billion to about 2.5 billion cells.

In certain embodiments, the first injectable pharmaceutical composition contains from about 380 mL to about 490 mL of saline. In certain embodiments, the second injectable pharmaceutical composition contains from about 180 mL to about 240 mL of saline. In certain embodiments, the second injectable pharmaceutical composition contains from about 150 mL to about 195 mL of saline.

In certain embodiments, the first injectable pharmaceutical composition has a volume of from about 400 mL to about 600 mL. In certain embodiments, the first injectable pharmaceutical composition has a volume of from about 180 mL to about 220 mL. In certain embodiments, the first injectable pharmaceutical composition has a volume of about 200 mL.

In certain embodiments, the second injectable pharmaceutical composition has a volume of about 150 mL to about 500 mL. In certain embodiments, the second injectable pharmaceutical composition has a volume of about 200 mL to about 450 mL. In certain embodiments, the second injectable pharmaceutical composition has a volume of about 250 mL to about 450 mL. In certain embodiments, the second injectable pharmaceutical composition has a volume of about 300 mL to about 420 mL. In certain embodiments, the second injectable pharmaceutical composition has a volume of about 300 mL to about 400 mL. In certain embodiments, the second injectable pharmaceutical composition has a volume of about 200 mL to about 300 mL. In certain embodiments, the second injectable pharmaceutical composition has a volume of about 150 mL to about 200 mL.

In certain embodiments, the first injectable pharmaceutical composition is intravenously administered at a rate of from about 2 to about 10 mL/min. In certain embodiments, the first injectable pharmaceutical composition is intravenously administered at a rate of from about 4 to about 6 mL/min. In certain embodiments, the first injectable pharmaceutical composition is intravenously administered at a rate of from about 4 to about 5 mL/min. In certain embodiments, the second injectable pharmaceutical composition is intravenously administered at a rate of from about 2 to about 10 mL/min. In certain embodiments, the second injectable pharmaceutical composition is intravenously administered at a rate of from about 4 to about 6 mL/min. In certain embodiments, the second injectable pharmaceutical composition is intravenously administered at a rate of from about 4 to about 5 mL/min. In certain embodiments, the second injectable pharmaceutical composition is intravenously administered at a rate of from about 4 to about 10 mL/min.

Additional Method Steps

The methods may be further characterized according to additional steps that the method further comprises. For example, in certain embodiments, the method further comprises intravenously administering saline to the patient prior to intravenously administering the first injectable pharmaceutical composition to the patient. In certain embodiments, the method further comprises intravenously administering at least about 25, 50, 75, 100, 125, or 150 mL of saline to the patient prior to intravenously administering the first injectable pharmaceutical composition to the patient. In certain embodiments, the method further comprises intravenously administering at least about 100 mL of saline to the patient prior to intravenously administering the first injectable pharmaceutical composition to the patient. In certain embodiments, the method further comprises intravenously administering about 100 mL of saline to the patient prior to intravenously administering the first injectable pharmaceutical composition to the patient. In certain embodiments, the method further comprises intravenously administering over a duration of about 25 minutes an amount of about 100 mL of saline to the patient prior to intravenously administering the first injectable pharmaceutical composition to the patient.

In certain embodiments, the method further comprises the step of: prior to intravenously administering the first injectable pharmaceutical composition to the patient on the first day, adipose tissue is obtained from the patient and processed to provide stromal vascular fraction used in the first injectable pharmaceutical composition and second injectable pharmaceutical composition that are intravenously administered to the patient on the first day.

In certain embodiments, the method further comprises the step of: prior to intravenously administering the first injectable pharmaceutical composition to the patient on the first day or within three days prior to the first day, adipose tissue is obtained from the patient and processed to provide stromal vascular fraction used in the first injectable pharmaceutical composition and second injectable pharmaceutical composition that are intravenously administered to the patient on the first day.

Neurodegenerative Disorders to be Treated

The methods may be further characterized according to the neurodegenerative disorder to be treated. For example, in certain embodiments, the neurodegenerative disorder is multiple sclerosis. In certain embodiments, the neurodegenerative disorder is amyotrophic lateral sclerosis. In certain embodiments, the neurodegenerative disorder is dementia. In certain embodiments, the neurodegenerative disorder is Parkinson's Disease.

Results Produced by the Methods

The methods may be further characterized according to the results produced by the methods. For example, in certain embodiments, the patient experiences at least a 25% reduction in symptoms from the neurodegenerative disorder within 3 months after the first day of the treatment method. In certain embodiments, the patient experiences at least a 50% reduction in symptoms from the neurodegenerative disorder within 3 months after the first day of the treatment method.

C. Methods for Treating Brain Injuries and Psychiatric Disorders

Another aspect of the invention provides methods for treating brain injuries and psychiatric disorders. This is described in more detail below.

First Method

One aspect of the invention provides a method of treating a disorder selected from the group consisting of a brain injury and a psychiatric disorder, comprising intravenously administering to a patient in need thereof a stromal vascular fraction according to the following dosing schedule, in order to treat the disorder:

a. on the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

b. on the day that is about 30 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells; and c. on the day that is about 60 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

Second Method

Another aspect of the invention provides a method of treating a disorder selected from the group consisting of a brain injury and a psychiatric disorder, comprising intravenously administering to a patient in need thereof a stromal vascular fraction according to the following dosing schedule, in order to treat the disorder:

a. on the first day:
   i. intravenously administer to the patient in need thereof a first injectable pharmaceutical composition containing saline and an aliquot of stromal vascular fraction; and thereafter
   ii. intravenously administer to the patient in need thereof a second injectable pharmaceutical composition containing saline and an aliquot of stromal vascular fraction;
b. on the day that is at least 5 days after the first day:
   i. intravenously administer to the patient in need thereof a first injectable pharmaceutical composition containing saline and an aliquot of stromal vascular fraction; and thereafter
   ii. intravenously administer to the patient in need thereof over a duration of about 30 minutes a second injectable pharmaceutical composition containing saline and an aliquot of stromal vascular fraction containing from about 0.2 billion to about 4 billion cells; and
c. on the day that is at least 10 days after the first day:
   i. intravenously administer to the patient in need thereof a first injectable pharmaceutical composition containing saline and an aliquot of stromal vascular fraction; and thereafter
   ii. intravenously administer to the patient in need thereof a second injectable pharmaceutical composition containing saline and an aliquot of stromal vascular fraction.

In certain embodiments, step (b) is performed on a day that is at least 20 days after the first day. In certain embodiments, step (b) is performed on a day that is at least 30 days after the first day. In certain embodiments, step (b) is performed on a day that is at about 30 days after the first day. In certain embodiments, step (b) is performed on a day that is from about 25 days to about 35 days after the first day. In certain embodiments, step (c) is performed on a day that is at least 50 days after the first day. In certain embodiments, step (c) is performed on a day that is at least 60 days after the first day. In certain embodiments, step (c) is performed on a day that is from about 50 days to about 70 days after the first day. In certain embodiments, step (c) is performed on a day that is about 60 days after the first day.

In a more specific embodiment, the invention provides a method of treating a disorder selected from the group consisting of a brain injury and a psychiatric disorder, comprising intravenously administering to a patient in need thereof a stromal vascular fraction according to the following dosing schedule, in order to treat the disorder:

a. on the first day:
   i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction;
b. on the day that is about 30 days after the first day:
   i. intravenously administer to the patient in need thereof a first injectable pharmaceutical composition containing saline and an aliquot of stromal vascular fraction; and thereafter
   ii. intravenously administer to the patient in need thereof over a duration of about 30 minutes a second injectable pharmaceutical composition containing saline and an aliquot of stromal vascular fraction containing from about 0.2 billion to about 4 billion cells; and
c. on the day that is about 60 days after the first day:
   i. intravenously administer to the patient in need thereof a first injectable pharmaceutical composition containing saline and an aliquot of stromal vascular fraction; and thereafter
   ii. intravenously administer to the patient in need thereof a second injectable pharmaceutical composition containing saline and an aliquot of stromal vascular fraction.

In certain embodiments, the stromal vascular fraction is derived from adipose tissue through sonication of lipoaspirate and without the use of an enzyme or sonication probe.

In certain embodiments, in step (a), the first injectable pharmaceutical composition is intravenously administered in less than about 70 minutes, 60 minutes, 50 minutes, 40 minutes, 30 minutes, 20 minutes, or 10 minutes. In certain embodiments, in step (a), the first injectable pharmaceutical composition is intravenously administered over from about 25 minutes to about 65 minutes, or from about 40 minutes to about 50 minutes. In certain embodiments, in step (a), the first injectable pharmaceutical composition is intravenously administered over about 45 minutes. In certain embodiments, in step (a), the second injectable pharmaceutical composition is intravenously administered in less than about 60 minutes, 50 minutes, 40 minutes, 30 minutes, 20 minutes, or 10 minutes. In certain embodiments, in step (a), the second injectable pharmaceutical composition is intravenously administered over from about 10 minutes to about 60 minutes, or from about 20 minutes to about 40 minutes. In certain embodiments, in step (a), the second injectable pharmaceutical composition is intravenously administered over about 30 minutes.

In certain embodiments, in step (b), the first injectable pharmaceutical composition is intravenously administered in less than about 70 minutes, 60 minutes, 50 minutes, 40 minutes, 30 minutes, 20 minutes, or 10 minutes. In certain embodiments, in step (b), the first injectable pharmaceutical composition is intravenously administered over from about 25 minutes to about 65 minutes, or from about 40 minutes to about 50 minutes. In certain embodiments, in step (b), the first injectable pharmaceutical composition is intravenously administered over about 45 minutes. In certain embodiments, in step (b), the second injectable pharmaceutical composition is intravenously administered in less than about 60 minutes, 50 minutes, 40 minutes, 30 minutes, 20 minutes, or 10 minutes. In certain embodiments, in step (b), the second injectable pharmaceutical composition is intravenously administered over from about 10 minutes to about 60 minutes, or from about 20 minutes to about 40 minutes. In certain embodiments, in step (b), the second injectable pharmaceutical composition is intravenously administered over about 30 minutes.

In certain embodiments, in step (c), the first injectable pharmaceutical composition is intravenously administered in less than about 70 minutes, 60 minutes, 50 minutes, 40 minutes, 30 minutes, 20 minutes, or 10 minutes. In certain embodiments, in step (c), the first injectable pharmaceutical composition is intravenously administered over from about 25 minutes to about 65 minutes, or from about 40 minutes to about 50 minutes. In certain embodiments, in step (c), the first injectable pharmaceutical composition is intravenously administered over about 45 minutes. In certain embodiments, in step (c), the second injectable pharmaceutical composition is intravenously administered in less than about 60 minutes, 50 minutes, 40 minutes, 30 minutes, 20 minutes, or 10 minutes. In certain embodiments, in step (c), the second injectable pharmaceutical composition is intravenously administered over from about 10 minutes to about 60 minutes, or from about 20 minutes to about 40 minutes. In certain embodiments, in step (c), the second injectable pharmaceutical composition is intravenously administered over about 30 minutes.

In certain embodiments, the method comprises intravenously administering to a patient in need thereof a stromal vascular fraction according to the following dosing schedule, in order to treat the disorder:

a. on the first day:

i. intravenously administer to the patient in need thereof over a duration of about 45 minutes an amount of about 200 mL of a first injectable pharmaceutical composition containing saline and an aliquot of stromal vascular fraction containing from about 0.25 billion to about 2 billion cells; and thereafter ii. intravenously administer to the patient in need thereof over a duration of about 30 minutes a second injectable pharmaceutical composition containing saline and an aliquot of stromal vascular fraction containing from about 02 billion to about 2 billion cells;

b. on the day that is about 30 days after the first day:

i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter ii. intravenously administer to the patient in need thereof over a duration of about 30 minutes a second injectable pharmaceutical composition containing saline and an aliquot of stromal vascular fraction containing from about 0.1 billion to about 2 billion cells; and c. on the day that is about 60 days after the first day:

i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter ii. intravenously administer to the patient in need thereof over a duration of about 30 minutes a second injectable pharmaceutical composition containing saline and an aliquot of stromal vascular fraction containing from about 0.1 billion to about 2 billion cells;

wherein the stromal vascular fraction is derived from adipose tissue through sonication of lipoaspirate and without the use of an enzyme or sonication probe.

In certain embodiments, the method comprises intravenously administering to a patient in need thereof a stromal vascular fraction according to the following dosing schedule, in order to treat the disorder:

a. on the first day:

i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter ii. intravenously administer to the patient in need thereof over a duration of about 30 minutes a second injectable pharmaceutical composition containing saline and an aliquot of stromal vascular fraction containing from about 0.2 billion to about 2 billion cells;

b. on the day that is about 30 days after the first day:

i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter ii. intravenously administer to the patient in need thereof over a duration of about 30 minutes a second injectable pharmaceutical composition containing saline and an aliquot of stromal vascular fraction containing from about 0.2 billion to about 2 billion cells; and c. on the day that is about 60 days after the first day:

i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter ii. intravenously administer to the patient in need thereof over a duration of about 30 minutes a second injectable pharmaceutical composition containing saline and an aliquot of stromal vascular fraction containing from about 0.1 billion to about 2 billion cells;

wherein the stromal vascular fraction is derived from adipose tissue through sonication of lipoaspirate and without the use of an enzyme or sonication probe.

In certain embodiments, the method comprises intravenously administering to a patient in need thereof a stromal vascular fraction according to the following dosing schedule, in order to treat the disorder:

a. on the first day:

i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter ii. intravenously administer to the patient in need thereof over a duration of about 30 minutes a second injectable pharmaceutical composition containing saline and an aliquot of stromal vascular fraction containing from about 0.2 billion to about 2 billion cells;

b. on the day that is about 30 days after the first day:
   i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
   ii. intravenously administer to the patient in need thereof over a duration of about 30 minutes a second injectable pharmaceutical composition containing saline and an aliquot of stromal vascular fraction containing from about 0.2 billion to about 2 billion cells; and c. on the day that is about 60 days after the first day:
   i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter
   ii. intravenously administer to the patient in need thereof over a duration of about 30 minutes a second injectable pharmaceutical composition containing saline and an aliquot of stromal vascular fraction containing from about 0.1 billion to about 2 billion cells;

wherein the stromal vascular fraction is derived from adipose tissue through sonication of lipoaspirate and without the use of an enzyme or sonication probe.

In certain embodiments, the first injectable pharmaceutical composition has a volume of from about 300 mL to about 500 mL. In certain embodiments, the first injectable pharmaceutical composition has a volume of from about 250 mL to about 350 mL. In certain embodiments, the second injectable pharmaceutical composition has a volume of about 200 mL to about 300 mL. In certain embodiments, the second injectable pharmaceutical composition has a volume of about 150 mL to about 250 mL.

Additional Exemplary Features of the First and Second Methods for Treating Brain Injuries and Psychiatric Disorders Additional exemplary features that may characterize the First and Second Methods for treating brain injuries and psychiatric disorders described herein are provided below and include, for example, characteristics of the injectable pharmaceutical compositions, brain injuries and psychiatric disorders to be treated, and results produced by the methods. A more thorough description of such features is provided below. The invention embraces all permutations and combinations of these features.

Injectable Pharmaceutical Compositions

The methods may be further characterized according to characteristics of the injectable pharmaceutical compositions, such as the number of cells in the stromal vascular fraction in the injectable pharmaceutical compositions, the volume of saline in the injectable pharmaceutical compositions, and the total volume of the injectable pharmaceutical compositions.

For example, in certain embodiments, the first injectable pharmaceutical composition contains saline and an aliquot of stromal vascular fraction containing from about 0.2 billion to about 0.8 billion cells. In certain embodiments, the first injectable pharmaceutical composition contains saline and an aliquot of stromal vascular fraction containing from about 0.2 billion to about 0.4 billion cells, from about 0.4 billion to about 0.6 billion cells, or from about 0.6 billion to about 0.8 billion cells. In certain embodiments, the second injectable pharmaceutical composition contains saline and an aliquot of stromal vascular fraction containing from about 0.5 billion to about 2.5 billion cells. In certain embodiments, the second injectable pharmaceutical composition contains saline and an aliquot of stromal vascular fraction containing from about 0.5 billion to about 1 billion cells, from about 1 billion to about 2 billion cells, or from about 2 billion to about 2.5 billion cells.

In certain embodiments, the first injectable pharmaceutical composition contains from about 380 mL to about 490 mL of saline. In certain embodiments, the second injectable pharmaceutical composition contains from about 180 mL to about 240 mL of saline. In certain embodiments, the second injectable pharmaceutical composition contains from about 150 mL to about 195 mL of saline.

In certain embodiments, the first injectable pharmaceutical composition has a volume of from about 400 mL to about 600 mL. In certain embodiments, the first injectable pharmaceutical composition has a volume of from about 180 mL to about 220 mL. In certain embodiments, the first injectable pharmaceutical composition has a volume of about 200 mL.

In certain embodiments, the second injectable pharmaceutical composition has a volume of about 150 mL to about 500 mL. In certain embodiments, the second injectable pharmaceutical composition has a volume of about 200 mL to about 450 mL. In certain embodiments, the second injectable pharmaceutical composition has a volume of about 250 mL to about 450 mL. In certain embodiments, the second injectable pharmaceutical composition has a volume of about 300 mL to about 420 mL. In certain embodiments, the second injectable pharmaceutical composition has a volume of about 300 mL to about 400 mL. In certain embodiments, the second injectable pharmaceutical composition has a volume of about 200 mL to about 300 mL. In certain embodiments, the second injectable pharmaceutical composition has a volume of about 150 mL to about 200 mL.

In certain embodiments, the first injectable pharmaceutical composition is intravenously administered at a rate of from about 2 to about 10 mL/min. In certain embodiments, the first injectable pharmaceutical composition is intravenously administered at a rate of from about 4 to about 6 mL/min. In certain embodiments, the first injectable pharmaceutical composition is intravenously administered at a rate of from about 4 to about 5 mL/min. In certain embodiments, the second injectable pharmaceutical composition is intravenously administered at a rate of from about 2 to about 10 mL/min. In certain embodiments, the second injectable pharmaceutical composition is intravenously administered at a rate of from about 4 to about 6 mL/min. In certain embodiments, the second injectable pharmaceutical composition is intravenously administered at a rate of from about 4 to about 5 mL/min. In certain embodiments, the second injectable pharmaceutical composition is intravenously administered at a rate of from about 4 to about 10 mL/min.

Additional Method Steps

The methods may be further characterized according to additional steps that the method further comprises. For example, in certain embodiments, the method further comprises intravenously administering saline to the patient prior to intravenously administering the first injectable pharmaceutical composition to the patient. In certain embodiments, the method further comprises intravenously administering at least about 25, 50, 75, 100, 125, or 150 mL of saline to the patient prior to intravenously administering the first injectable pharmaceutical composition to the patient. In certain embodiments, the method further comprises intravenously administering at least about 100 mL of saline to the patient prior to intravenously administering the first injectable pharmaceutical composition to the patient. In certain embodiments, the method further comprises intravenously administering about 100 mL of saline to the patient prior to intravenously administering the first injectable pharmaceutical composition to the patient. In certain embodiments, the method further comprises intravenously administering over a duration of about 25 minutes an amount of about 100 mL of saline to the patient prior to intravenously administering the first injectable pharmaceutical composition to the patient.

In certain embodiments, the method further comprises the step of: prior to intravenously administering the first injectable pharmaceutical composition to the patient on the first day, adipose tissue is obtained from the patient and processed to provide stromal vascular fraction used in the first injectable pharmaceutical composition and second injectable pharmaceutical composition that are intravenously administered to the patient on the first day.

In certain embodiments, the method further comprises the step of: prior to intravenously administering the first injectable pharmaceutical composition to the patient on the first day or within three days prior to the first day, adipose tissue is obtained from the patient and processed to provide stromal vascular fraction used in the first injectable pharmaceutical composition and second injectable pharmaceutical composition that are intravenously administered to the patient on the first day.

Brain Injuries and Psychiatric Disorders to be Treated

The methods may be further characterized according to the brain injuries and psychiatric disorders to be treated. For example, in certain embodiments, the disorder is a brain injury. In certain embodiments, the disorder is a stroke. In certain embodiments, the disorder is chronic traumatic encephalopathy. In certain embodiments, the disorder is traumatic brain injury. In certain embodiments, the disorder is a psychiatric disorder. In certain embodiments, the disorder is post-traumatic stress disorder. In certain embodiments, the disorder is anxiety. In certain embodiments, the disorder is post-concussion syndrome.

Results Produced by the Methods

The methods may be further characterized according to the results produced by the methods. For example, in certain embodiments, the patient experiences at least a 25% reduction in symptoms from the disorder within 3 months after the first day of the treatment method. In certain embodiments, the patient experiences at least a 50% reduction in symptoms from the neurodegenerative disorder within 3 months after the first day of the treatment method.

D. Methods for Treating a Metabolic Disorder

Another aspect of the invention provides methods for treating a metabolic disorder. This is described in more detail below.

First Method

One aspect of the invention provides a method of treating a metabolic disorder, comprising intravenously administering to a patient in need thereof a stromal vascular fraction according to the following dosing schedule, in order to treat the metabolic disorder:

a. on the first day:
i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
ii. intravenously administer to the patient in need thereof over a duration of about 30 minutes a second injectable pharmaceutical composition containing saline and an aliquot of stromal vascular fraction containing from about 0.2 billion to about 4 billion cells;
b. on the day that is about 14 days after the first day:
i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
ii. intravenously administer to the patient in need thereof over a duration of about 30 minutes a second injectable pharmaceutical composition containing saline and an aliquot of stromal vascular fraction containing from about 0.2 billion to about 4 billion cells;
c. on the day that is about 35 days after the first day:
i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
ii. intravenously administer to the patient in need thereof over a duration of about 30 minutes a second injectable pharmaceutical composition containing saline and an aliquot of stromal vascular fraction containing from about 0.2 billion to about 4 billion cells;
d. on the day that is about 65 days after the first day:
i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
ii. intravenously administer to the patient in need thereof over a duration of about 30 minutes a second injectable pharmaceutical composition containing saline and an aliquot of stromal vascular fraction containing from about 0.2 billion to about 4 billion cells; and
e. on the day that is about 95 days after the first day:
i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

Second Method

Another aspect of the invention provides a method of treating a metabolic disorder, comprising intravenously administering to a patient in need thereof a stromal vascular fraction according to the following dosing schedule, in order to treat the metabolic disorder:

a. on the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction;
b. on the day that is at least 5 days after the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction;
c. on the day that is at least 10 days after the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction;
d. on the day that at least 20 days after the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction; and
e. on the day that is at least 40 days after the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction.

In certain embodiments, step (b) is performed on a day that is at least 10 days after the first day. In certain embodiments, step (b) is performed on a day that is at least 14 days after the first day. In certain embodiments, step (b) is performed on a day that is at about 14 days after the first day. In certain embodiments, step (b) is performed on a day that is from about 10 days to about 20 days after the first day. In certain embodiments, step (c) is performed on a day that is at least 20 days after the first day. In certain embodiments, step (c) is performed on a day that is at least 35 days after the first day. In certain embodiments, step (c) is performed on a day that is about 35 days after the first day. In certain embodiments, step (c) is performed on a day that is from about 25 days to about 45 days after the first day. In certain embodiments, step (d) is performed on a day that is at least 40 days after the first day. In certain embodiments, step (d) is performed on a day that is at least 65 days after the first day. In certain embodiments, step (d) is performed on a day that is about 65 days after the first day. In certain embodiments, step (d) is performed on a day that is from about 55 days to about 75 days after the first day. In certain embodiments, step (e) is performed on a day that is at least 65 days after the first day. In certain embodiments, step (e) is performed on a day that is at least 95 days after the first day. In certain embodiments, step (e) is performed on a day that is about 95 days after the first day. In certain embodiments, step (e) is performed on a day that is from about 80 days to about 110 days after the first day.

In a more specific embodiment, the invention provides a method of treating a metabolic disorder, comprising intravenously administering to a patient in need thereof a stromal vascular fraction according to the following dosing schedule, in order to treat the metabolic disorder:

a. on the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction;
b. on the day that is about 14 days after the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction;
c. on the day that is about 35 days after the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction;
d. on the day that is about 65 days after the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction; and
e. on the day that is about 95 days after the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction.

In certain embodiments, the stromal vascular fraction is derived from adipose tissue through sonication of lipoaspirate and without the use of an enzyme or sonication probe.

In certain embodiments, in step (a), the first injectable pharmaceutical composition is intravenously administered in less than about 70 minutes, 60 minutes, 50 minutes, 40 minutes, 30 minutes, 20 minutes, or 10 minutes. In certain embodiments, in step (a), the first injectable pharmaceutical composition is intravenously administered over from about 25 minutes to about 65 minutes, or from about 40 minutes to about 50 minutes. In certain embodiments, in step (a), the first injectable pharmaceutical composition is intravenously administered over about 45 minutes. In certain embodiments, in step (a), the second injectable pharmaceutical composition is intravenously administered in less than about 60 minutes, 50 minutes, 40 minutes, 30 minutes, 20 minutes, or 10 minutes. In certain embodiments, in step (a), the second injectable pharmaceutical composition is intravenously administered over from about 10 minutes to about 60 minutes, or from about 20 minutes to about 40 minutes. In certain embodiments, in step (a), the second injectable pharmaceutical composition is intravenously administered over about 30 minutes.

In certain embodiments, in step (b), the first injectable pharmaceutical composition is intravenously administered in less than about 70 minutes, 60 minutes, 50 minutes, 40 minutes, 30 minutes, 20 minutes, or 10 minutes. In certain embodiments, in step (b), the first injectable pharmaceutical composition is intravenously administered over from about 25 minutes to about 65 minutes, or from about 40 minutes to about 50 minutes. In certain embodiments, in step (b), the first injectable pharmaceutical composition is intravenously administered over about 45 minutes. In certain embodiments, in step (b), the second injectable pharmaceutical composition is intravenously administered in less than about 60 minutes, 50 minutes, 40 minutes, 30 minutes, 20 minutes, or 10 minutes. In certain embodiments, in step (b), the second injectable pharmaceutical composition is intravenously administered over from about 10 minutes to about 60 minutes, or from about 20 minutes to about 40 minutes. In certain embodiments, in step (b), the second injectable pharmaceutical composition is intravenously administered over about 30 minutes.

In certain embodiments, in step (c), the first injectable pharmaceutical composition is intravenously administered in less than about 70 minutes, 60 minutes, 50 minutes, 40 minutes, 30 minutes, 20 minutes, or 10 minutes. In certain embodiments, in step (c), the first injectable pharmaceutical composition is intravenously administered over from about 25 minutes to about 65 minutes, or from about 40 minutes to about 50 minutes. In certain embodiments, in step (c), the first injectable pharmaceutical composition is intravenously administered over about 45 minutes. In certain embodiments, in step (c), the second injectable pharmaceutical composition is intravenously administered in less than about 60 minutes, 50 minutes, 40 minutes, 30 minutes, 20 minutes, or 10 minutes. In certain embodiments, in step (c), the second injectable pharmaceutical composition is intravenously administered over from about 10 minutes to about 60 minutes, or from about 20 minutes to about 40 minutes. In certain embodiments, in step (c), the second injectable pharmaceutical composition is intravenously administered over about 30 minutes.

In certain embodiments, in step (d), the first injectable pharmaceutical composition is intravenously administered in less than about 70 minutes, 60 minutes, 50 minutes, 40 minutes, 30 minutes, 20 minutes, or 10 minutes. In certain embodiments, in step (d), the first injectable pharmaceutical composition is intravenously administered over from about 25 minutes to about 65 minutes, or from about 40 minutes to about 50 minutes. In certain embodiments, in step (d), the first injectable pharmaceutical composition is intravenously administered over about 45 minutes. In certain embodiments, in step (d), the second injectable pharmaceutical composition is intravenously administered in less than about 60 minutes, 50 minutes, 40 minutes, 30 minutes, 20 minutes, or 10 minutes. In certain embodiments, in step (d), the second injectable pharmaceutical composition is intravenously administered over from about 10 minutes to about 60 minutes, or from about 20 minutes to about 40 minutes. In certain embodiments, in step (d), the second injectable pharmaceutical composition is intravenously administered over about 30 minutes.

In certain embodiments, in step (e), the first injectable pharmaceutical composition is intravenously administered in less than about 70 minutes, 60 minutes, 50 minutes, 40 minutes, 30 minutes, 20 minutes, or 10 minutes. In certain embodiments, in step (e), the first injectable pharmaceutical composition is intravenously administered over from about 25 minutes to about 65 minutes, or from about 40 minutes to about 50 minutes. In certain embodiments, in step (e), the first injectable pharmaceutical composition is intravenously administered over about 45 minutes. In certain embodiments, in step (e), the second injectable pharmaceutical composition is intravenously administered in less than about 60 minutes, 50 minutes, 40 minutes, 30 minutes, 20 minutes, or 10 minutes. In certain embodiments, in step (e), the second injectable pharmaceutical composition is intravenously administered over from about 10 minutes to about 60 minutes, or from about 20 minutes to about 40 minutes. In certain embodiments, in step (e), the second injectable pharmaceutical composition is intravenously administered over about 30 minutes.

In certain embodiments, the method comprises intravenously administering to a patient in need thereof a stromal vascular fraction according to the following dosing schedule, in order to treat the metabolic disorder:

a. on the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 2 billion cells;

b. on the day that is about 14 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 2 billion cells;

c. on the day that is about 35 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 2 billion cells;

d. on the day that is about 65 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 2 billion cells; and e. on the day that is about 95 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 2 billion cells;

wherein the stromal vascular fraction is derived from adipose tissue through sonication of lipoaspirate and without the use of an enzyme or sonication probe.

In certain embodiments, the method comprises intravenously administering to a patient in need thereof a stromal vascular fraction according to the following dosing schedule, in order to treat the metabolic disorder:

a. on the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 2 billion cells;

b. on the day that is about 14 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 2 billion cells;

c. on the day that is about 35 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 2 billion cells;

d. on the day that is about 65 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 2 billion cells; and e. on the day that is about 95 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 2 billion cells;

wherein the stromal vascular fraction is derived from adipose tissue through sonication of lipoaspirate and without the use of an enzyme or sonication probe.

In certain embodiments, the method comprises intravenously administering to a patient in need thereof a stromal vascular fraction according to the following dosing schedule, in order to treat the metabolic disorder:

a. on the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter ii. intravenously administer to the patient in need thereof over a duration of about 30 minutes a second injectable pharmaceutical composition containing saline and an aliquot of stromal vascular fraction containing from about 0.2 billion to about 2 billion cells;

b. on the day that is about 14 days after the first day:

i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter ii. intravenously administer to the patient in need thereof over a duration of about 30 minutes a second injectable pharmaceutical composition containing saline and an aliquot of stromal vascular fraction containing from about 0.1 billion to about 2 billion cells;

c. on the day that is about 35 days after the first day:

i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter ii. intravenously administer to the patient in need thereof over a duration of about 30 minutes a second injectable pharmaceutical composition containing saline and an aliquot of stromal vascular fraction containing from about 0.1 billion to about 2 billion cells;

d. on the day that is about 65 days after the first day:

i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter ii. intravenously administer to the patient in need thereof over a duration of about 30 minutes a second injectable pharmaceutical composition containing saline and an aliquot of stromal vascular fraction containing from about 0.1 billion to about 2 billion cells; and e. on the day that is about 95 days after the first day:

i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter ii. intravenously administer to the patient in need thereof over a duration of about 30 minutes a second injectable pharmaceutical composition containing saline and an aliquot of stromal vascular fraction containing from about 0.1 billion to about 2 billion cells;

wherein the stromal vascular fraction is derived from adipose tissue through sonication of lipoaspirate and without the use of an enzyme or sonication probe.

In certain embodiments, the first injectable pharmaceutical composition has a volume of from about 250 mL to about 350 mL. In certain embodiments, the second injectable pharmaceutical composition has a volume of about 100 mL to about 250 mL. In certain embodiments, the second injectable pharmaceutical composition has a volume of about 150 mL to about 300 mL. In certain embodiments, the second injectable pharmaceutical composition has a volume of about 200 mL to about 300 mL.

Additional Exemplary Features of the First and Second Methods for Treating a Metabolic Disorder Additional exemplary features that may characterize the First and Second Methods for Treating a Metabolic Disorder described herein are provided below and include, for example, characteristics of the injectable pharmaceutical compositions, metabolic disorders to be treated, and results produced by the methods. A more thorough description of such features is provided below. The invention embraces all permutations and combinations of these features.

Injectable Pharmaceutical Compositions

The methods may be further characterized according to characteristics of the injectable pharmaceutical compositions, such as the number of cells in the stromal vascular fraction in the injectable pharmaceutical compositions, the volume of saline in the injectable pharmaceutical compositions, and the total volume of the injectable pharmaceutical compositions. For example, in certain embodiments, the first injectable pharmaceutical composition contains saline and an aliquot of stromal vascular fraction containing from about 0.2 billion to about 0.8 billion cells. In certain embodiments, the first injectable pharmaceutical composition contains saline and an aliquot of stromal vascular fraction containing from about 0.2 billion to about 0.4 billion cells, from about 0.4 billion to about 0.6 billion cells, or from about 0.6 billion to about 0.8 billion cells. In certain embodiments, the second injectable pharmaceutical composition contains saline and an aliquot of stromal vascular fraction containing from about 0.5 billion to about 2.5 billion cells. In certain embodiments, the second injectable pharmaceutical composition contains saline and an aliquot of stromal vascular fraction containing from about 0.5 billion to about 1 billion cells, from about 1 billion to about 2 billion cells, or from about 2 billion to about 2.5 billion cells.

In certain embodiments, the first injectable pharmaceutical composition contains from about 380 mL to about 490 mL of saline. In certain embodiments, the first injectable pharmaceutical composition contains from about 150 mL to about 195 mL of saline. In certain embodiments, the second injectable pharmaceutical composition contains from about 180 mL to about 240 mL of saline.

In certain embodiments, the first injectable pharmaceutical composition has a volume of from about 400 mL to about 600 mL. In certain embodiments, the first injectable pharmaceutical composition has a volume of from about 180 mL to about 220 mL. In certain embodiments, the first injectable pharmaceutical composition has a volume of about 200 mL.

In certain embodiments, the second injectable pharmaceutical composition has a volume of about 150 mL to about 500 mL. In certain embodiments, the second injectable pharmaceutical composition has a volume of about 200 mL to about 450 mL. In certain embodiments, the second injectable pharmaceutical composition has a volume of about 250 mL to about 450 mL. In certain embodiments, the second injectable pharmaceutical composition has a volume of about 300 mL to about 420 mL. In certain embodiments, the second injectable pharmaceutical composition has a volume of about 300 mL to about 400 mL. In certain embodiments, the second injectable pharmaceutical composition has a volume of about 200 mL to about 300 mL. In certain embodiments, the second injectable pharmaceutical composition has a volume of about 150 mL to about 200 mL.

In certain embodiments, the first injectable pharmaceutical composition is intravenously administered at a rate of from about 2 to about 10 mL/min. In certain embodiments, the first injectable pharmaceutical composition is intravenously administered at a rate of from about 4 to about 6 mL/min. In certain embodiments, the first injectable pharmaceutical composition is intravenously administered at a rate of from about 4 to about 5 mL/min. In certain embodiments, the second injectable pharmaceutical composition is intravenously administered at a rate of from about 2 to about 10 mL/min. In certain embodiments, the second injectable pharmaceutical composition is intravenously administered at a rate of from about 4 to about 6 mL/min. In certain embodiments, the second injectable pharmaceutical composition is intravenously administered at a rate of from about 4 to about 5 mL/min. In certain embodiments, the second injectable pharmaceutical composition is intravenously administered at a rate of from about 4 to about 10 mL/min.

Additional Method Steps

The methods may be further characterized according to additional steps that the method further comprises. For example, in certain embodiments, the method further comprises intravenously administering saline to the patient prior to intravenously administering the first injectable pharmaceutical composition to the patient. In certain embodiments, the method further comprises intravenously administering at least about 25, 50, 75, 100, 125, or 150 mL of saline to the patient prior to intravenously administering the first injectable pharmaceutical composition to the patient. In certain embodiments, the method further comprises intravenously administering at least about 100 mL of saline to the patient prior to intravenously administering the first injectable pharmaceutical composition to the patient. In certain embodiments, the method further comprises intravenously administering about 100 mL of saline to the patient prior to intravenously administering the first injectable pharmaceutical composition to the patient. In certain embodiments, the method further comprises intravenously administering over a duration of about 25 minutes an amount of about 100 mL of saline to the patient prior to intravenously administering the first injectable pharmaceutical composition to the patient.

In certain embodiments, the method further comprises the step of: prior to intravenously administering the first injectable pharmaceutical composition to the patient on the first day, adipose tissue is obtained from the patient and processed to provide stromal vascular fraction used in the first injectable pharmaceutical composition and second injectable pharmaceutical composition that are intravenously administered to the patient on the first day.

In certain embodiments, the method further comprises the step of: prior to intravenously administering the first injectable pharmaceutical composition to the patient on the first day or within three days prior to the first day, adipose tissue is obtained from the patient and processed to provide stromal vascular fraction used in the first injectable pharmaceutical composition and second injectable pharmaceutical composition that are intravenously administered to the patient on the first day.

Metabolic Disorders to be Treated

The methods may be further characterized according to the metabolic disorder to be treated. For example, in certain embodiments, the metabolic disorder is diabetes mellitus. In certain embodiments, the metabolic disorder is type I diabetes, type 2 diabetes, or metabolic syndrome. In certain embodiments, the metabolic disorder is type I diabetes or type 2 diabetes. In certain embodiments, the metabolic disorder is type I diabetes. In certain embodiments, the metabolic disorder is type 2 diabetes. In certain embodiments, the metabolic disorder is metabolic syndrome.

Results Produced by the Methods

The methods may be further characterized according to the results produced by the methods. For example, in certain embodiments, the patient experiences at least a 25% reduction in symptoms from the disorder within 4 months after the first day of the treatment method. In certain embodiments, the patient experiences at least a 50% reduction in symptoms from the disorder within 4 months after the first day of the treatment method.

E. Methods for Treating Pain

Another aspect of the invention provides methods for treating pain. This is described in more detail below.

First Method

One aspect of the invention provides a method of treating pain, comprising intravenously administering to a patient in need thereof a stromal vascular fraction according to the following dosing schedule, in order to treat the pain:

a. on the first day:
  i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 4 billion cells;

b. on the day that is about 90 days after the first day:
  i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 4 billion cells; and c. on the day that is about 210 days after the first day:
  i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

Second Method

Another aspect of the invention provides a method of treating pain, comprising intravenously administering to a patient in need thereof a stromal vascular fraction according to the following dosing schedule, in order to treat the pain:

a. on the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction;
b. on the day that is at least 30 days after the first day:
  i. intravenously administer to the patient in need thereof over a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction; and
c. on the day that is at least 60 days after the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction.

In certain embodiments, step (b) is performed on a day that is at least 50 days after the first day. In certain embodiments, step (b) is performed on a day that is at least 70 days after the first day. In certain embodiments, step (b) is performed on a day that is at least 90 days after the first day. In certain embodiments, step (b) is performed on a day that is at about 90 days after the first day. In certain embodiments, step (b) is performed on a day that is from about 70 days to about 110 days after the first day. In certain embodiments, step (c) is performed on a day that is at least 90 days after the first day. In certain embodiments, step (c) is performed on a day that is at least 150 days after the first day. In certain embodiments, step (c) is performed on a day that is at least 210 days after the first day. In certain embodiments, step (c) is performed on a day that is about 210 days after the first day. In certain embodiments, step (c) is performed on a day that is from about 180 days to about 240 days after the first day.

In a more specific embodiment, the invention provides a method of treating pain, comprising intravenously administering to a patient in need thereof a stromal vascular fraction according to the following dosing schedule, in order to treat the pain:

a. on the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction;
b. on the day that is about 90 days after the first day:
  i. intravenously administer to the patient in need thereof over a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction; and
c. on the day that is about 210 days after the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction.

In certain embodiments, the stromal vascular fraction is derived from adipose tissue through sonication of lipoaspirate and without the use of an enzyme or sonication probe.

In certain embodiments, in step (a), the first injectable pharmaceutical composition is intravenously administered in less than about 70 minutes, 60 minutes, 50 minutes, 40 minutes, 30 minutes, 20 minutes, or 10 minutes. In certain embodiments, in step (a), the first injectable pharmaceutical composition is intravenously administered over from about 25 minutes to about 65 minutes, or from about 40 minutes to about 50 minutes. In certain embodiments, in step (a), the first injectable pharmaceutical composition is intravenously administered over about 45 minutes. In certain embodiments, in step (a), the second injectable pharmaceutical composition is intravenously administered in less than about 60 minutes, 50 minutes, 40 minutes, 30 minutes, 20 minutes, or 10 minutes. In certain embodiments, in step (a), the second injectable pharmaceutical composition is intravenously administered over from about 10 minutes to about 60 minutes, or from about 20 minutes to about 40 minutes. In certain embodiments, in step (a), the second injectable pharmaceutical composition is intravenously administered over about 30 minutes.

In certain embodiments, in step (b), the first injectable pharmaceutical composition is intravenously administered in less than about 70 minutes, 60 minutes, 50 minutes, 40 minutes, 30 minutes, 20 minutes, or 10 minutes. In certain embodiments, in step (b), the first injectable pharmaceutical composition is intravenously administered over from about 25 minutes to about 65 minutes, or from about 40 minutes to about 50 minutes. In certain embodiments, in step (b), the first injectable pharmaceutical composition is intravenously administered over about 45 minutes. In certain embodiments, in step (b), the second injectable pharmaceutical composition is intravenously administered in less than about 60 minutes, 50 minutes, 40 minutes, 30 minutes, 20 minutes, or 10 minutes. In certain embodiments, in step (b), the second injectable pharmaceutical composition is intravenously administered over from about 10 minutes to about 60 minutes, or from about 20 minutes to about 40 minutes. In certain embodiments, in step (b), the second injectable pharmaceutical composition is intravenously administered over about 30 minutes.

In certain embodiments, in step (c), the first injectable pharmaceutical composition is intravenously administered in less than about 70 minutes, 60 minutes, 50 minutes, 40 minutes, 30 minutes, 20 minutes, or 10 minutes. In certain embodiments, in step (c), the first injectable pharmaceutical composition is intravenously administered over from about 25 minutes to about 65 minutes, or from about 40 minutes to about 50 minutes. In certain embodiments, in step (c), the first injectable pharmaceutical composition is intravenously administered over about 45 minutes. In certain embodiments, in step (c), the second injectable pharmaceutical composition is intravenously administered in less than about 60 minutes, 50 minutes, 40 minutes, 30 minutes, 20 minutes, or 10 minutes. In certain embodiments, in step (c), the second injectable pharmaceutical composition is intravenously administered over from about 10 minutes to about 60 minutes, or from about 20 minutes to about 40 minutes. In certain embodiments, in step (c), the second injectable pharmaceutical composition is intravenously administered over about 30 minutes.

In certain embodiments, the method comprises intravenously administering to a patient in need thereof a stromal vascular fraction according to the following dosing schedule, in order to treat the pain:

a. on the first day:
    i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
    ii. intravenously administer to the patient in need thereof over a duration of about 30 minutes a second injectable pharmaceutical composition containing saline and an aliquot of stromal vascular fraction containing from about 0.2 billion to about 2 billion cells;
b. on the day that is about 90 days after the first day:
    i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
    ii. intravenously administer to the patient in need thereof over a duration of about 30 minutes a second injectable pharmaceutical composition containing saline and an aliquot of stromal vascular fraction containing from about 0.1 billion to about 2 billion cells; and
c. on the day that is about 210 days after the first day:
    i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
    ii. intravenously administer to the patient in need thereof over a duration of about 30 minutes a second injectable pharmaceutical composition containing saline and an aliquot of stromal vascular fraction containing from about 0.1 billion to about 2 billion cells;
wherein the stromal vascular fraction is derived from adipose tissue through sonication of lipoaspirate and without the use of an enzyme or sonication probe.

In certain embodiments, the method comprises intravenously administering to a patient in need thereof a stromal vascular fraction according to the following dosing schedule, in order to treat the pain:

a. on the first day:
    i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
    ii. intravenously administer to the patient in need thereof over a duration of about 30 minutes a second injectable pharmaceutical composition containing saline and an aliquot of stromal vascular fraction containing from about 0.2 billion to about 2 billion cells;
b. on the day that is about 90 days after the first day:
    i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
    ii. intravenously administer to the patient in need thereof over a duration of about 30 minutes a second injectable pharmaceutical composition containing saline and an aliquot of stromal vascular fraction containing from about 0.2 billion to about 2 billion cells; and
c. on the day that is about 210 days after the first day:
    i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter
    ii. intravenously administer to the patient in need thereof over a duration of about 30 minutes a second injectable pharmaceutical composition containing saline and an aliquot of stromal vascular fraction containing from about 0.1 billion to about 2 billion cells;
wherein the stromal vascular fraction is derived from adipose tissue through sonication of lipoaspirate and without the use of an enzyme or sonication probe.

In certain embodiments, the first injectable pharmaceutical composition has a volume of from about 200 mL to about 350 mL. In certain embodiments, the first injectable pharmaceutical composition has a volume of from about 250 mL to about 350 mL. In certain embodiments, the first injectable pharmaceutical composition has a volume of from about 250 mL to about 300 mL. In certain embodiments, the second injectable pharmaceutical composition has a volume of about 150 mL to about 300 mL. In certain embodiments, the second injectable pharmaceutical composition has a volume of about 200 mL to about 300 mL.

Additional Exemplary Features of the First and Second Methods for Treating Pain

Additional exemplary features that may characterize the First and Second Methods for Treating Pain described herein are provided below and include, for example, characteristics of the injectable pharmaceutical compositions, types of pain to be treated, and results produced by the methods. A more thorough description of such features is provided below. The invention embraces all permutations and combinations of these features.

Injectable Pharmaceutical Compositions

The methods may be further characterized according to characteristics of the injectable pharmaceutical compositions, such as the number of cells in the stromal vascular fraction in the injectable pharmaceutical compositions, the volume of saline in the injectable pharmaceutical compositions, and the total volume of the injectable pharmaceutical compositions. For example, in certain embodiments, the first injectable pharmaceutical composition contains saline and an aliquot of stromal vascular fraction containing from about 0.2 billion to about 0.8 billion cells. In certain embodiments, the first injectable pharmaceutical composition contains saline and an aliquot of stromal vascular fraction containing from about 0.2 billion to about 0.4 billion cells, from about 0.4 billion to about 0.6 billion cells, or from about 0.6 billion to about 0.8 billion cells. In certain embodiments, the second injectable pharmaceutical composition contains saline and an aliquot of stromal vascular fraction containing from about 0.5 billion to about 2.5 billion cells. In certain embodiments, the second injectable pharmaceutical composition contains saline and an aliquot of stromal vascular fraction containing from about 0.5 billion to about 1 billion cells, from about 1 billion to about 2 billion cells, or from about 2 billion to about 2.5 billion cells.

In certain embodiments, the first injectable pharmaceutical composition contains from about 380 mL to about 490 mL of saline. In certain embodiments, the first injectable pharmaceutical composition contains from about 150 mL to about 195 mL of saline. In certain embodiments, the second injectable pharmaceutical composition contains from about 180 mL to about 240 mL of saline.

In certain embodiments, the first injectable pharmaceutical composition has a volume of from about 400 mL to about 600 mL. In certain embodiments, the first injectable pharmaceutical composition has a volume of from about 180 mL to about 220 mL. In certain embodiments, the first injectable pharmaceutical composition has a volume of about 200 mL.

In certain embodiments, the second injectable pharmaceutical composition has a volume of about 150 mL to about 500 mL. In certain embodiments, the second injectable pharmaceutical composition has a volume of about 200 mL to about 450 mL. In certain embodiments, the second injectable pharmaceutical composition has a volume of about 250 mL to about 450 mL. In certain embodiments, the second injectable pharmaceutical composition has a volume of about 300 mL to about 420 mL. In certain embodiments, the second injectable pharmaceutical composition has a volume of about 300 mL to about 400 mL. In certain embodiments, the second injectable pharmaceutical composition has a volume of about 200 mL to about 300 mL. In certain embodiments, the second injectable pharmaceutical composition has a volume of about 150 mL to about 200 mL.

In certain embodiments, the first injectable pharmaceutical composition is intravenously administered at a rate of from about 2 to about 10 mL/min. In certain embodiments, the first injectable pharmaceutical composition is intravenously administered at a rate of from about 4 to about 6 mL/min. In certain embodiments, the first injectable pharmaceutical composition is intravenously administered at a rate of from about 4 to about 5 mL/min. In certain embodiments, the second injectable pharmaceutical composition is intravenously administered at a rate of from about 2 to about 10 mL/min. In certain embodiments, the second injectable pharmaceutical composition is intravenously administered at a rate of from about 4 to about 6 mL/min. In certain embodiments, the second injectable pharmaceutical composition is intravenously administered at a rate of from about 4 to about 5 mL/min. In certain embodiments, the second injectable pharmaceutical composition is intravenously administered at a rate of from about 4 to about 10 mL/min.

Additional Method Steps

The methods may be further characterized according to additional steps that the method further comprises. For example, in certain embodiments, the method further comprises intravenously administering saline to the patient prior to intravenously administering the first injectable pharmaceutical composition to the patient. In certain embodiments, the method further comprises intravenously administering at least about 25, 50, 75, 100, 125, or 150 mL of saline to the patient prior to intravenously administering the first injectable pharmaceutical composition to the patient. In certain embodiments, the method further comprises intravenously administering at least about 100 mL of saline to the patient prior to intravenously administering the first injectable pharmaceutical composition to the patient. In certain embodiments, the method further comprises intravenously administering about 100 mL of saline to the patient prior to intravenously administering the first injectable pharmaceutical composition to the patient. In certain embodiments, the method further comprises intravenously administering over a duration of about 25 minutes an amount of about 100 mL of saline to the patient prior to intravenously administering the first injectable pharmaceutical composition to the patient.

In certain embodiments, the method further comprises the step of: prior to intravenously administering the first injectable pharmaceutical composition to the patient on the first day, adipose tissue is obtained from the patient and processed to provide stromal vascular fraction used in the first injectable pharmaceutical composition and second injectable pharmaceutical composition that are intravenously administered to the patient on the first day.

In certain embodiments, the method further comprises the step of: prior to intravenously administering the first injectable pharmaceutical composition to the patient on the first day or within three days prior to the first day, adipose tissue is obtained from the patient and processed to provide stromal vascular fraction used in the first injectable pharmaceutical composition and second injectable pharmaceutical composition that are intravenously administered to the patient on the first day.

Administration at or Near the Site of Pain

The methods may be further characterized according to characteristics of administrations, at or near the site of pain, of one or more doses of a third pharmaceutical composition. For example, in certain embodiments, the method further comprises the step of: administering to the patient by injection at or near the site of pain a dose of a third injectable pharmaceutical composition containing saline and an aliquot of stromal vascular fraction containing from 0.01 billion to about 1 billion cells. In certain embodiments, the third injectable pharmaceutical composition contains saline and an aliquot of stromal vascular fraction containing from 0.1 billion to about 0.5 billion cells. In certain embodiments, cells from the stromal vascular fraction are present in the third injectable pharmaceutical composition at a concentration of from about 1 million/mL to about 300 million/mL. In certain embodiments, cells from the stromal vascular fraction are present in the third injectable pharmaceutical composition at a concentration of from about 150 million/mL to about 300 million/mL. In certain embodiments, cells from the stromal vascular fraction are present in the third injectable pharmaceutical composition at a concentration of from about 200 million/mL to about 300 million/mL. In certain embodiments, cells from the stromal vascular fraction are present in the third injectable pharmaceutical composition at a concentration of from about 250 million/mL to about 350 million/mL.

Preferably, administrations, at or near the site of pain, of one or more doses of a third pharmaceutical composition is performed after intravenous administration of the first injectable pharmaceutical composition or second injectable pharmaceutical composition. Stems cells from the stromal vascular fraction administered at or near the site of pain, by administration of one or more doses of a third pharmaceutical composition have a greater propensity to stay at or near the site of pain when the third pharmaceutical composition is performed after intravenous administration of the first injectable pharmaceutical composition or second injectable pharmaceutical composition.

In certain embodiments, the third pharmaceutical composition is administered by injection into tissue at or near the site of pain.

In certain embodiments, the dose of third pharmaceutical composition in in the range of from about 0.5 mL to about 3 mL. In certain embodiments, the dose of third pharmaceutical composition in in the range of from about 1 mL to about 2 mL.

In certain embodiments, 1, 2, 3, 4, 5, 6, 7, 8, 9, 10, 11, 12, 13, 14, or 15 doses of third pharmaceutical composition are administered to the patient on one day. In certain embodiments, 1, 2, 3, or 4 doses of third pharmaceutical composition are administered to the patient on one day.

In certain embodiments, the third injectable pharmaceutical composition contains saline and an aliquot of stromal vascular fraction containing from about 5 million to about 0.2 billion cells. In certain embodiments, the third injectable pharmaceutical composition contains saline and an aliquot of stromal vascular fraction containing from about 5 million to about 1 billion cells. In certain embodiments, cells from the stromal vascular fraction are present in the third injectable pharmaceutical composition at a concentration of from about 5 million/mL to about 10 million/mL.

In certain embodiments, no greater than 50 mL of the third injectable pharmaceutical composition is administered to the patient on any one day. In certain embodiments, no greater than 40 mL of the third injectable pharmaceutical composition is administered to the patient on any one day. In certain embodiments, no greater than 20 mL of the third injectable pharmaceutical composition is administered to the patient on any one day. In certain embodiments, no greater than 10 mL of the third injectable pharmaceutical composition is administered to the patient on any one day.

In certain embodiments, no greater than 5 mL of the third injectable pharmaceutical composition is administered to any one location of the patient on any one day. In certain embodiments, no greater than 2 mL of the third injectable pharmaceutical composition is administered to any one location of the patient on any one day.

In certain embodiments, the third injectable pharmaceutical composition is administered to the patient on any one day in an amount of from about 0.1 mL to about 1 mL, from about 1 mL to about 2 mL, from about 2 mL to about 5 mL, from about 5 mL to about 10 mL, from about 10 mL to about 15 mL, from about 15 mL to about 25 mL, from about 25 mL to about 35 mL, or from about 35 mL to about 50 mL. In certain embodiments, the third injectable pharmaceutical composition is administered to the patient on any one day in an amount of from about 0.1 mL to about 1 mL, or from about 1 mL to about 2 mL.

In certain embodiments, a local anesthetic agent other than a caine analgesic is administered to the patient at the location(s) to receive the third injectable pharmaceutical composition prior to administering the third injectable pharmaceutical composition to the patient.

In certain embodiments, the method does not comprise a further step of: administering to the patient by injection at or near the site of pain a dose of a third injectable pharmaceutical composition containing saline and an aliquot of stromal vascular fraction.

Type of Pain to be Treated

The methods may be further characterized according to the type of pain to be treated. For example, in certain embodiments, the pain is chronic pain. In certain embodiments, the pain is acute pain. In certain embodiments, the pain is neuropathic pain. In certain embodiments, the pain is non-neuropathic pain.

In certain embodiments, the pain is joint pain. In certain embodiments, the pain is arthritic joint pain. In certain embodiments, the pain is osteoarthritic joint pain. In certain embodiments, the joint is a knee joint, ankle joint, hip joint, shoulder joint, elbow joint, wrist joint, or finger joint. In certain embodiments, the joint is a knee joint. In certain embodiments, the joint is an ankle joint. In certain embodiments, the joint is a hip joint. In certain embodiments, the joint is a shoulder joint. In certain embodiments, the joint is an elbow joint. In certain embodiments, the joint is a wrist joint. In certain embodiments, the joint is a finger joint.

In certain embodiments, the pain is pain due to lupus. In certain embodiments, the pain is pain due to fibromyalgia or chronic inflammatory demyelinating neuropathy. In certain embodiments, the pain is pain due to fibromyalgia. In certain embodiments, the pain is pain due to chronic inflammatory demyelinating neuropathy. In certain embodiments, the pain is pain due to arthritis.

In certain embodiments, the pain is nociceptive pain, inflammatory pain, or functional pain. In certain embodiments, the pain is nociceptive pain. In certain embodiments, the pain is inflammatory pain. In certain embodiments, the pain is functional pain.

Results Produced by the Methods

The methods may be further characterized according to the results produced by the methods. For example, in certain embodiments, the patient experiences at least a 25% reduction in pain within 9 months after the first day of the treatment method. In certain embodiments, the patient experiences at least a 50% reduction in pain within 9 months after the first day of the treatment method. In certain embodiments, the patient experiences at least a 25% reduction in pain within 1 month after the first day of the treatment method. In certain embodiments, the patient experiences at least a 50% reduction in pain within 1 month after the first day of the treatment method.

Reduction in pain experienced by the patient can be evaluated using procedures described in the literature, such as Patient Global Impression of Change (PGIC; change vs baseline in index knee on 7-point scale: 1=very much improved; 7=very much worse, with scores of 1 or 2 indicating significant improvement), Patient-specific Functional Scale (PSFS; rate ≤3 important activities difficult to perform due to index knee pain on 0-10 scale: 0=able to perform; 10=unable to perform), and the Western Ontario and McMaster Universities Osteoarthritis Index (WOMAC) B stiffness subscale and WOMAC C function subscale.

The methods may be further characterized according to the duration of reduction in pain. For example, in certain embodiments, the method is characterized by achieving a reduction in pain for a duration of at least 3 months. In certain embodiments, the method is characterized by achieving a reduction in pain for a duration of at least 4 months. In certain embodiments, the method is characterized by achieving a reduction in pain for a duration of at least 5 months. In certain embodiments, the method is characterized by achieving a reduction in pain for a duration of at least 6 months. In certain embodiments, the method is characterized by achieving a reduction in pain for a duration of at least 7 months. In certain embodiments, the method is characterized by achieving a reduction in pain for a duration of at least 8 months. In certain embodiments, the method is characterized by achieving a reduction in pain for a duration of at least 9 months. In certain embodiments, the method is characterized by achieving a reduction in pain for a duration of at least 10 months. In certain embodiments, the method is characterized by achieving a reduction in pain for a duration of at least 11 months. In certain embodiments, the method is characterized by achieving a reduction in pain for a duration of at least 12 months. In certain embodiments, the method is characterized by achieving a reduction in pain for a duration of 4 months to 6 months. In certain embodiments, the method is characterized by achieving a reduction in pain for a duration of 6 months to 9 months. In certain embodiments, the method is characterized by achieving a reduction in pain for a duration of 6 months to 12 months. In certain embodiments, the method is characterized by achieving a reduction in pain for a duration of 9 months to 12 months. In certain embodiments, the method is characterized by achieving a reduction in pain for a duration of 12 months to 18 months.

Third Method

Another aspect of the invention provides a method of treating pain, comprising intravenously administering to a patient in need thereof a stromal vascular fraction according to the following dosing schedule, in order to treat the pain:

a. on the first day:
  i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 4 billion cells;
b. on the day that is about 30 days after the first day:
  i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;
c. on the day that is about 60 days after the first day:
  i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 4 billion cells;
d. on the day that is about 90 days after the first day:
  i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 4 billion cells; and
e. on the day that is about 120 days after the first day:
  i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 4 billion cells;
wherein the stromal vascular fraction is derived from adipose tissue through sonication of lipoaspirate and without the use of an enzyme or sonication probe.

Fourth Method

Another aspect of the invention provides a method of treating pain, comprising intravenously administering to a patient in need thereof a stromal vascular fraction according to the following dosing schedule, in order to treat the pain:

a. on the first day:
  i. intravenously administer to the patient in need thereof a first injectable pharmaceutical composition containing saline and an aliquot of stromal vascular fraction; and thereafter
  ii. intravenously administer to the patient in need thereof a second injectable pharmaceutical composition containing saline and an aliquot of stromal vascular fraction;

b. on the day that is at least 5 days after the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction;

c. on the day that is at least 15 days after the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction;

d. on the day that is at least 30 days after the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction; and e. on the day that is at least 50 days after the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction.

In certain embodiments, step (b) is performed on a day that is at least 15 days after the first day. In certain embodiments, step (b) is performed on a day that is at least 30 days after the first day. In certain embodiments, step (b) is performed on a day that is at about 30 days after the first day. In certain embodiments, step (b) is performed on a day that is from about 20 days to about 40 days after the first day. In certain embodiments, step (c) is performed on a day that is at least 40 days after the first day. In certain embodiments, step (c) is performed on a day that is at least 50 days after the first day. In certain embodiments, step (c) is performed on a day that is at least 60 days after the first day. In certain embodiments, step (c) is performed on a day that is about 60 days after the first day. In certain embodiments, step (c) is performed on a day that is from about 45 days to about 75 days after the first day. In certain embodiments, step (d) is performed on a day that is at least 45 days after the first day. In certain embodiments, step (d) is performed on a day that is at least 65 days after the first day. In certain embodiments, step (d) is performed on a day that is at least 75 days after the first day. In certain embodiments, step (d) is performed on a day that is at least 90 days after the first day. In certain embodiments, step (d) is performed on a day that is about 90 days after the first day. In certain embodiments, step (d) is performed on a day that is from about 70 days to about 110 days after the first day. In certain embodiments, step (e) is performed on a day that is at least 80 days after the first day. In certain embodiments, step (e) is performed on a day that is at least 100 days after the first day. In certain embodiments, step (e) is performed on a day that is at least 120 days after the first day. In certain embodiments, step (e) is performed on a day that is about 120 days after the first day. In certain embodiments, step (e) is performed on a day that is from about 100 days to about 140 days after the first day.

In a more specific embodiment, the invention provides a method of treating pain, comprising intravenously administering to a patient in need thereof a stromal vascular fraction according to the following dosing schedule, in order to treat the pain:

a. on the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction;

b. on the day that is about 30 days after the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction;

c. on the day that is about 60 days after the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction;

d. on the day that is about 90 days after the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction; and e. on the day that is about 120 days after the first day:

i. intravenously administer to the patient in need thereof a first injectable pharmaceutical composition containing saline and an aliquot of stromal vascular fraction; and thereafter ii. intravenously administer to the patient in need thereof a second injectable pharmaceutical composition containing saline and an aliquot of stromal vascular fraction.

In certain embodiments, the stromal vascular fraction is derived from adipose tissue through sonication of lipoaspirate and without the use of an enzyme or sonication probe.

In certain embodiments, in step (a), the first injectable pharmaceutical composition is intravenously administered in less than about 70 minutes, 60 minutes, 50 minutes, 40 minutes, 30 minutes, 20 minutes, or 10 minutes. In certain embodiments, in step (a), the first injectable pharmaceutical composition is intravenously administered over from about 25 minutes to about 65 minutes, or from about 40 minutes to about 50 minutes. In certain embodiments, in step (a), the first injectable pharmaceutical composition is intravenously administered over about 45 minutes. In certain embodiments, in step (a), the second injectable pharmaceutical composition is intravenously administered in less than about 60 minutes, 50 minutes, 40 minutes, 30 minutes, 20 minutes, or 10 minutes. In certain embodiments, in step (a), the second injectable pharmaceutical composition is intravenously administered over from about 10 minutes to about 60 minutes, or from about 20 minutes to about 40 minutes. In certain embodiments, in step (a), the second injectable pharmaceutical composition is intravenously administered over about 30 minutes.

In certain embodiments, in step (b), the first injectable pharmaceutical composition is intravenously administered in less than about 70 minutes, 60 minutes, 50 minutes, 40 minutes, 30 minutes, 20 minutes, or 10 minutes. In certain embodiments, in step (b), the first injectable pharmaceutical composition is intravenously administered over from about 25 minutes to about 65 minutes, or from about 40 minutes to about 50 minutes. In certain embodiments, in step (b), the first injectable pharmaceutical composition is intravenously administered over about 45 minutes. In certain embodiments, in step (b), the second injectable pharmaceutical composition is intravenously administered in less than about 60 minutes, 50 minutes, 40 minutes, 30 minutes, 20 minutes, or 10 minutes. In certain embodiments, in step (b), the second injectable pharmaceutical composition is intravenously administered over from about 10 minutes to about 60 minutes, or from about 20 minutes to about 40 minutes. In certain embodiments, in step (b), the second injectable pharmaceutical composition is intravenously administered over about 30 minutes.

In certain embodiments, in step (c), the first injectable pharmaceutical composition is intravenously administered in less than about 70 minutes, 60 minutes, 50 minutes, 40 minutes, 30 minutes, 20 minutes, or 10 minutes. In certain embodiments, in step (c), the first injectable pharmaceutical composition is intravenously administered over from about 25 minutes to about 65 minutes, or from about 40 minutes to about 50 minutes. In certain embodiments, in step (c), the first injectable pharmaceutical composition is intravenously administered over about 45 minutes. In certain embodiments, in step (c), the second injectable pharmaceutical composition is intravenously administered in less than about 60 minutes, 50 minutes, 40 minutes, 30 minutes, 20 minutes, or 10 minutes. In certain embodiments, in step (c), the second injectable pharmaceutical composition is intravenously administered over from about 10 minutes to about 60 minutes, or from about 20 minutes to about 40 minutes. In certain embodiments, in step (c), the second injectable pharmaceutical composition is intravenously administered over about 30 minutes.

In certain embodiments, in step (d), the first injectable pharmaceutical composition is intravenously administered in less than about 70 minutes, 60 minutes, 50 minutes, 40 minutes, 30 minutes, 20 minutes, or 10 minutes. In certain embodiments, in step (d), the first injectable pharmaceutical composition is intravenously administered over from about 25 minutes to about 65 minutes, or from about 40 minutes to about 50 minutes. In certain embodiments, in step (d), the first injectable pharmaceutical composition is intravenously administered over about 45 minutes. In certain embodiments, in step (d), the second injectable pharmaceutical composition is intravenously administered in less than about 60 minutes, 50 minutes, 40 minutes, 30 minutes, 20 minutes, or 10 minutes. In certain embodiments, in step (d), the second injectable pharmaceutical composition is intravenously administered over from about 10 minutes to about 60 minutes, or from about 20 minutes to about 40 minutes. In certain embodiments, in step (d), the second injectable pharmaceutical composition is intravenously administered over about 30 minutes.

In certain embodiments, in step (e), the first injectable pharmaceutical composition is intravenously administered in less than about 70 minutes, 60 minutes, 50 minutes, 40 minutes, 30 minutes, 20 minutes, or 10 minutes. In certain embodiments, in step (e), the first injectable pharmaceutical composition is intravenously administered over from about 25 minutes to about 65 minutes, or from about 40 minutes to about 50 minutes. In certain embodiments, in step (e), the first injectable pharmaceutical composition is intravenously administered over about 45 minutes. In certain embodiments, in step (e), the second injectable pharmaceutical composition is intravenously administered in less than about 60 minutes, 50 minutes, 40 minutes, 30 minutes, 20 minutes, or 10 minutes. In certain embodiments, in step (e), the second injectable pharmaceutical composition is intravenously administered over from about 10 minutes to about 60 minutes, or from about 20 minutes to about 40 minutes. In certain embodiments, in step €, the second injectable pharmaceutical composition is intravenously administered over about 30 minutes.

In certain embodiments, the method comprises intravenously administering to a patient in need thereof a stromal vascular fraction according to the following dosing schedule, in order to treat the pain:

a. on the first day:

i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter ii. intravenously administer to the patient in need thereof over a duration of about 30 minutes a second injectable pharmaceutical composition containing saline an aliquot of stromal vascular fraction containing from about 0.2 billion to about 2 billion cells;

b. on the day that is about 30 days after the first day:

i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter ii. intravenously administer to the patient in need thereof over a duration of about 30 minutes a second injectable pharmaceutical composition containing saline and an aliquot of stromal vascular fraction containing from about 0.2 billion to about 2 billion cells;

c. on the day that is about 60 days after the first day:

i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter ii. intravenously administer to the patient in need thereof over a duration of about 30 minutes a second injectable pharmaceutical composition containing saline and an aliquot of stromal vascular fraction containing from about 0.2 billion to about 2 billion cells;

d. on the day that is about 90 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 2 billion cells; and e. on the day that is about 120 days after the first day:
  iii. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  iv. intravenously administer to the patient in need thereof over a duration of about 30 minutes a second injectable pharmaceutical composition containing saline and an aliquot of stromal vascular fraction containing from about 0.2 billion to about 2 billion cells;

wherein the stromal vascular fraction is derived from adipose tissue through sonication of lipoaspirate and without the use of an enzyme or sonication probe.

In certain embodiments, the method comprises intravenously administering to a patient in need thereof a stromal vascular fraction according to the following dosing schedule, in order to treat the pain:

a. on the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 2 billion cells;

b. on the day that is about 30 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 2 billion cells;

c. on the day that is about 60 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.2 billion to about 2 billion cells;

d. on the day that is about 90 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.2 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 2 billion cells; and e. on the day that is about 120 days after the first day:
  i. intravenously administer to the patient in need thereof over a duration of about 45 minutes an amount of about 200 mL of a first injectable pharmaceutical composition containing saline and an aliquot of stromal vascular fraction containing from about 0.1 billion to about 2 billion cells; and thereafter
  ii. intravenously administer to the patient in need thereof over a duration of about 30 minutes a second injectable pharmaceutical composition containing saline and an aliquot of stromal vascular fraction containing from about 0.1 billion to about 2 billion cells;

wherein the stromal vascular fraction is derived from adipose tissue through sonication of lipoaspirate and without the use of an enzyme or sonication probe.

In certain embodiments, the first injectable pharmaceutical composition contains saline and an aliquot of stromal vascular fraction containing from about 0.2 billion to about 2 billion cells. In certain embodiments, the second injectable pharmaceutical composition contains saline and an aliquot of stromal vascular fraction containing from about 0.2 billion to about 2 billion cells.

In certain embodiments, the first injectable pharmaceutical composition has a volume of from about 200 mL to about 350 mL. In certain embodiments, the first injectable pharmaceutical composition has a volume of from about 250 mL to about 350 mL. In certain embodiments, the second injectable pharmaceutical composition has a volume of about 150 mL to about 300 mL. In certain embodiments, the second injectable pharmaceutical composition has a volume of about 200 mL to about 300 mL. In certain embodiments, the second injectable pharmaceutical composition has a volume of about 200 mL to about 250 mL.

Additional Exemplary Features of the Third and Fourth Methods for Treating Pain

Additional exemplary features that may characterize the Third and Fourth Methods for Treating Pain described herein are provided below and include, for example, characteristics of the injectable pharmaceutical compositions, types of pain to be treated, and results produced by the methods. A more thorough description of such features is provided below. The invention embraces all permutations and combinations of these features.

Injectable Pharmaceutical Compositions

The methods may be further characterized according to characteristics of the injectable pharmaceutical compositions, such as the number of cells in the stromal vascular fraction in the injectable pharmaceutical compositions, the volume of saline in the injectable pharmaceutical compositions, and the total volume of the injectable pharmaceutical compositions. For example, in certain embodiments, the first injectable pharmaceutical composition contains saline and an aliquot of stromal vascular fraction containing from about 0.2 billion to about 0.8 billion cells. In certain embodiments, the first injectable pharmaceutical composition contains saline and an aliquot of stromal vascular fraction containing from about 0.2 billion to about 0.4 billion cells, from about 0.4 billion to about 0.6 billion cells, or from about 0.6 billion to about 0.8 billion cells. In certain embodiments, the second injectable pharmaceutical composition contains saline and an aliquot of stromal vascular fraction containing from about 0.5 billion to about 2.5 billion cells. In certain embodiments, the second injectable pharmaceutical composition contains saline and an aliquot of stromal vascular fraction containing from about 0.5 billion to about 1 billion cells, from about 1 billion to about 2 billion cells, or from about 2 billion to about 2.5 billion cells.

In certain embodiments, the first injectable pharmaceutical composition contains from about 380 mL to about 490 mL of saline. In certain embodiments, the first injectable pharmaceutical composition contains from about 150 mL to about 195 mL of saline. In certain embodiments, the second injectable pharmaceutical composition contains from about 180 mL to about 240 mL of saline.

In certain embodiments, the first injectable pharmaceutical composition has a volume of from about 400 mL to about 600 mL. In certain embodiments, the first injectable pharmaceutical composition has a volume of from about 180 mL to about 220 mL. In certain embodiments, the first injectable pharmaceutical composition has a volume of about 200 mL.

In certain embodiments, the second injectable pharmaceutical composition has a volume of about 150 mL to about 500 mL. In certain embodiments, the second injectable pharmaceutical composition has a volume of about 200 mL to about 450 mL. In certain embodiments, the second injectable pharmaceutical composition has a volume of about 250 mL to about 450 mL. In certain embodiments, the second injectable pharmaceutical composition has a volume of about 300 mL to about 420 mL. In certain embodiments, the second injectable pharmaceutical composition has a volume of about 300 mL to about 400 mL. In certain embodiments, the second injectable pharmaceutical composition has a volume of about 200 mL to about 300 mL. In certain embodiments, the second injectable pharmaceutical composition has a volume of about 150 mL to about 200 mL.

In certain embodiments, the first injectable pharmaceutical composition is intravenously administered at a rate of from about 2 to about 10 mL/min. In certain embodiments, the first injectable pharmaceutical composition is intravenously administered at a rate of from about 4 to about 6 mL/min. In certain embodiments, the first injectable pharmaceutical composition is intravenously administered at a rate of from about 4 to about 5 mL/min. In certain embodiments, the second injectable pharmaceutical composition is intravenously administered at a rate of from about 2 to about 10 mL/min. In certain embodiments, the second injectable pharmaceutical composition is intravenously administered at a rate of from about 4 to about 6 mL/min. In certain embodiments, the second injectable pharmaceutical composition is intravenously administered at a rate of from about 4 to about 5 mL/min. In certain embodiments, the second injectable pharmaceutical composition is intravenously administered at a rate of from about 4 to about 10 mL/min.

Additional Method Steps

The methods may be further characterized according to additional steps that the method further comprises. For example, in certain embodiments, the method further comprises intravenously administering saline to the patient prior to intravenously administering the first injectable pharmaceutical composition to the patient. In certain embodiments, the method further comprises intravenously administering at least about 25, 50, 75, 100, 125, or 150 mL of saline to the patient prior to intravenously administering the first injectable pharmaceutical composition to the patient. In certain embodiments, the method further comprises intravenously administering at least about 100 mL of saline to the patient prior to intravenously administering the first injectable pharmaceutical composition to the patient. In certain embodiments, the method further comprises intravenously administering about 100 mL of saline to the patient prior to intravenously administering the first injectable pharmaceutical composition to the patient. In certain embodiments, the method further comprises intravenously administering over a duration of about 25 minutes an amount of about 100 mL of saline to the patient prior to intravenously administering the first injectable pharmaceutical composition to the patient.

In certain embodiments, the method further comprises the step of: prior to intravenously administering the first injectable pharmaceutical composition to the patient on the first day, adipose tissue is obtained from the patient and processed to provide stromal vascular fraction used in the first injectable pharmaceutical composition and second injectable pharmaceutical composition that are intravenously administered to the patient on the first day.

In certain embodiments, the method further comprises the step of: prior to intravenously administering the first injectable pharmaceutical composition to the patient on the first day or within three days prior to the first day, adipose tissue is obtained from the patient and processed to provide stromal vascular fraction used in the first injectable pharmaceutical composition and second injectable pharmaceutical composition that are intravenously administered to the patient on the first day.

Administration at or Near the Site of Pain

The methods may be further characterized according to characteristics of administrations, at or near the site of pain, of one or more doses of a third pharmaceutical composition. For example, in certain embodiments, the method further comprises the step of: administering to the patient by injection at or near the site of pain a dose of a third injectable pharmaceutical composition containing saline and an aliquot of stromal vascular fraction containing from about 0.01 billion to about 1 billion cells. In certain embodiments, the third injectable pharmaceutical composition contains saline and an aliquot of stromal vascular fraction containing from about 0.1 billion to about 0.5 billion cells. In certain embodiments, cells from the stromal vascular fraction are present in the third injectable pharmaceutical composition at a concentration of from about 150 million/mL to about 300 million/mL. In certain embodiments, cells from the stromal vascular fraction are present in the third injectable pharmaceutical composition at a concentration of from about 1 million/mL to about 300 million/mL. In certain embodiments, cells from the stromal vascular fraction are present in the third injectable pharmaceutical composition at a concentration of from about 200 million/mL to about 300 million/mL. In certain embodiments, cells from the stromal vascular fraction are present in the third injectable pharmaceutical composition at a concentration of from about 250 million/mL to about 350 million/mL.

Preferably, administrations, at or near the site of pain, of one or more doses of a third pharmaceutical composition is performed after intravenous administration of the first injectable pharmaceutical composition or second injectable pharmaceutical composition. Stems cells from the stromal vascular fraction administered at or near the site of pain, by administration of one or more doses of a third pharmaceutical composition have a greater propensity to stay at or near the site of pain when the third pharmaceutical composition is performed after intravenous administration of the first injectable pharmaceutical composition or second injectable pharmaceutical composition.

In certain embodiments, the third pharmaceutical composition is administered by injection into tissue at or near the site of pain.

In certain embodiments, the dose of third pharmaceutical composition in in the range of from about 0.5 mL to about 3 mL. In certain embodiments, the dose of third pharmaceutical composition in in the range of from about 1 mL to about 2 mL.

In certain embodiments, 1, 2, 3, 4, 5, 6, 7, 8, 9, 10, 11, 12, 13, 14, or 15 doses of third pharmaceutical composition are administered to the patient on one day. In certain embodiments, 1, 2, 3, or 4 doses of third pharmaceutical composition are administered to the patient on one day.

In certain embodiments, the third injectable pharmaceutical composition contains saline and an aliquot of stromal vascular fraction containing from about 2 million to about 5 million cells. In certain embodiments, the third injectable pharmaceutical composition contains saline and an aliquot of stromal vascular fraction containing from about 2 million to about 5 million cells. In certain embodiments, cells from the stromal vascular fraction are present in the third injectable pharmaceutical composition at a concentration of from about 5 million/mL to about 10 million/mL.

In certain embodiments, no greater than 50 mL of the third injectable pharmaceutical composition is administered to the patient on any one day. In certain embodiments, no greater than 40 mL of the third injectable pharmaceutical composition is administered to the patient on any one day. In certain embodiments, no greater than 20 mL of the third injectable pharmaceutical composition is administered to the patient on any one day. In certain embodiments, no greater than 10 mL of the third injectable pharmaceutical composition is administered to the patient on any one day.

In certain embodiments, no greater than 5 mL of the third injectable pharmaceutical composition is administered to any one location of the patient on any one day. In certain embodiments, no greater than 2 mL of the third injectable pharmaceutical composition is administered to any one location of the patient on any one day.

In certain embodiments, the third injectable pharmaceutical composition is administered to the patient on any one day in an amount of from about 0.1 mL to about 1 mL, from about 1 mL to about 2 mL, from about 2 mL to about 5 mL, from about 5 mL to about 10 mL, from about 10 mL to about 15 mL, from about 15 mL to about 25 mL, from about 25 mL to about 35 mL, or from about 35 mL to about 50 mL.

In certain embodiments, a local anesthetic agent other than a caine analgesic is administered to the patient at the location(s) to receive the third injectable pharmaceutical composition prior to administering the third injectable pharmaceutical composition to the patient.

In certain embodiments, the method does not comprise a further step of: administering to the patient by injection at or near the site of pain a dose of a third injectable pharmaceutical composition containing saline and an aliquot of stromal vascular fraction.

Type of Pain to be Treated

The methods may be further characterized according to the type of pain to be treated. For example, in certain embodiments, the pain is chronic pain. In certain embodiments, the pain is acute pain. In certain embodiments, the pain is neuropathic pain. In certain embodiments, the pain is non-neuropathic pain.

In certain embodiments, the pain is neck pain. In certain embodiments, the pain is back pain.

In certain embodiments, the pain is nociceptive pain, inflammatory pain, or functional pain. In certain embodiments, the pain is nociceptive pain. In certain embodiments, the pain is inflammatory pain. In certain embodiments, the pain is functional pain.

Results Produced by the Methods

The methods may be further characterized according to the results produced by the methods. For example, in certain embodiments, the patient experiences at least a 25% reduction in pain within 6 months after the first day of the treatment method. In certain embodiments, the patient experiences at least a 50% reduction in pain within 6 months after the first day of the treatment method. In certain embodiments, the patient experiences at least a 25% reduction in pain within 1 month after the first day of the treatment method. In certain embodiments, the patient experiences at least a 50% reduction in pain within 1 month after the first day of the treatment method.

Reduction in pain experienced by the patient can be evaluated using procedures described in the literature, such as Patient Global Impression of Change (PGIC; change vs baseline in index knee on 7-point scale: 1=very much improved; 7=very much worse, with scores of 1 or 2 indicating significant improvement), Patient-specific Functional Scale (PSFS; rate ≤3 important activities difficult to perform due to index knee pain on 0-10 scale: 0=able to perform; 10=unable to perform), and the Western Ontario and McMaster Universities Osteoarthritis Index (WOMAC) B stiffness subscale and WOMAC C function subscale.

The methods may be further characterized according to the duration of reduction in pain. For example, in certain embodiments, the method is characterized by achieving a reduction in pain for a duration of at least 3 months. In certain embodiments, the method is characterized by achieving a reduction in pain for a duration of at least 4 months. In certain embodiments, the method is characterized by achieving a reduction in pain for a duration of at least 5 months. In certain embodiments, the method is characterized by achieving a reduction in pain for a duration of at least 6 months. In certain embodiments, the method is characterized by achieving a reduction in pain for a duration of at least 7 months. In certain embodiments, the method is characterized by achieving a reduction in pain for a duration of at least 8 months. In certain embodiments, the method is characterized by achieving a reduction in pain for a duration of at least 9 months. In certain embodiments, the method is characterized by achieving a reduction in pain for a duration of at least 10 months. In certain embodiments, the method is characterized by achieving a reduction in pain for a duration of at least 11 months. In certain embodiments, the method is characterized by achieving a reduction in pain for a duration of at least 12 months. In certain embodiments, the method is characterized by achieving a reduction in pain for a duration of 4 months to 6 months. In certain embodiments, the method is characterized by achieving a reduction in pain for a duration of 6 months to 9 months. In certain embodiments, the method is characterized by achieving a reduction in pain for a duration of 6 months to 12 months. In certain embodiments, the method is characterized by achieving a reduction in pain for a duration of 9 months to 12 months. In certain embodiments, the method is characterized by achieving a reduction in pain for a duration of 12 months to 18 months.

F. Methods for Treatment or Prophylaxis of a Coronavirus Infection

Another aspect of the invention provides methods for treatment or prophylaxis of a coronavirus infection. This is described in more detail below.

First Method

One aspect of the invention provides a method for the treatment or prophylaxis of a coronavirus infection in a patient, comprising intravenously administering to said patient in need thereof a stromal vascular fraction according to the following dosing schedule:

a. on the first day, intravenously administer to the patient in need thereof over a duration of about 35 minutes a first injectable pharmaceutical composition containing saline and an aliquot of stromal vascular fraction containing from about 0.7 billion to about 3 billion cells;

b. on the day after the first day, intravenously administer to the patient in need thereof over a duration of about 35 minutes a second injectable pharmaceutical composition containing saline and an aliquot of stromal vascular fraction containing from about 0.3 billion to about 2 billion cells;

c. on the second day after the first day, intravenously administer to the patient in need thereof over a duration of about 35 minutes a third injectable pharmaceutical composition containing saline and an aliquot of stromal vascular fraction containing from about 0.3 billion to about 2 billion cells; and d. on the third day after the first day, intravenously administer to the patient in need thereof over a duration of about 35 minutes a fourth injectable pharmaceutical composition containing saline and an aliquot of stromal vascular fraction containing from about 0.3 billion to about 2 billion cells;

wherein the stromal vascular fraction is derived from adipose tissue through sonication of lipoaspirate and without the use of an enzyme or sonication probe.

Second Method

Another aspect of the invention provides a method for the treatment or prophylaxis of a coronavirus infection in a patient, comprising intravenously administering to said patient in need thereof a stromal vascular fraction according to the following dosing schedule:

a. intravenously administer to the patient in need thereof a first injectable pharmaceutical composition containing saline and an aliquot of stromal vascular fraction; thereafter b. intravenously administer to the patient in need thereof a second injectable pharmaceutical composition containing saline and an aliquot of stromal vascular fraction; thereafter c. intravenously administer to the patient in need thereof a third injectable pharmaceutical composition containing saline and an aliquot of stromal vascular fraction; and thereafter d. intravenously administer to the patient in need thereof a fourth injectable pharmaceutical composition containing saline and an aliquot of stromal vascular fraction.

In certain embodiments, step (b) is performed at least one day after step (a). In certain embodiments, step (b) is performed one day after step (a). In certain embodiments, step (c) is performed at least one day after step (b). In certain embodiments, step (c) is performed one day after step (b). In certain embodiments, step (d) is performed at least one day after step (c). In certain embodiments, step (d) is performed one day after step (c).

In a more specific embodiment, the invention provides a method for the treatment or prophylaxis of a coronavirus infection in a patient, comprising intravenously administering to said patient in need thereof a stromal vascular fraction according to the following dosing schedule:

a. on the first day, intravenously administer to the patient in need thereof a first injectable pharmaceutical composition containing saline and an aliquot of stromal vascular fraction;

b. on the day after the first day, intravenously administer to the patient in need thereof a second injectable pharmaceutical composition containing saline and an aliquot of stromal vascular fraction;

c. on the second day after the first day, intravenously administer to the patient in need thereof a third injectable pharmaceutical composition containing saline and an aliquot of stromal vascular fraction; and d. on the third day after the first day, intravenously administer to the patient in need thereof a fourth injectable pharmaceutical composition containing saline and an aliquot of stromal vascular fraction.

In certain embodiments, the stromal vascular fraction is derived from adipose tissue through sonication of lipoaspirate and without the use of an enzyme or sonication probe.

In certain embodiments, in step (a), the injectable pharmaceutical composition is intravenously administered in less than about 60 minutes, 45 minutes, 35 minutes, 25 minutes, 15 minutes, or 10 minutes. In certain embodiments, in step (a), the injectable pharmaceutical composition is intravenously administered over from about 15 minutes to about 60 minutes, or from about 25 minutes to about 45 minutes. In certain embodiments, in step (a), the injectable pharmaceutical composition is intravenously administered over about 35 minutes.

In certain embodiments, in step (b), the injectable pharmaceutical composition is intravenously administered in less than about 60 minutes, 45 minutes, 35 minutes, 25 minutes, 15 minutes, or 10 minutes. In certain embodiments, in step (b), the injectable pharmaceutical composition is intravenously administered over from about 15 minutes to about 60 minutes, or from about 25 minutes to about 45 minutes. In certain embodiments, in step (b), the injectable pharmaceutical composition is intravenously administered over about 35 minutes.

In certain embodiments, in step (c), the injectable pharmaceutical composition is intravenously administered in less than about 60 minutes, 45 minutes, 35 minutes, 25 minutes, 15 minutes, or 10 minutes. In certain embodiments, in step (c), the injectable pharmaceutical composition is intravenously administered over from about 15 minutes to about 60 minutes, or from about 25 minutes to about 45 minutes. In certain embodiments, in step (c), the injectable pharmaceutical composition is intravenously administered over about 35 minutes.

In certain embodiments, in step (d), the injectable pharmaceutical composition is intravenously administered in less than about 60 minutes, 45 minutes, 35 minutes, 25 minutes, 15 minutes, or 10 minutes. In certain embodiments, in step (d), the injectable pharmaceutical composition is intravenously administered over from about 15 minutes to about 60 minutes, or from about 25 minutes to about 45 minutes. In certain embodiments, in step (d), the injectable pharmaceutical composition is intravenously administered over about 35 minutes.

Additional Exemplary Features of the First and Second Methods for Treatment or Prophylaxis of a Coronavirus Infection Additional exemplary features that may characterize the First and Second Methods for treatment or prophylaxis of a coronavirus infection described herein are provided below and include, for example, characteristics of the injectable pharmaceutical compositions, type of coronavirus infection, and results produced by the methods. A more thorough description of such features is provided below. The invention embraces all permutations and combinations of these features.

Injectable Pharmaceutical Compositions

The methods may be further characterized according to characteristics of the injectable pharmaceutical compositions, such as the number of cells in the stromal vascular fraction in the injectable pharmaceutical compositions, the volume of saline in the compositions, and the total volume of the injectable pharmaceutical compositions.

For example, in certain embodiments, the first injectable pharmaceutical composition contains saline and an aliquot of stromal vascular fraction containing from about 0.9 billion to about 1.5 billion cells. In certain embodiments, the second injectable pharmaceutical composition contains saline and an aliquot of stromal vascular fraction containing from about 0.4 billion to about 1 billion cells. In certain embodiments, the third injectable pharmaceutical composition contains saline and an aliquot of stromal vascular fraction containing from about 0.4 billion to about 1 billion cells. In certain embodiments, the fourth injectable pharmaceutical composition contains saline and an aliquot of stromal vascular fraction containing from about 0.4 billion to about 1 billion cells.

In certain embodiments, the first injectable pharmaceutical composition contains from about 240 mL to about 290 mL saline. In certain embodiments, the second injectable pharmaceutical composition contains from about 240 mL to about 290 mL saline. In certain embodiments, the third injectable pharmaceutical composition contains from about 240 mL to about 290 mL saline. In certain embodiments, the fourth injectable pharmaceutical composition contains from about 240 mL to about 290 mL saline.

In certain embodiments, the first injectable pharmaceutical composition has a volume of from about 330 mL to about 350 mL. In certain embodiments, the second injectable pharmaceutical composition has a volume of from about 290 mL to about 310 mL. In certain embodiments, the third injectable pharmaceutical composition has a volume of from about 290 mL to about 310 mL. In certain embodiments, the fourth injectable pharmaceutical composition has a volume of from about 290 mL to about 310 mL.

Additional Method Steps

The methods may be further characterized according to additional steps that the method further comprises. For example, in certain embodiments, the method further comprises the step of: prior to intravenously administering the first injectable pharmaceutical composition to the patient on the first day, adipose tissue is obtained from the patient and processed to provide stromal vascular fraction used in the first injectable pharmaceutical composition.

In certain embodiments, the method is characterized by the feature that saline is not intravenously administered to the patient immediately prior to intravenously administering the first injectable pharmaceutical composition. Intravenously administering the first injectable pharmaceutical composition to the patient at fast rate without immediately prior intravenous administration of saline results in a higher concentration of stem cells from the stromal vascular fraction in the patient's lungs.

Additional Features

In certain embodiments, the first injectable pharmaceutical composition contains saline and an aliquot of stromal vascular fraction containing from about 0.9 billion to about 1.5 billion cells. In certain embodiments, the second injectable pharmaceutical composition contains saline and an aliquot of stromal vascular fraction containing from about 0.4 billion to about 1 billion cells. In certain embodiments, the third injectable pharmaceutical composition contains saline and an aliquot of stromal vascular fraction containing from about 0.4 billion to about 1 billion cells. In certain embodiments, the fourth injectable pharmaceutical composition contains saline and an aliquot of stromal vascular fraction containing from about 0.4 billion to about 1 billion cells.

In certain embodiments, the first injectable pharmaceutical composition contains from about 240 mL to about 290 mL saline. In certain embodiments, the first injectable pharmaceutical composition has a volume of from about 330 mL to about 350 mL. In certain embodiments, the second injectable pharmaceutical composition contains from about 240 mL to about 290 mL saline. In certain embodiments, the second injectable pharmaceutical composition has a volume of from about 290 mL to about 310 mL. In certain embodiments, wherein the third injectable pharmaceutical composition contains from about 240 mL to about 290 mL saline. In certain embodiments, the third injectable pharmaceutical composition has a volume of from about 290 mL to about 310 mL. In certain embodiments, the fourth injectable pharmaceutical composition contains from about 240 mL to about 290 mL saline. In certain embodiments, the fourth injectable pharmaceutical composition has a volume of from about 290 mL to about 310 mL.

In certain embodiments, the method further comprises the step of: prior to intravenously administering the first injectable pharmaceutical composition to the patient on the first day, adipose tissue is obtained from the patient and processed to provide stromal vascular fraction used in the first injectable pharmaceutical composition.

In certain embodiments, the coronavirus infection is an infection by severe acute respiratory syndrome coronavirus 2 (SARS-CoV-2). In certain embodiments, the coronavirus infection is an infection by a variant of SARS-CoV-2. In certain embodiments, the coronavirus infection is an infection by a variant of SARS-CoV-2 having the spike protein of SARS-CoV-2. In certain embodiments, the coronavirus infection is an infection by SARS-CoV-2 or a variant thereof selected from B.1.617.2, Cluster 5, Lineage B.1.1.207, Lineage B.1.1.7, Variant of Concern 202102/02, Lineage B.1.1.317, Lineage B.1.1.318, Lineage B.1.351, Lineage B.1.429, Lineage B.1.525, Lineage P.1 (also known as Lineage B.1.1.28), D614G, E484K, N501Y, S477G/N, and P681H.

In certain embodiments, the patient suffers from cognitive impairment (e.g., brain fog) due to the coronavirus infection. In certain embodiments, the patient is immuno-compromised. In certain embodiments, the method improves immune function to thereby expedite recovery from a coronavirus infection. In certain embodiments, the method improves immune function to reduce the risk of contracting a coronavirus infection. In certain embodiments, the method enhances repair of patient tissue damaged by a coronavirus infection. In certain embodiments, the method enhances repair of patient tissue selected from lung tissue, kidney tissue, and pancreatic tissue damaged by a coronavirus infection. In certain embodiments, the method enhances repair of fibrotic tissue or scar tissue resulting from a coronavirus infection. In certain embodiments, the method treats the coronavirus infection.

G. Additional Exemplary Features of the Therapeutic Methods

Additional exemplary features that may characterize the Therapeutic Methods described herein are provided below and include, for example, features of the stromal vascular fraction and patients for treatment. A more thorough description of such features is provided below. The invention embraces all permutations and combinations of these features.

Stromal Vascular Fraction

Percent Viable Cells in the Stromal Vascular Fraction

The methods may be further characterized according to the percent of viable cells in the stromal vascular fraction. For example, in certain embodiments, at least 80% of cells in the aliquot of stromal vascular fraction are viable. In certain embodiments, at least 85% of cells in the aliquot of stromal vascular fraction are viable. In certain embodiments, at least 90% of cells in the aliquot of stromal vascular fraction are viable. In certain embodiments, at least 95% of cells in the aliquot of stromal vascular fraction are viable. In certain embodiments, at least 98% of cells in the aliquot of stromal vascular fraction are viable.

Viability of the cells may be measured using a commercially available flow-cytometer, such as flow-cytometers sold by Logos Biosystems.

Origin of the Stromal Vascular Fraction

The methods may be further characterized according to the origin of the stromal vascular fraction. For example, in certain embodiments, the stromal vascular fraction is autologous stromal vascular fraction. In certain embodiments, the stromal vascular fraction is derived from adipose tissue obtained from the abdomen of the patient. In certain embodiments, the stromal vascular fraction is derived from adipose tissue according to a procedure described herein.

Characteristics of the Stromal Vascular Fraction

The methods may be further characterized according to additional characteristics of the stromal vascular fraction. For example, in certain embodiments, the stromal vascular fraction comprises stem and other cells that express at least one protein selected from the group consisting of CD13, CD14, CD29, CD31, CD34, CD36, CD44, CD45, CD49d, CD54, CD58, CD71, CD73, CD90, CD105, CD106, CD151, and SH3. In certain embodiments, the stromal vascular fraction comprises stem and other cells that express at least one protein selected from the group consisting of CD13, CD29, CD34, CD36, CD44, CD49d, CD54, CD58, CD71, CD73, CD90, CD105, CD106, CD151, and SH3. In certain embodiments, the stromal vascular fraction comprises stem and other cells that express at least one protein selected from the group consisting of CD31, CD45, CD117, and CD146. In certain embodiments, the stromal vascular fraction may comprise stem and other cells that do not express CD56.

In certain embodiments, the stromal vascular fraction comprises stem and other cells that (i) express at least one protein selected from the group consisting of CD3, CD4, CD14, CD15, CD16, CD19, CD33, CD38, CD56, CD61, CD62e, CD62p, CD69, CD104, CD135, and CD144, and (ii) do not express any of CD3, CD4, CD14, CD15, CD16, CD19, CD33, CD38, CD56, CD61, CD62e, CD62p, CD69, CD104, CD135, and CD144. In certain embodiments, the stromal vascular fraction comprises stem cells and other cells that express CD49d, but do not express CD56.

In certain embodiments, the stromal vascular fraction comprises one or more of the following cell types: mesenchymal stem cells, hematopoietic cells, endothelial precursor cells (EPC), hematopoietic stem cells, platelets, Kupffer cells, osteoclasts, megakaryocytes, granulocytes, NK cells, endothelial precursor or progenitor cells, CD34+ cells, CD29+ cells, CD166+ cells, Thy-1+ or CD90+ stem cells, CD44+ cells, immune cells such as monocytes, leukocytes, lymphocytes, B and T cells, NK cells, macrophages, neutrophil leukocytes, neutrophils, neutrophil granulocytes, and the like including immune and other cells that express one or more of the following markers: CD3, CD14 (macrophage marker), CD19, CD20 (B cell marker), CD29 (integrin unit), CD31 (such as, endothelial, platelet, macrophage, Kupffer cell, granulocyte, T/NK cells, lymphocytes, megakaryocytes, osteoclasts, and neutrophils), CD44 (Hyaluronic acid receptor), CD45 (B and T cell marker), C56, CD73 (lymphocyte differentiation marker), and CD105.

In certain embodiments, the stromal vascular fraction comprises mesenchymal stem cells.

In certain embodiments, the stromal vascular fraction comprises cells expressing any of the markers disclosed in this application or any combination of these markers.

In certain embodiments, the stromal vascular fraction comprises adipose-derived stem cells that express at least one protein selected from the group consisting of CD13, CD29, CD31, CD34, CD36, CD44, CD45, CD49d, CD54, CD58, CD71, CD73, CD90, CD105, CD106, CD117, CD146, CD151, and SH3. In certain embodiments, the stromal vascular fraction comprises adipose-derived stem cells that express at least one protein selected from the group consisting of CD13, CD29, CD34, CD36, CD44, CD49d, CD54, CD58, CD71, CD73, CD90, CD105, CD106, CD151, and SH3. In certain embodiments, the stromal vascular fraction comprises adipose-derived stem cells that express at least one protein selected from the group consisting of CD31, CD45, CD117, and CD146.

In certain embodiments, the stromal vascular fraction comprises adipose-derived stem cells that (i) express at least one protein selected from the group consisting of CD13, CD29, CD31, CD34, CD36, CD44, CD45, CD49d, CD54, CD58, CD71, CD73, CD90, CD105, CD106, CD117, CD146, CD151, and SH3, and (ii) do not express CD56. In certain embodiments, the stromal vascular fraction comprises adipose-derived stem cells that (i) express at least one protein selected from the group consisting of CD13, CD29, CD34, CD36, CD44, CD49d, CD54, CD58, CD71, CD73, CD90, CD105, CD106, CD151, and SH3, and (ii) do not express CD56. In certain embodiments, the stromal vascular fraction comprises adipose-derived stem cells that (i) express at least one protein selected from the group consisting of CD31, CD45, CD117, and CD146, and (ii) do not express CD56.

In certain embodiments, the stromal vascular fraction comprises stem cells that express at least one protein selected from the group consisting of CD3, CD4, CD14, CD15, CD16, CD19, CD33, CD38, CD56, CD61, CD62e, CD62p, CD69, CD104, CD135, and CD144. In certain embodiment, the stromal vascular fraction comprises stem cells that do not express any of CD3, CD4, CD14, CD15, CD16, CD19, CD33, CD38, CD56, CD61, CD62e, CD62p, CD69, CD104, CD135, and CD144. In certain embodiments, the stromal vascular fraction comprises stem cells that express CD49d, and do not express CD56.

In certain embodiments, the stromal vascular fraction comprises cells having immunophenotype CD31, CD34, and CD45. In certain embodiments, the stromal vascular fraction comprises cells having immunophenotype CD31, CD34, CD45, and CD73.

In certain embodiments, the stromal vascular fraction comprises mesenchymal stem cells. In certain embodiments, at least 25% of cells in the stromal vascular fraction are mesenchymal stem cells. In certain embodiments, at least 1%, 2%, 3%, 4%, 5%, 6%, 7%, 8%, 9%, 10%, 15%, 20%, 25%, 30%, 35%, 40%, or 45% of cells in the stromal vascular fraction are mesenchymal stem cells. In certain embodiments, from about 10% to about 50% of cells in the stromal vascular fraction are mesenchymal stem cells. In certain embodiments, from about 30% to about 40% of cells in the stromal vascular fraction are mesenchymal stem cells. In certain embodiments, from about 10% to about 20%, from about 20% to about 30%, from about 30% to about 40%, from about 40% to about 50%, or from about 25% to about 25% of cells in the stromal vascular fraction are mesenchymal stem cells.

In certain embodiments, the stromal vascular fraction contains a cytokine.

Storage of Stromal Vascular Fraction

The methods may be further characterized according to storage of the stromal vascular fraction cells. For example, in certain embodiments, the stromal vascular fraction cells have not been stored prior to use. In certain embodiments, the stromal vascular fraction cells have not been stored at a temperature below 0° C. prior to use. In certain embodiments, the stromal vascular fraction cells have been stored prior to use in the method.

The stromal vascular fraction cells may be stored by any appropriate method known in the art (e.g., cryogenically frozen) and may be frozen at any temperature appropriate for storage of the cells. For example, in certain embodiments, the stromal vascular fraction cells have been frozen for storage. In certain embodiments, the stromal vascular fraction cells have been cryopreserved. In certain embodiments, the stromal vascular fraction cells have been frozen at about −20° C., about −80° C., about −120° C., about −130° C., about −135° C., about −140° C., about −150° C., about −160° C., about −170° C., about −180° C., about −190° C., or about −196° C. In certain embodiments, the stromal vascular fraction cells have been frozen at a temperature less than about −20° C., about −80° C., about −120° C., about −130° C., about −135° C., about −140° C., about −150° C., about −160° C., about −170° C., about −180° C., about −190° C., or about −196° C. In certain embodiments, the stromal vascular fraction cells have been frozen at any other temperature appropriate for storage of cells. In certain embodiments, the stromal vascular fraction cells are stored in appropriate containers and prepared for storage to reduce risk of cell damage and maximize the likelihood that the cells will survive thawing.

In certain embodiments, the stromal vascular fraction cells are stored at room temperature. In certain embodiments, the stromal vascular fraction cells are stored at a temperature below room temperature, but above freezing, for example, at about 4° C.

In certain embodiments, the stromal vascular fraction cells are harvested, washed in buffer or media, counted, concentrated (via centrifugation), formulated in freezing media (e.g., 90% FBS/10% DMSO), or any combination of these steps. In certain embodiments, prior to cryopreserving the stromal vascular fraction cells, the stromal vascular fraction cells are isolated, centrifuged, and resuspended in 10% DMSO/90% FBS solution, optionally at least about $10^4$ stromal vascular fraction cells per mL. In certain embodiments, the cryopreservation preparation comprising stromal vascular fraction cells may be substantially free of DMSO.

In certain embodiments, a cryopreserved stromal vascular fraction (SVF) cell preparations described herein comprises at least about 50,000-100,000 stromal vascular fraction cells. In certain embodiments, the cryopreserved SVF cell preparations comprise at least about 20,000-500,000 SVF cells. In certain embodiments, the cryopreserved SVF cell preparations comprise at least about 5,000, 10,000, 20,000, 30,000, 40,000, 50,000, 60,000, 75,000, 80,000, or 100,000 SVF cells. In certain embodiments, the cryopreserved SVF cell preparations comprise at least about 1,000, 2,000, 3,000, 4,000, 5,000, 10,000, 20,000, 30,000, 40,000, 50,000, 60,000, 75,000, 80,000, 100,000, or 500,000 SVF cells. In certain embodiments, the cryopreserved SVF cell preparations comprise at least about 1,000, 2,000, 3,000, 4,000, 5,000, 6,000, 7,000, 8,000, 9,000, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, or $9\times10^9$ SVF cells.

In certain embodiments, the cryopreserved SVF cell preparations are mammalian SVF cells. In certain embodiments, the cryopreserved SVF cell preparations are human SVF cells.

In certain embodiments, the cryopreserved SVF cell preparations comprise at least about 50,000-100,000 SVF cells/mL. In certain embodiments, the cryopreserved SVF cell preparations comprise at least about 20,000-500,000 SVF cells/mL. In certain embodiments, the cryopreserved SVF cell preparations comprise at least about 5,000, 10,000, 20,000, 30,000, 40,000, 50,000, 60,000, 75,000, 80,000, and 100,000 SVF cells/mL. In certain embodiments, the cryopreserved SVF cell preparations comprise at least about 1,000, 2,000, 3,000, 4,000, 5,000, 10,000, 20,000, 30,000, 40,000, 50,000, 60,000, 75,000, 80,000, 100,000, or 500,000 SVF cells/mL. In certain embodiments, the cryopreserved SVF cell preparations comprise at least about 1,000, 2,000, 3,000, 4,000, 5,000, 6,000, 7,000, 8,000, 9,000, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5 \times 10^9$, $6 \times 10^9$, $7 \times 10^9$, $8 \times 10^9$, or $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$ or $9 \times 10^{10}$ SVF cells/mL.

In certain embodiments, the SVF cells recovered from cryopreservation maintain their viability and differentiation status. In certain embodiments, at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the SVF cells retain viability and differentiation following cryopreservation. In certain embodiments, the SVF cells are cryopreserved and maintain their viability after being stored for at least about 1, 2, 3, 4, 5, 6, or 7 days. In certain embodiments, the SVF cells are cryopreserved and maintain their viability after being stored for at least about 1, 2, 3, 4, 5, 6, 7, 8, 9, 10, 11, or 12 months. In certain embodiments, the SVF cells are cryopreserved and maintain their viability after being stored for at least about 1, 2, 3, 4, 5, 6, or 7 years.

Patients for Treatment

The methods may be further characterized according to the patients for treatment. For example, in certain embodiments, the patient is a human. In certain embodiments, the patient is an adult human.

III. Preparation Stromal Vascular Fraction

Stromal vascular fraction used in the injectable pharmaceutical compositions can be prepared as generally described below.

Adipose tissue in a container is subjected to sonication, where the container is positioned in a sonicator device above a cup horn located in a water bath of a sonicator device. The water bath maintains a constant temperature, and the sonication is preferably performed using pulses of sonication separated by a plurality of rest periods. After sonication, contents of the container are mixed with saline, and the resulting mixture is subjected to centrifugation. After centrifugation, a plurality of cell pellets and plurality of buffy coat cell layers are isolated from the oily supernatant, to thereby produce the stromal vascular fraction.

The procedure can be further characterized according to features of the sonication. In certain embodiments, rest periods in the sonicating procedure are a minimum of a 10 seconds each after each one minute of sonication. In certain embodiments, the total time of sonication is approximately five minutes. In certain embodiments, sonication is performed at 70% to 90% amplitude of the sonicator device operating at 20 kHz.

The procedure can be further characterized according to features of the centrifugation. In certain embodiments, the centrifuging is performed for a duration of at least about three minutes. In certain embodiments, the centrifuging is performed for a duration of at least three minutes. In certain embodiments, the centrifuging is performed at 3000 rpm.

In certain embodiments, the plurality of cell pellets and plurality of buffy coat cell layers are subjected to filtration. In certain embodiments, the filtering is performed using a 60 μm filter.

In the step where, after sonication, the contents of the container are mixed with saline, the method may be further characterized according to the amount of saline added to the container. In certain embodiments, a volume of saline is added in an amount that is approximately equal to the volume of adipose tissue resulting from sonicating. In certain embodiments, a 25 mL aliquot of adipose tissue resulting from sonicating is mixed with a 25 mL aliquot of saline, and the resulting mixture is used in the centrifuging.

Preferably, the container containing adipose tissue is suspended above and not in contact with the cup horn located in the water bath of the sonicator device. In certain embodiments, the container is placed into an adapter that maintains the container above and not in contact with the cup horn located in in the water bath of the sonicator device. In certain embodiments, the container is maintained at least 3 mm above the cup horn.

The procedure can be further characterized according to features of the sonication device. In certain embodiments, the water bath is maintained at about 200 Celsius. In certain embodiments, the water bath is maintained at 20° Celsius. Preferably, there is no sonicating probe in contact with the adipose tissue. In certain embodiments, the container is a sonication bottle capable of holding at least 150 mL.

The procedure for obtaining stromal vascular fraction from adipose tissue may be more specifically described by the following procedure:

a bottle containing adipose tissue is placed in a sonicator device above a cup horn located in a water bath of the sonicator device, wherein the bottle has capacity to contain 150 mL of adipose tissue and the water bath is maintained at a constant temperature;

adipose tissue in the container is sonicated with pulsing, the pulsing created by interjecting a plurality of rests, wherein the sonicator device operates at 70% to 90% amplitude of the sonicator device operating at 20 kHz;

adipose tissue resulting from sonication is mixed with saline, and the resulting mixture is subjected to centrifugation for at least three minutes at 3000 rpm;

the oily supernatant in the mixture resulting from centrifugation is discarded to leave a mixture of cell pellets and buffy coat cell layers; and the mixture of cell pellets and buffy coat cell layers is filtered, to thereby produce the stromal vascular fraction.

The procedure may be more specifically described according to one or more of the following features:

rests in the sonicating step are a minimum of a 10 seconds each after each minute of sonicating, where the total sonication time is about five minutes;

filtering is performed using a 60 μm filter;

the saline is mixed at an equal volume to the adipose tissue resulting from sonicating;

the bottle containing adipose tissue is suspended at least 3 mm above and not in contact with the cup horn located in the water bath of the sonicator device;

the water bath is maintained at a temperature of 200 Celsius.

sonicating adipose tissue in the bottle is performed without a sonicating probe in contact with the adipose tissue.

Therapeutic methods described herein can be further characterized according to the procedure used to obtain stromal vascular fraction that is used in the therapeutic method, such as the stromal vascular fraction present in the injectable pharmaceutical composition.

IV. Exemplary Embodiments

Exemplary embodiments are recited below:

1. A method of treating a pulmonary disorder, comprising intravenously administering to a patient in need thereof a stromal vascular fraction according to the following dosing schedule, in order to treat the pulmonary disorder:

a. on the first day, intravenously administer to the patient in need thereof over a duration of about 35 minutes a first injectable pharmaceutical composition containing saline and an aliquot of stromal vascular fraction containing from about 0.7 billion to about 3 billion cells;

b. on the day after the first day, intravenously administer to the patient in need thereof over a duration of about 35 minutes a second injectable pharmaceutical composition containing saline and an aliquot of stromal vascular fraction containing from about 0.3 billion to about 2 billion cells;

c. on the second day after the first day, intravenously administer to the patient in need thereof over a duration of about 35 minutes a third injectable pharmaceutical composition containing saline and an aliquot of stromal vascular fraction containing from about 0.3 billion to about 2 billion cells; and d. on the third day after the first day, intravenously administer to the patient in need thereof over a duration of about 35 minutes a fourth injectable pharmaceutical composition containing saline and an aliquot of stromal vascular fraction containing from about 0.3 billion to about 2 billion cells;

wherein the stromal vascular fraction is derived from adipose tissue through sonication of lipoaspirate and without the use of an enzyme or sonication probe.

2. The method of Embodiment 1, wherein the first injectable pharmaceutical composition contains saline and an aliquot of stromal vascular fraction containing from about 0.9 billion to about 1.5 billion cells.

3. The method of Embodiment 1 or 2, wherein the second injectable pharmaceutical composition contains saline and an aliquot of stromal vascular fraction containing from about 0.4 billion to about 1 billion cells.

4. The method of any one of Embodiments 1-3, wherein the third injectable pharmaceutical composition contains saline and an aliquot of stromal vascular fraction containing from about 0.4 billion to about 1 billion cells.

5. The method of any one of Embodiments 1-4, wherein the fourth injectable pharmaceutical composition contains saline and an aliquot of stromal vascular fraction containing from about 0.4 billion to about 1 billion cells.

6. The method of any one of Embodiments 1-5, wherein the first injectable pharmaceutical composition contains from about 240 mL to about 290 mL saline.

7. The method of any one of Embodiments 1-6, wherein the first injectable pharmaceutical composition has a volume of from about 330 mL to about 350 mL.

8. The method of any one of Embodiments 1-7, wherein the second injectable pharmaceutical composition contains from about 240 mL to about 290 mL saline.

9. The method of any one of Embodiments 1-8, wherein the second injectable pharmaceutical composition has a volume of from about 290 mL to about 310 mL.

10. The method of any one of Embodiments 1-9, wherein the third injectable pharmaceutical composition contains from about 240 mL to about 290 mL saline.

11. The method of any one of Embodiments 1-10, wherein the third injectable pharmaceutical composition has a volume of from about 290 mL to about 310 mL.

12. The method of any one of Embodiments 1-11, wherein the fourth injectable pharmaceutical composition contains from about 240 mL to about 290 mL saline.

13. The method of any one of Embodiments 1-12, wherein the fourth injectable pharmaceutical composition has a volume of from about 290 mL to about 310 mL.

14. The method of any one of Embodiments 1-13, further comprising the step of: prior to intravenously administering the first injectable pharmaceutical composition to the patient on the first day, adipose tissue is obtained from the patient and processed to provide stromal vascular fraction used in the first injectable pharmaceutical composition.

15. The method of any one of Embodiments 1-14, wherein the pulmonary disorder is chronic obstructive pulmonary disease.

16. The method of any one of Embodiments 1-14, wherein the pulmonary disorder is asthma.

17. The method of any one of Embodiments 1-14, wherein the pulmonary disorder is bronchitis.

18. The method of any one of Embodiments 1-14, wherein the pulmonary disorder is chronic bronchitis.

19. The method of any one of Embodiments 1-14, wherein the pulmonary disorder is emphysema.

20. The method of any one of Embodiments 1-14, wherein the pulmonary disorder is acute respiratory distress syndrome.

21. The method of any one of Embodiments 1-14, wherein the pulmonary disorder is an infection by a coronavirus.

22. The method of any one of Embodiments 1-14, wherein the pulmonary disorder is an infection by severe acute respiratory syndrome coronavirus 2 (SARS-CoV-2).

23. The method of any one of Embodiments 1-14, wherein the pulmonary disorder is pneumonia or pleural effusion.

24. The method of any one of Embodiments 1-23, wherein the patient experiences at least a 25% reduction in symptoms from the pulmonary disorder within 1 week after the first day of the treatment method.

25. The method of any one of Embodiments 1-23, wherein the patient experiences at least a 50% reduction in symptoms from the pulmonary disorder within 1 week after the first day of the treatment method.

26. A method of treating a neurodegenerative disorder, comprising intravenously administering to a patient in need thereof a stromal vascular fraction according to the following dosing schedule, in order to treat the neurodegenerative disorder:

a. on the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

b. on the day that is about 30 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of from about 0.2 billion to about 4 billion cells; and c. on the day that is about 60 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter

73 ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

27. The method of Embodiment 26, wherein the first injectable pharmaceutical composition contains saline and an aliquot of stromal vascular fraction containing from about 0.2 billion to about 0.8 billion cells.

28. The method of Embodiment 26 or 27, wherein the second injectable pharmaceutical composition contains saline and an aliquot of stromal vascular fraction containing from about 0.5 billion to about 2.5 billion cells.

29. The method of any one of Embodiments 26-28, wherein the first injectable pharmaceutical composition is intravenously administered at a rate of from about 4 to about 6 mL/min.

30. The method of any one of Embodiments 26-29, wherein the first injectable pharmaceutical composition has a volume of about 200 mL.

31. The method of any one of Embodiments 26-30, wherein the second injectable pharmaceutical composition is intravenously administered at a rate of from about 4 to about 6 mL/min.

32. The method of any one of Embodiments 26-31, wherein the second injectable pharmaceutical composition has a volume of about 200 mL to about 450 mL.

33. The method of any one of Embodiments 26-32, further comprising intravenously administering at least about 100 mL of saline to the patient prior to intravenously administering the first injectable pharmaceutical composition to the patient.

34. The method of any one of Embodiments 26-32, further comprising intravenously administering over a duration of about 25 minutes an amount of about 100 mL of saline to the patient prior to intravenously administering the first injectable pharmaceutical composition to the patient.

35. The method of any one of Embodiments 26-34, further comprising the step of: prior to intravenously administering the first injectable pharmaceutical composition to the patient on the first day, adipose tissue is obtained from the patient and processed to provide stromal vascular fraction used in the first injectable pharmaceutical composition and second injectable pharmaceutical composition that are intravenously administered to the patient on the first day.

36. The method of any one of Embodiments 26-34, further comprising the step of: prior to intravenously administering the first injectable pharmaceutical composition to the patient on the first day or within three days prior to the first day adipose tissue is obtained from the patient and processed to provide stromal vascular fraction used in the first injectable pharmaceutical composition and second injectable pharmaceutical composition that are intravenously administered to the patient on the first day.

37. The method of any one of Embodiments 26-36, wherein the neurodegenerative disorder is multiple sclerosis.

38. The method of any one of Embodiments 26-36, wherein the neurodegenerative disorder is amyotrophic lateral sclerosis.

39. The method of any one of Embodiments 26-36, wherein the neurodegenerative disorder is dementia.

40. The method of any one of Embodiments 26-36, wherein the neurodegenerative disorder is Parkinson's Disease.

41. The method of any one of Embodiments 26-40, wherein the patient experiences at least a 25% reduction in symptoms from the neurodegenerative disorder within 3 months after the first day of the treatment method.

42. The method of any one of Embodiments 26-40, wherein the patient experiences at least a 50% reduction in symptoms from the neurodegenerative disorder within 3 months after the first day of the treatment method.

43. A method of treating a disorder selected from the group consisting of a brain injury and a psychiatric disorder, comprising intravenously administering to a patient in need thereof a stromal vascular fraction according to the following dosing schedule, in order to treat the disorder:

a. on the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

b. on the day that is about 30 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells; and c. on the day that is about 60 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

44. The method of Embodiment 43, wherein the first injectable pharmaceutical composition contains saline and an aliquot of stromal vascular fraction containing from about 0.2 billion to about 0.8 billion cells.

45. The method of Embodiment 43 or 44, wherein the second injectable pharmaceutical composition contains saline and an aliquot of stromal vascular fraction containing from about 0.5 billion to about 2.5 billion cells.

46. The method of any one of Embodiments 43-45, wherein the first injectable pharmaceutical composition is intravenously administered at a rate of from about 4 to about 6 mL/min.

47. The method of any one of Embodiments 43-46, wherein the first injectable pharmaceutical composition has a volume of about 200 mL.

48. The method of any one of Embodiments 43-47, wherein the second injectable pharmaceutical composition is intravenously administered at a rate of from about 4 to about 6 mL/min.

49. The method of any one of Embodiments 43-48, wherein the second injectable pharmaceutical composition has a volume of about 200 mL to about 450 mL.

50. The method of any one of Embodiments 43-49, further comprising intravenously administering at least about 100 mL of saline to the patient prior to intravenously administering the first injectable pharmaceutical composition to the patient.

51. The method of any one of Embodiments 43-49, further comprising intravenously administering over a duration of about 25 minutes an amount of about 100 mL of saline to the patient prior to intravenously administering the first injectable pharmaceutical composition to the patient.

52. The method of any one of Embodiments 43-51, further comprising the step of: prior to intravenously administering the first injectable pharmaceutical composition to the patient on the first day, adipose tissue is obtained from the patient and processed to provide stromal vascular fraction used in the first injectable pharmaceutical composition and second injectable pharmaceutical composition that are intravenously administered to the patient on the first day.

53. The method of any one of Embodiments 43-51, further comprising the step of: prior to intravenously administering the first injectable pharmaceutical composition to the patient on the first day or within three days prior to the first day, adipose tissue is obtained from the patient and processed to provide stromal vascular fraction used in the first injectable pharmaceutical composition and second injectable pharmaceutical composition that are intravenously administered to the patient on the first day.

54. The method of any one of Embodiments 43-53, wherein the disorder is a brain injury.

55. The method of any one of Embodiments 43-53, wherein the disorder is a stroke.

56. The method of any one of Embodiments 43-53, wherein the disorder is chronic traumatic encephalopathy.

57. The method of any one of Embodiments 43-53, wherein the disorder is traumatic brain injury.

58. The method of any one of Embodiments 43-53, wherein the disorder is a psychiatric disorder.

59. The method of any one of Embodiments 43-53, wherein the disorder is post-traumatic stress disorder.

60. The method of any one of Embodiments 43-53, wherein the disorder is anxiety.

61. The method of any one of Embodiments 43-53, wherein the disorder is post-concussion syndrome.

62. The method of any one of Embodiments 43-61, wherein the patient experiences at least a 25% reduction in symptoms from the disorder within 3 months after the first day of the treatment method.

63. The method of any one of Embodiments 43-61, wherein the patient experiences at least a 50% reduction in symptoms from the disorder within 3 months after the first day of the treatment method.

64. A method of treating a metabolic disorder, comprising intravenously administering to a patient in need thereof a stromal vascular fraction according to the following dosing schedule, in order to treat the metabolic disorder:

a. on the first day:

i. intravenously administer to the patient in need thereof over a duration of about 45 minutes of a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

b. on the day that is about 14 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

c. on the day that is about 35 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

d. on the day that is about 65 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells; and e. on the day that is about 95 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

65. The method of Embodiment 64, wherein the first injectable pharmaceutical composition contains saline and an aliquot of stromal vascular fraction containing from about 0.2 billion to about 0.8 billion cells.

66. The method of Embodiment 64 or 65, wherein the second injectable pharmaceutical composition contains saline and an aliquot of stromal vascular fraction containing from about 0.5 billion to about 2.5 billion cells.

67. The method of any one of Embodiments 64-66, wherein the first injectable pharmaceutical composition is intravenously administered at a rate of from about 4 to about 6 mL/min.

68. The method of any one of Embodiments 64-67, wherein the first injectable pharmaceutical composition has a volume of about 200 mL.

69. The method of any one of Embodiments 64-68, wherein the second injectable pharmaceutical composition is intravenously administered at a rate of from about 4 to about 6 mL/min.

70. The method of any one of Embodiments 64-69, wherein the second injectable pharmaceutical composition has a volume of about 200 mL to about 450 mL.

71. The method of any one of Embodiments 64-70, further comprising intravenously administering at least about 100 mL of saline to the patient prior to intravenously administering the first injectable pharmaceutical composition to the patient.

72. The method of any one of Embodiments 64-70, further comprising intravenously administering over a duration of about 25 minutes an amount of about 100 mL of saline to the patient prior to intravenously administering the first injectable pharmaceutical composition to the patient.

73. The method of any one of Embodiments 64-72, further comprising the step of: prior to intravenously administering the first injectable pharmaceutical composition to the patient on the first day, adipose tissue is obtained from the patient and processed to provide stromal vascular fraction used in the first injectable pharmaceutical composition and second injectable pharmaceutical composition that are intravenously administered to the patient on the first day.

74. The method of any one of Embodiments 64-72, further comprising the step of: prior to intravenously administering the first injectable pharmaceutical composition to the patient on the first day or within three days prior to the first day, adipose tissue is obtained from the patient and processed to provide stromal vascular fraction used in the first injectable pharmaceutical composition and second injectable pharmaceutical composition that are intravenously administered to the patient on the first day.

75. The method of any one of Embodiments 64-74, wherein the metabolic disorder is diabetes mellitus.

76. The method of any one of Embodiments 64-74, wherein the metabolic disorder is type I diabetes, type 2 diabetes, or metabolic syndrome.

77. The method of any one of Embodiments 64-76, wherein the patient experiences at least a 25% reduction in symptoms from the disorder within 4 months after the first day of the treatment method.

78. The method of any one of Embodiments 64-76, wherein the patient experiences at least a 50% reduction in symptoms from the disorder within 4 months after the first day of the treatment method.

79. A method of treating pain, comprising intravenously administering to a patient in need thereof a stromal vascular fraction according to the following dosing schedule, in order to treat the pain:

a. on the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

b. on the day that is about 90 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells; and c. on the day that is about 210 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

80. The method of Embodiment 79, wherein the first injectable pharmaceutical composition contains saline and an aliquot of stromal vascular fraction containing from about 0.2 billion to about 0.8 billion cells.

81. The method of Embodiment 79 or 80, wherein the second injectable pharmaceutical composition contains saline and an aliquot of stromal vascular fraction containing from about 0.5 billion to about 2.5 billion cells.

82. The method of any one of Embodiments 79-81, wherein the first injectable pharmaceutical composition is intravenously administered at a rate of from about 4 to about 6 mL/min.

83. The method of any one of Embodiments 79-82, wherein the first injectable pharmaceutical composition has a volume of about 200 mL.

84. The method of any one of Embodiments 79-83, wherein the second injectable pharmaceutical composition is intravenously administered at a rate of from about 4 to about 6 mL/min.

85. The method of any one of Embodiments 79-84, wherein the second injectable pharmaceutical composition has a volume of about 200 mL to about 450 mL.

86. The method of any one of Embodiments 79-85, further comprising intravenously administering at least about 100 mL of saline to the patient prior to intravenously administering the first injectable pharmaceutical composition to the patient.

87. The method of any one of Embodiments 79-85, further comprising intravenously administering over a duration of about 25 minutes an amount of about 100 mL of saline to the patient prior to intravenously administering the first injectable pharmaceutical composition to the patient.

88. The method of any one of Embodiments 79-87, further comprising the step of: prior to intravenously administering the first injectable pharmaceutical composition to the patient on the first day, adipose tissue is obtained from the patient and processed to provide stromal vascular fraction used in the first injectable pharmaceutical composition and second injectable pharmaceutical composition that are intravenously administered to the patient on the first day.

89. The method of any one of Embodiments 79-87, further comprising the step of: prior to intravenously administering the first injectable pharmaceutical composition to the patient on the first day or within three days prior to the first day, adipose tissue is obtained from the patient and processed to provide stromal vascular fraction used in the first injectable pharmaceutical composition and second injectable pharmaceutical composition that are intravenously administered to the patient on the first day.

90. The method of any one of Embodiments 79-89, further comprising the step of: administering to the patient by injection at or near the site of pain a dose of a third injectable pharmaceutical composition containing saline and an aliquot of stromal vascular fraction containing from about 0.2 billion to about 0.8 billion cells.

91. Embodiment 90, wherein the third injectable pharmaceutical composition contains saline and an aliquot of stromal vascular fraction containing from about 0.5 billion to about 2.5 billion cells.

92. Embodiment 90 or 91, wherein cells from the stromal vascular fraction are present in the third injectable pharmaceutical composition at a concentration of from about 1 million/mL to about 10 million/mL.

93. The method of any one of Embodiments 90-92, wherein no greater than 50 mL of the third injectable pharmaceutical composition is administered to the patient on any one day.

94. The method of any one of Embodiments 90-92, wherein no greater than 40 mL of the third injectable pharmaceutical composition is administered to the patient on any one day.

95. The method of any one of Embodiments 90-92, wherein no greater than 20 mL of the third injectable pharmaceutical composition is administered to the patient on any one day.

96. The method of any one of Embodiments 90-92, wherein no greater than 10 mL of the third injectable pharmaceutical composition is administered to the patient on any one day.

97. The method of any one of Embodiments 90-96, wherein no greater than 5 mL of the third injectable pharmaceutical composition is administered to any one location of the patient on any one day.

98. The method of any one of Embodiments 90-96, wherein no greater than 2 mL of the third injectable pharmaceutical composition is administered to any one location of the patient on any one day.

99. The method of any one of Embodiments 90-98, wherein a local anesthetic agent other than a caine analgesic is administered to the patient at the location(s) to receive the third injectable pharmaceutical composition prior to administering the third injectable pharmaceutical composition to the patient.

100. The method of any one of Embodiments 79-99, wherein the pain is chronic pain.

101. The method of any one of Embodiments 79-99, wherein the pain is acute pain.

102. The method of any one of Embodiments 79-99, wherein the pain is neuropathic pain.

103. The method of any one of Embodiments 79-99, wherein the pain is non-neuropathic pain.

104. The method of any one of Embodiments 79-99, wherein the pain is joint pain.

105. The method of any one of Embodiments 79-99, wherein the pain is arthritic joint pain.

106. The method of any one of Embodiments 79-99, wherein the pain is osteoarthritic joint pain.

107. The method of any one of Embodiments 103-106, wherein the joint is a knee joint, ankle joint, hip joint, shoulder joint, elbow joint, wrist joint, or finger joint.

108. The method of any one of Embodiments 79-99, wherein the pain is pain due to lupus.

109. The method of any one of Embodiments 79-99, wherein the pain is pain due to fibromyalgia or chronic inflammatory demyelinating neuropathy.

110. The method of any one of Embodiments 79-99, wherein the pain is pain due to arthritis.

111. The method of any one of Embodiments 79-99, wherein the pain is nociceptive pain, inflammatory pain, or functional pain.

112. The method of any one of Embodiments 79-111, wherein the patient experiences at least a 25% reduction in pain within 9 months after the first day of the treatment method.

113. The method of any one of Embodiments 79-111, wherein the patient experiences at least a 50% reduction in pain within 9 months after the first day of the treatment method.

114. A method of treating pain, comprising intravenously administering to a patient in need thereof a stromal vascular fraction according to the following dosing schedule, in order to treat the pain:
   a. on the first day:
      i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter
      ii. intravenously administer to the patient in need thereof over a duration of about 30 minutes a second injectable pharmaceutical composition containing saline an aliquot of stromal vascular fraction containing from about 0.2 billion to about 4 billion cells;

b. on the day that is about 30 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

c. on the day that is about 60 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

d. on the day that is about 90 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells; and e. on the day that is about 120 days after the first day:

i. intravenously administer to the patient in need thereof over a duration of about 45 minutes a first injectable pharmaceutical composition containing saline and an aliquot of stromal vascular fraction containing from about 0.2 billion to about 1.5 billion cells; and thereafter ii. intravenously administer to the patient in need thereof over a duration of about 30 minutes a second injectable pharmaceutical composition containing saline and an aliquot of stromal vascular fraction containing from about 0.2 billion to about 4 billion cells;

wherein the stromal vascular fraction is derived from adipose tissue through sonication of lipoaspirate and without the use of an enzyme or sonication probe.

115. The method of Embodiment 114, wherein the first injectable pharmaceutical composition contains saline and an aliquot of stromal vascular fraction containing from about 0.2 billion to about 0.8 billion cells.

116. The method of Embodiment 114 or 115, wherein the second injectable pharmaceutical composition contains saline and an aliquot of stromal vascular fraction containing from about 0.5 billion to about 2.5 billion cells.

117. The method of any one of Embodiments 114-116, wherein the first injectable pharmaceutical composition is intravenously administered at a rate of from about 4 to about 6 mL/min.

118. The method of any one of Embodiments 114-117, wherein the first injectable pharmaceutical composition has a volume of about 200 mL.

119. The method of any one of Embodiments 114-118, wherein the second injectable pharmaceutical composition is intravenously administered at a rate of from about 4 to about 6 mL/min.

120. The method of any one of Embodiments 114-119, wherein the second injectable pharmaceutical composition has a volume of about 200 mL to about 450 mL.

121. The method of any one of Embodiments 114-120, further comprising intravenously administering at least about 100 mL of saline to the patient prior to intravenously administering the first injectable pharmaceutical composition to the patient.

122. The method of any one of Embodiments 114-120, further comprising intravenously administering over a duration of about 25 minutes an amount of about 100 mL of saline to the patient prior to intravenously administering the first injectable pharmaceutical composition to the patient.

123. The method of any one of Embodiments 114-122, further comprising the step of: prior to intravenously administering the first injectable pharmaceutical composition to the patient on the first day, adipose tissue is obtained from the patient and processed to provide stromal vascular fraction used in the first injectable pharmaceutical composition and second injectable pharmaceutical composition that are intravenously administered to the patient on the first day.

124. The method of any one of Embodiments 114-122, further comprising the step of: prior to intravenously administering the first injectable pharmaceutical composition to the patient on the first day or within three days prior to the first day, adipose tissue is obtained from the patient and processed to provide stromal vascular fraction used in the first injectable pharmaceutical composition and second injectable pharmaceutical composition that are intravenously administered to the patient on the first day.

125. The method of any one of Embodiments 114-124, further comprising the step of: administering to the patient by injection at or near the site of pain a dose of a third injectable pharmaceutical composition containing saline and an aliquot of stromal vascular fraction containing from about 0.01 billion to about 1 billion cells.

126. Embodiment 125, wherein the third injectable pharmaceutical composition contains saline and an aliquot of stromal vascular fraction containing from about 0.1 billion to about 0.5 billion cells.

127. The method of any one of Embodiments 125 or 126, cells from the stromal vascular fraction are present in the third injectable pharmaceutical composition at a concentration of from about 1 million/mL to about 300 million/mL.

128. The method of any one of Embodiments 125-127, wherein no greater than 50 mL of the third injectable pharmaceutical composition is administered to the patient on any one day.

129. The method of any one of Embodiments 125-127, wherein no greater than 40 mL of the third injectable pharmaceutical composition is administered to the patient on any one day.

130. The method of any one of Embodiments 125-127, wherein no greater than 20 mL of the third injectable pharmaceutical composition is administered to the patient on any one day.

131. The method of any one of Embodiments 125-127, wherein no greater than 10 mL of the third injectable pharmaceutical composition is administered to the patient on any one day.

132. The method of any one of Embodiments 125-131, wherein no greater than 5 mL of the third injectable pharmaceutical composition is administered to any one location of the patient on any one day.

133. The method of any one of Embodiments 125-131, wherein no greater than 2 mL of the third injectable pharmaceutical composition is administered to any one location of the patient on any one day.

134. The method of any one of Embodiments 125-133, wherein a local anesthetic agent other than a caine analgesic is administered to the patient at the location(s) to receive the third injectable pharmaceutical composition prior to administering the third injectable pharmaceutical composition to the patient.

135. The method of any one of Embodiments 114-134, wherein the pain is chronic pain.

136. The method of any one of Embodiments 114-134, wherein the pain is acute pain.

137. The method of any one of Embodiments 114-134, wherein the pain is neuropathic pain.

138. The method of any one of Embodiments 114-134, wherein the pain is non-neuropathic pain.

139. The method of any one of Embodiments 114-134, wherein the pain is neck pain.

140. The method of any one of Embodiments 114-134, wherein the pain is back pain.

141. The method of any one of Embodiments 114-134, wherein the pain is nociceptive pain, inflammatory pain, or functional pain.

142. The method of any one of Embodiments 114-141, wherein the patient experiences at least a 25% reduction in pain within 6 months after the first day of the treatment method.

143. The method of any one of Embodiments 114-141, wherein the patient experiences at least a 50% reduction in pain within 6 months after the first day of the treatment method.

144. The method of any one of Embodiments 1-143, wherein at least 80% of cells in the aliquot of stromal vascular fraction are viable.

145. The method of any one of Embodiments 1-143, wherein at least 85% of cells in the aliquot of stromal vascular fraction are viable.

146. The method of any one of Embodiments 1-143, wherein at least 90% of cells in the aliquot of stromal vascular fraction are viable.

147. The method of any one of Embodiments 1-143, wherein at least 95% of cells in the aliquot of stromal vascular fraction are viable.

148. The method of any one of Embodiments 1-143, wherein at least 98% of cells in the aliquot of stromal vascular fraction are viable.

149. The method of any one of Embodiments 1-148, wherein the stromal vascular fraction is autologous stromal vascular fraction.

150. The method of any one of Embodiments 1-148, wherein the stromal vascular fraction is derived from adipose tissue obtained from the abdomen of the patient.

151. The method of any one of Embodiments 1-150, wherein the patient is an adult human.

152. The method of any one of Embodiments 1-150, wherein the stromal vascular fraction is derived from adipose tissue through sonication of lipoaspirate according to the following procedure which does not use an enzyme or sonication probe:

a. a container comprising adipose tissue is subjected to sonication, wherein the container is positioned in a sonicator device above a cup horn located in a water bath of the sonicator device, the water bath maintains a constant temperature, and the sonication is performed using pulses of sonication separated by a plurality of rest periods;

b. after sonication in step (a), contents of the container are mixed with saline, and the resulting mixture is subjected to centrifugation;

c. after centrifugation in step (b), a plurality of cell pellets and plurality of buffy coat cell layers are isolated from the oily supernatant, to thereby produce the stromal vascular fraction.

153. The method of Embodiment 152, wherein rest periods in the sonicating procedure are a minimum of 10 seconds each after each one minute of sonication.

154. The method of Embodiment 152 or 153, wherein the total time of sonication is approximately five minutes.

155. The method of any one of Embodiments 152-154, wherein sonication is performed at 70% to 90% amplitude of the sonicator device operating at 20 kHz.

156. The method of any one of Embodiments 152-155, wherein the centrifuging is performed for a duration of at least about three minutes.

157. The method of any one of Embodiments 152-155, wherein the centrifuging is performed for a duration of at least three minutes.

158. The method of any one of Embodiments 152-157, wherein the centrifuging is performed at 3000 rpm.

159. The method of any one of Embodiments 152-158, wherein the plurality of cell pellets and plurality of buffy coat cell layers are subjected to filtration.

160. The method of Embodiment 159, wherein the filtering is performed using a 60 μm filter.

161. The method of any one of Embodiments 152-160, wherein the container is maintained at least 3 mm above the cup horn of the sonicator device.

162. The method of any one of Embodiments 152-161, wherein the water bath is maintained at a temperature of about 200 Celsius.

163. A method for the treatment or prophylaxis of a coronavirus infection in a patient, comprising intravenously administering to said patient in need thereof a stromal vascular fraction according to the following dosing schedule:

a. on the first day, intravenously administer to the patient in need thereof over a duration of about 35 minutes a first injectable pharmaceutical composition containing saline and an aliquot of stromal vascular fraction containing from about 0.7 billion to about 3 billion cells;

b. on the day after the first day, intravenously administer to the patient in need thereof over a duration of about 35 minutes a second injectable pharmaceutical composition containing saline and an aliquot of stromal vascular fraction containing from about 0.3 billion to about 2 billion cells;

c. on the second day after the first day, intravenously administer to the patient in need thereof over a duration of about 35 minutes a third injectable pharmaceutical composition containing saline and an aliquot of stromal vascular fraction containing from about 0.3 billion to about 2 billion cells; and d. on the third day after the first day, intravenously administer to the patient in need thereof over a duration of about 35 minutes a fourth injectable pharmaceutical composition containing saline and an aliquot of stromal vascular fraction containing from about 0.3 billion to about 2 billion cells;

wherein the stromal vascular fraction is derived from adipose tissue through sonication of lipoaspirate and without the use of an enzyme or sonication probe.

164. The method of Embodiment 163, wherein the first injectable pharmaceutical composition contains saline and an aliquot of stromal vascular fraction containing from about 0.9 billion to about 1.5 billion cells.

165. The method of Embodiment 163 or 164, wherein the second injectable pharmaceutical composition contains saline and an aliquot of stromal vascular fraction containing from about 0.4 billion to about 1 billion cells.

166. The method of any one of Embodiments 163-165, wherein the third injectable pharmaceutical composition contains saline and an aliquot of stromal vascular fraction containing from about 0.4 billion to about 1 billion cells.

167. The method of any one of Embodiments 163-166, wherein the fourth injectable pharmaceutical composition contains saline and an aliquot of stromal vascular fraction containing from about 0.4 billion to about 1 billion cells.

168. The method of any one of Embodiments 163-167, wherein the first injectable pharmaceutical composition contains from about 240 mL to about 290 mL saline.

169. The method of any one of Embodiments 163-168, wherein the first injectable pharmaceutical composition has a volume of from about 330 mL to about 350 mL.

170. The method of any one of Embodiments 163-169, wherein the second injectable pharmaceutical composition contains from about 240 mL to about 290 mL saline.

171. The method of any one of Embodiments 163-170, wherein the second injectable pharmaceutical composition has a volume of from about 290 mL to about 310 mL.

172. The method of any one of Embodiments 163-171, wherein the third injectable pharmaceutical composition contains from about 240 mL to about 290 mL saline.

173. The method of any one of Embodiments 163-172, wherein the third injectable pharmaceutical composition has a volume of from about 290 mL to about 310 mL.

174. The method of any one of Embodiments 163-173, wherein the fourth injectable pharmaceutical composition contains from about 240 mL to about 290 mL saline.

175. The method of any one of Embodiments 163-174, wherein the fourth injectable pharmaceutical composition has a volume of from about 290 mL to about 310 mL.

176. The method of any one of Embodiments 163-175, further comprising the step of: prior to intravenously administering the first injectable pharmaceutical composition to the patient on the first day, adipose tissue is obtained from the patient and processed to provide stromal vascular fraction used in the first injectable pharmaceutical composition.

177. The method of any one of Embodiments 163-176, wherein the coronavirus infection is an infection by severe acute respiratory syndrome coronavirus 2 (SARS-CoV-2).

178. The method of any one of Embodiments 163-176, wherein the coronavirus infection is an infection by a variant of SARS-CoV-2.

179. The method of any one of Embodiments 163-176, wherein the coronavirus infection is an infection by a variant of SARS-CoV-2 having the spike protein of SARS-CoV-2.

180. The method of any one of Embodiments 163-176, wherein the coronavirus infection is an infection by SARS-CoV-2 or a variant thereof selected from B.1.617.2, Cluster 5, Lineage B.1.1.207, Lineage B.1.1.7, Variant of Concern 202102/02, Lineage B.1.1.317, Lineage B.1.1.318, Lineage B.1.351, Lineage B.1.429, Lineage B.1.525, Lineage P.1 (also known as Lineage B.1.1.28), D614G, E484K, N501Y, S477G/N, and P681H.

181. The method of any one of Embodiments 163-180, wherein the patient suffers from cognitive impairment (e.g., brain fog) due to the coronavirus infection.

182. The method of any one of Embodiments 163-181, wherein the patient is immuno-compromised.

183. The method of any one of Embodiments 163-182, wherein the method improves immune function to thereby expedite recovery from a coronavirus infection.

184. The method of any one of Embodiments 163-183, wherein the method improves immune function to reduce the risk of contracting a coronavirus infection.

185. The method of any one of Embodiments 163-184, wherein the method enhances repair of patient tissue damaged by a coronavirus infection.

186. The method of any one of Embodiments 163-184, wherein the method enhances repair of patient tissue selected from lung tissue, kidney tissue, and pancreatic tissue damaged by a coronavirus infection.

187. The method of any one of Embodiments 163-184, wherein the method enhances repair of fibrotic tissue or scar tissue resulting from a coronavirus infection.

188. The method of any one of Embodiments 163-187, wherein the method treats the coronavirus infection.

189. The method of any one of Embodiments 163-188, wherein at least 80% of cells in the aliquot of stromal vascular fraction are viable.

190. The method of any one of Embodiments 163-188, wherein at least 85% of cells in the aliquot of stromal vascular fraction are viable.

191. The method of any one of Embodiments 163-188, wherein at least 90% of cells in the aliquot of stromal vascular fraction are viable.

192. The method of any one of Embodiments 163-188, wherein at least 95% of cells in the aliquot of stromal vascular fraction are viable.

193. The method of any one of Embodiments 163-188, wherein at least 98% of cells in the aliquot of stromal vascular fraction are viable.

194. The method of any one of Embodiments 163-193, wherein the stromal vascular fraction is autologous stromal vascular fraction.

195. The method of any one of Embodiments 163-193, wherein the stromal vascular fraction is derived from adipose tissue obtained from the abdomen of the patient.

196. The method of any one of Embodiments 163-195, wherein the patient is an adult human.

197. The method of any one of Embodiments 163-195, wherein the stromal vascular fraction is derived from adipose tissue through sonication of lipoaspirate according to the following procedure which does not use an enzyme or sonication probe:

a. a container comprising adipose tissue is subjected to sonication, wherein the container is positioned in a sonicator device above a cup horn located in a water bath of the sonicator device, the water bath maintains a constant temperature, and the sonication is performed using pulses of sonication separated by a plurality of rest periods;

b. after sonication in step (a), contents of the container are mixed with saline, and the resulting mixture is subjected to centrifugation;

c. after centrifugation in step (b), a plurality of cell pellets and plurality of buffy coat cell layers are isolated from the oily supernatant, to thereby produce the stromal vascular fraction.

198. The method of Embodiment 197, wherein rest periods in the sonicating procedure are a minimum of 10 seconds each after each one minute of sonication.

199. The method of Embodiment 197 or 198, wherein the total time of sonication is approximately five minutes.

200. The method of any one of Embodiments 197-199, wherein sonication is performed at 70% to 90% amplitude of the sonicator device operating at 20 kHz.

201. The method of any one of Embodiments 197-200, wherein the centrifuging is performed for a duration of at least about three minutes.

202. The method of any one of Embodiments 197-200, wherein the centrifuging is performed for a duration of at least three minutes.

203. The method of any one of Embodiments 197-200, wherein the centrifuging is performed at 3000 rpm.

204. The method of any one of Embodiments 197-201, wherein the plurality of cell pellets and plurality of buffy coat cell layers are subjected to filtration.

205. The method of Embodiment 204, wherein the filtering is performed using a 60 μm filter.

206. The method of any one of Embodiments 197-205, wherein the container is maintained at least 3 mm above the cup horn of the sonicator device.

207. The method of any one of Embodiments 197-206, wherein the water bath is maintained at a temperature of about 200 Celsius.

V. Compositions for Medical Use

Stromal vascular fractions and pharmaceutical compositions may be used to treat a medical condition described herein. The use may be according to a method described herein. For example, one aspect of the invention provides a first injectable pharmaceutical composition, a second injectable pharmaceutical composition, a third injectable pharmaceutical composition, and a fourth injectable pharmaceutical composition for use in treating a pulmonary disorder according to the following dosing schedule:

a. on the first day, intravenously administer to the patient in need thereof over a duration of about 35 minutes a first injectable pharmaceutical composition containing saline and an aliquot of stromal vascular fraction containing from about 0.7 billion to about 3 billion cells;

b. on the day after the first day, intravenously administer to the patient in need thereof over a duration of about 35 minutes a second injectable pharmaceutical composition containing saline and an aliquot of stromal vascular fraction containing from about 0.3 billion to about 2 billion cells;

c. on the second day after the first day, intravenously administer to the patient in need thereof over a duration of about 35 minutes a third injectable pharmaceutical composition containing saline and an aliquot of stromal vascular fraction containing from about 0.3 billion to about 2 billion cells; and d. on the third day after the first day, intravenously administer to the patient in need thereof over a duration of about 35 minutes a fourth injectable pharmaceutical composition containing saline and an aliquot of stromal vascular fraction containing from about 0.3 billion to about 2 billion cells;

wherein the stromal vascular fraction is derived from adipose tissue through sonication of lipoaspirate and without the use of an enzyme or sonication probe.

Embodiments described herein in connection with the methods for treatment may be applied in connection with the pharmaceutical composition for use.

VI. Preparation of a Medicament

Stromal vascular fractions and pharmaceutical compositions described herein may be used in the preparation of a medicament to treat a medical condition described herein. For example, one aspect of the invention provides for the use of a first injectable pharmaceutical composition, a second injectable pharmaceutical composition, a third injectable pharmaceutical composition, and a fourth injectable pharmaceutical composition described herein in the preparation of a medicament for treating a pulmonary disorder according to the following dosing schedule:

a. on the first day, intravenously administer to the patient in need thereof over a duration of about 35 minutes a first injectable pharmaceutical composition containing saline and an aliquot of stromal vascular fraction containing from about 0.7 billion to about 3 billion cells;

b. on the day after the first day, intravenously administer to the patient in need thereof over a duration of about 35 minutes a second injectable pharmaceutical composition containing saline and an aliquot of stromal vascular fraction containing from about 0.3 billion to about 2 billion cells;

c. on the second day after the first day, intravenously administer to the patient in need thereof over a duration of about 35 minutes a third injectable pharmaceutical composition containing saline and an aliquot of stromal vascular fraction containing from about 0.3 billion to about 2 billion cells; and d. on the third day after the first day, intravenously administer to the patient in need thereof over a duration of about 35 minutes a fourth injectable pharmaceutical composition containing saline and an aliquot of stromal vascular fraction containing from about 0.3 billion to about 2 billion cells;

wherein the stromal vascular fraction is derived from adipose tissue through sonication of lipoaspirate and without the use of an enzyme or sonication probe.

Embodiments described herein in connection with the methods for treatment may be applied in connection with the pharmaceutical composition for use in the preparation of a medicament.

VII. Medical Kits

Another aspect of the invention provides a medical kit comprising, for example, (i) a composition described herein, and (ii) instructions for treating a medical disorder described herein according to methods described herein. For example, a more specific embodiment of the invention provides a medical kit comprising, for example, (i) a composition described herein, and (ii) instructions for treating a pulmonary disorder according to methods described herein. Another more specific embodiment of the invention provides a medical kit comprising, for example, (i) a composition described herein, and (ii) instructions for treating pain according to methods described herein.

EXAMPLES

The invention now being generally described, will be more readily understood by reference to the following examples, which are included merely for purposes of illustrating certain aspects and embodiments of the present invention, and are not intended to limit the invention.

Example 1—Preparation of Stromal Vascular Fraction

A stromal vascular fraction for administration to patients was prepared according to the general procedures described below.

Part I—Obtain Adipose Tissue from Patient

The patient is subjected to anesthesia or administered one of levofloxacin, diazepam, or oxycodone approximately thirty minutes prior to start of the adipose tissue extraction procedure. The area of the patient to be subjected to adipose tissue extraction was numbed by injection of a 1% (w/w) lidocaine solution containing epinephrine (1:100,000); no more than 4 mL of 1% (w/w) lidocaine solution is administered to the patient.

A tumescent solution was prepared using a 500 mL bag of saline, 25 mL of an aqueous solution containing 1% (w/w) lidocaine, and 0.5 mL of an aqueous solution containing epinephrine (1:10,000). A tulip infiltrator 14 gauge 2.1 mm×15 cm with a 60 mL BD Luer lock syringe was used to administer 120 mL of tumescent solution to the patient. After a period of 10 minutes, extraction of lipoaspirate was started. A Tulip Premium Single-Use Miller SuperLuerlok 2.11 mm OD (1.70 mm ID)×15 cm with 60 mL BD LuerLok Syringe with jonny lock system was used to extract 80 mL to 200 mL lipoaspirate from the patient. Approximately three to five 60 mL BD syringes were used to obtain the lipoaspirate. The syringes were capped and placed straight up and down. The patient's wound(s) was closed using a steri-strip.

located at least 3 mm above the cup horn; the container is not in contact with the cup horn located in the water bath of the sonicator.

b) No probe is used to lyse the cells through sonication. Nothing enters the sonication bottle except the sample itself which is closed during the sonication process. This minimizes the risk contamination from pathogens or cross-contamination with another patient's cells.

3) Sonicate the lipoaspirate for a duration of 5 minutes.
   a) Sonication is performed at 70-90% amplitude while alternating a 1-minute pulse with interjecting 10 second to 1-minute rests, preferably a minimum rest time of 10 seconds.
   b) The sonicator operates at a frequency of 20 kHz.
   c) Lipoaspirate is kept at a constant temperature of 20° C. by circulating water maintained at a constant temperature. Sonication produces heat and the constant-temperature bath dissipates the heat, keeping the sample at 20° C., thereby increasing the vitality of the stem cells in the process, and avoiding heat denaturing. Maintaining the sonication bottle above and not on the cup horn also decreases the transfer of heat.

4) After sonication is complete, pour 25 mL aliquots of contents of the 250 mL container into 50 mL capacity tubes, and then add 25 mL of sterile saline solution to each 50 mL capacity tube, and place a cap on the tubes.

5) Centrifuge the 50 mL capacity tubes for 5 minutes at 3000 rpm.

6) Remove the cap from tubes, and pour out the fatty tissue (i.e., the supernatant oil layer).

7) Gently mix the remaining contents in the 50 mL capacity tubes so the pellet mixes with the rest of the cells. A small amount of saline (e.g., approximately 5 mL) is added to the 50 mL capacity tubes and the contents are then mixed so that the buffy coat cells and cell pellets are well mixed.

8) Contents of the 50 mL capacity tubes are subjected to filtration to produce the stromal vascular fraction.
   a) If the stromal vascular fraction is to be subjected to cryostorage, then dimethylsulfoxide is added to the stromal vascular fraction.

Results of performing the foregoing general procedure on 10 human patients are provided below.

TABLE 1

| Patient No. | Total Cell Count per mL of Stromal Vascular Fraction | Cell Count in 120 mL of Stromal Vascular Fraction | Percent Cell Viability |
|---|---|---|---|
| 1 | 14,200,000 | 1,704,000,000 | 98.30% |
| 2 | 15,700,000 | 1,884,000,000 | 100% |
| 3 | 24,800,000 | 2,976,000,000 | 95% |
| 4 | 14,500,000 | 1,740,000,000 | 100% |
| 5 | 14,200,000 | 1,704,000,000 | 100% |
| 6 | 11,600,000 | 1,392,000,000 | 100% |
| 7 | 10,200,000 | 1,224,000,000 | 100% |
| 8 | 19,200,000 | 2,304,000,000 | 92.9% |
| 9 | 15,600,000 | 1,872,000,000 | 83.3% |
| 10 | 12,200,000 | 1,464,000,000 | 100% |

Part II—Process Adipose Tissue to Obtain Stromal Vascular Fraction

Adipose tissue obtained from the patient in Part I was subjected to the following general procedure to obtain stromal vascular fraction, where all materials used in the procedure were sterilized before use:

1) Fill 250 mL container with up to 150 mL of lipoaspirate obtained from the patient.

2) Place into a sonicator the 250 mL container containing lipoaspirate.
   a) The container is immersed in the sonicator water bath above a cup horn of the sonicator. The container is A Luna Flow Stem from Logos Biosystems was used to determine total cell count and cell viability. When using cells from the adipose stromal vascular fraction (SVF), it is important to know cell concentration and cell viability. The LUNA-STEM™ system used from Logos Biosystems is equipped with dual fluorescence and brightfield optics to distinguish live and dead nucleated cells from non-nucleated cells. Samples are stained with nucleic acid dyes to determine the concentration and viability of mononucleated cells. Non-nucleated cells are distinguished from debris and also counted. A high-resolution image with live cells labeled with green circles and dead cells with red circles can be viewed to confirm data visually.

The harvested cells include immunophenotypes CD31, CD34 and CD45, which are protein markers expressed by various types of cells, involved in tissue formation, immune response and other cellular functions. These cells also appear to co-express CD73, another protein marker, as well as appear to exhibit immunophenotypic characteristics of non-cultured MSC (mesenchymal stem cells). MSC are multipotent stromal cells that can differentiate into a variety of cell types, including osteoblasts (bone cells), chondrocytes (cartilage cells), myocytes (muscle cells) and adipocytes.

Example 2—Preparation of an Injectable Pharmaceutical Composition Containing Stromal Vascular Fraction An injectable pharmaceutical composition containing stromal vascular fraction for administration to patients was prepared according to the procedures described below.

An aliquot of stromal vascular fraction was combined with sterile saline solution. The saline solution was isotonic.

Example 3—Treatment of Chronic Obstructive Pulmonary Disease

A male human subject 69 years old was diagnosed with COPD, having a pulse oximetry level at 84. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 1.3 billion cells of stromal vascular fraction. Percent viability of all cells in the stromal vascular fraction was at least 95%. Saline was added to the stromal vascular fraction, in order to provide sufficient volume of stromal vascular fraction to complete Sessions 1, 2, and 3 of the Protocol for Treatment of COPD (see below).

Within 5 hours after obtaining the lipoaspirate from the patient, the stromal vascular fraction was injected into saline solution for injection, and the resulting mixture was administered to the patient by intravenous injection according to procedures for Session 1 in the Protocol for Treatment of COPD (see below). The patient was evaluated the next day, where it was determined that the patient's pulse oximetry level improved to 96. The patient subsequently completed Sessions 2 and 3 of the Protocol for Treatment of COPD. The patient was evaluated one week after completing Session 3, where it was determined that the patient's respiratory function had improved dramatically compared to the patient's respiratory function prior to Session 1.

Protocol for Treatment of COPD
  a. Session 1 (Day 1): intravenously administer to the patient over a duration of 35 minutes a first injectable pharmaceutical composition prepared by mixing 250 mL of saline and an aliquot of stromal vascular fraction in the range of 80 mL to 100 mL;
  b. Session 2 (Day 2): intravenously administer to the patient over a duration of 35 minutes a second injectable pharmaceutical composition prepared by mixing 250 mL of saline and an aliquot of stromal vascular fraction in the range of 40 mL to 60 mL;

c. Session 3 (Day 3): intravenously administer to the patient over a duration of 35 minutes a second injectable pharmaceutical composition prepared by mixing 250 mL of saline and an aliquot of stromal vascular fraction in the range of 40 mL to 60 mL; and
  d. Session 4 (Day 4): intravenously administer to the patient over a duration of 35 minutes a second injectable pharmaceutical composition prepared by mixing 250 mL of saline and an aliquot of stromal vascular fraction in the range of 40 mL to 60 mL.

Example 4—Treatment of Emphysema

A 71-year-old female patient presented with emphysema. She had difficulty breathing, going up and down stairs, and at times needed portable oxygen to assist her. The patient had a pulse oximetry level of 86. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 2.0 billion cells of stromal vascular fraction. Percent viability of stem cells in the stromal vascular fraction was at least 95%. Saline was added to the stromal vascular fraction, in order to provide sufficient volume of stromal vascular fraction to complete Sessions 1, 2, 3, and 4 of the Protocol for Treatment of Emphysema (see below).

Within 5 hours after obtaining the lipoaspirate from the patient, the stromal vascular fraction was injected into saline solution for injection, and the resulting mixture was administered to the patient by intravenous injection according to procedures for Session 1 in the Protocol for Treatment of Emphysema (see below). The patient was evaluated the next day, where it was determined that the patient's pulse oximetry level improved to 95. The patient subsequently completed Sessions 2, 3, and 4 of the Protocol for Treatment of Emphysema.

The patient was evaluated one week after completing Session 4, where it was determined that the patient was no longer struggling to breath.

Protocol for Treatment of Emphysema
  a. Session 1 (Day 1): intravenously administer to the patient over a duration of 35 minutes a first injectable pharmaceutical composition prepared by mixing 250 mL of saline and an aliquot of stromal vascular fraction in the range of 80 mL to 100 mL;
  b. Session 2 (Day 2): intravenously administer to the patient over a duration of 35 minutes a second injectable pharmaceutical composition prepared by mixing 250 mL of saline and an aliquot of stromal vascular fraction in the range of 40 mL to 60 mL;
  c. Session 3 (Day 3): intravenously administer to the patient over a duration of 35 minutes a second injectable pharmaceutical composition prepared by mixing 250 mL of saline and an aliquot of stromal vascular fraction in the range of 40 mL to 60 mL; and
  d. Session 4 (Day 4): intravenously administer to the patient over a duration of 35 minutes a second injectable pharmaceutical composition prepared by mixing 250 mL of saline and an aliquot of stromal vascular fraction in the range of 40 mL to 60 mL.

Example 5—Treatment of Asthma

A female patient 56 years old presented with chronic asthma and had a history of intubation approximately 3 times per year. The patient uses an inhaler about 5 times per day and does not exercise due to her asthma. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 1.8 billion cells of stromal vascular fraction. Percent viability of stem cells in the stromal vascular fraction was at least 95%. Saline was added to the stromal vascular fraction, in order to provide sufficient volume of stromal vascular fraction to complete Sessions 1, 2, 3, and 4 of the Protocol for Treatment of Asthma (see below).

Within 5 hours after obtaining the lipoaspirate from the patient, the stromal vascular fraction was injected into saline solution for injection, and the resulting mixture was administered to the patient by intravenous injection according to the Protocol for Treatment of Asthma (see below).

After completing all four Sessions, the patient was evaluated, where it was determined that an inhaler was no longer needed on a daily basis. The patient reported using the inhaler only after strenuous activity. The patient reported going to the gym and having lost 15 pounds of weight.

Protocol for Treatment of Asthma a. Session 1 (Day 1): intravenously administer to the patient over a duration of 35 minutes a first injectable pharmaceutical composition prepared by mixing 250 mL of saline and an aliquot of stromal vascular fraction in the range of 80 mL to 100 mL;

b. Session 2 (Day 2): intravenously administer to the patient over a duration of 35 minutes a second injectable pharmaceutical composition prepared by mixing 250 mL of saline and an aliquot of stromal vascular fraction in the range of 40 mL to 60 mL;

c. Session 3 (Day 3): intravenously administer to the patient over a duration of 35 minutes a second injectable pharmaceutical composition prepared by mixing 250 mL of saline and an aliquot of stromal vascular fraction in the range of 40 mL to 60 mL; and d. Session 4 (Day 4): intravenously administer to the patient over a duration of 35 minutes a second injectable pharmaceutical composition prepared by mixing 250 mL of saline and an aliquot of stromal vascular fraction in the range of 40 mL to 60 mL.

Example 6—Treatment of Acute Respiratory Distress Syndrome (ARDS)

A female patient 38 years old was diagnosed with ARDS. She had a pulse oximetry level of 78 and was admitted as an inpatient to the hospital. Later that day, cell therapy was started according to the procedure described below.

Following the process to obtain adipose tissue described in Example 1, approximately 200 mL of lipoaspirate was obtained from the patient. The lipoaspirate was processed according to the procedure to obtain stromal vascular fraction described in Example 1 to produce approximately 200 mL of stromal vascular fraction, which contained approximately 1.9 billion cells of stromal vascular fraction. Percent viability of stem cells in the stromal vascular fraction was at least 95%.

Within 5 hours after obtaining the lipoaspirate from the patient, the stromal vascular fraction was injected into saline solution for injection, and the resulting mixture was administered to the patient by intravenous injection according to procedures for Session 1 of the Protocol for Treatment of ARDS (see below).

The next day the patient was evaluated, where it was determined that the patient's pulse oximetry level improved 94. The patient completed Sessions 2, 3, and 4 of the Protocol for Treatment of ARDS. One week after completing Session 4 the patient was evaluated, where it was determined that the patient's respiratory function improved dramatically compared to the patient's respiratory function prior to starting the Protocol for Treatment of ARDS.

Protocol for Treatment of ARDS a. Session 1 (Day 1): intravenously administer to the patient over a duration of 35 minutes a first injectable pharmaceutical composition prepared by mixing 250 mL of saline and an aliquot of stromal vascular fraction in the range of 80 mL to 100 mL;

b. Session 2 (Day 2): intravenously administer to the patient over a duration of 35 minutes a second injectable pharmaceutical composition prepared by mixing 250 mL of saline and an aliquot of stromal vascular fraction in the range of 40 mL to 60 mL;

c. Session 3 (Day 3): intravenously administer to the patient over a duration of 35 minutes a second injectable pharmaceutical composition prepared by mixing 250 mL of saline and an aliquot of stromal vascular fraction in the range of 40 mL to 60 mL; and d. Session 4 (Day 4): intravenously administer to the patient over a duration of 35 minutes a second injectable pharmaceutical composition prepared by mixing 250 mL of saline and an aliquot of stromal vascular fraction in the range of 40 mL to 60 mL.

Example 7—Treatment of COVID-19

A 72-year-old male patient on oxygen in the hospital was diagnosed with COVID-19 and was having trouble breathing. The patient has a pulse oximetry level of 78, needed 24 hour oxygen, and was admitted to the hospital as an inpatient. Stem cell therapy was performed on the patient as described below.

Following the process to obtain adipose tissue described in Example 1, approximately 200 mL of lipoaspirate was obtained from the patient. The lipoaspirate was processed according to the procedure to obtain stromal vascular fraction described in Example 1 to produce approximately 200 mL of stromal vascular fraction, which contained approximately 1.8 billion cells of stromal vascular fraction. Percent viability of stem cells in the stromal vascular fraction was at least 95%.

Within 5 hours after obtaining the lipoaspirate from the patient, the stromal vascular fraction was injected into saline solution for injection, and the resulting mixture was administered to the patient by intravenous injection according to procedures for Session 1 of the Protocol for Treatment of COVID-19 (see below). The patient subsequently completed Sessions 2, 3, and 4 of the Protocol for Treatment of COVID-19.

Two days after Session 1, the patient was off oxygen, had a pulse oximetry level of 96, and was discharged from the hospital. The patient was evaluated one week after Session 4, where it was determined that the patient's respiratory function was dramatically improved.

Protocol for Treatment of COVID-19 a. Session 1 (Day 1): intravenously administer to the patient over a duration of 35 minutes a first injectable pharmaceutical composition prepared by mixing 250 mL of saline and an aliquot of stromal vascular fraction in the range of 80 mL to 100 mL;

b. Session 2 (Day 2): intravenously administer to the patient over a duration of 35 minutes a second injectable pharmaceutical composition prepared by mixing 250 mL of saline and an aliquot of stromal vascular fraction in the range of 40 mL to 60 mL;

c. Session 3 (Day 3): intravenously administer to the patient over a duration of 35 minutes a second injectable pharmaceutical composition prepared by mixing 250 mL of saline and an aliquot of stromal vascular fraction in the range of 40 mL to 60 mL; and d. Session 4 (Day 4): intravenously administer to the patient over a duration of 35 minutes a second injectable pharmaceutical composition prepared by mixing 250 mL of saline and an aliquot of stromal vascular fraction in the range of 40 mL to 60 mL.

Example 8—Treatment of Multiple Sclerosis

A female human patient 50 years old presented with multiple sclerosis and suffered from loss of bladder control, loss of use of her right foot with foot drag, blurred vision, and loss of use of her hands. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 2.0 billion cells of stromal vascular fraction. Percent viability of stem cells in the stromal vascular fraction was at least 92%.

Within 5 hours after obtaining the lipoaspirate from the patient, the stromal vascular fraction was injected into saline solution for injection, and the resulting mixture was administered to the patient by intravenous injection according to procedures for Session 1 of the Protocol for Treatment of Multiple Sclerosis (see below). The patient subsequently completed Sessions 2, 3, and 4 of the Protocol for Treatment of Multiple Sclerosis.

After Session 3, the patient reported that she was able to walk, use her arms and hands, and most of her functions returned to normal.

Protocol for Treatment of Multiple Sclerosis a. Session 1 (Day 1):
    i. intravenously administer to the patient over a duration of 25 minutes 100 mL of regular saline solution;
    ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
    iii. add the remaining 40% by volume of the stromal vascular fraction obtained from the patient to the remaining first injectable pharmaceutical composition to form a second injectable pharmaceutical composition; and thereafter
    iv. intravenously administer to the patient in need thereof over a duration of about 30 minutes the second injectable pharmaceutical composition;
b. Session 2 (Approximately Day 31):
    i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
    iii. add the remaining 40% by volume of the stromal vascular fraction obtained from the patient to the remaining first injectable pharmaceutical composition to form a second injectable pharmaceutical composition; and thereafter
    iv. intravenously administer to the patient in need thereof over a duration of about 30 minutes the second injectable pharmaceutical composition; and
c. Session 3 (Approximately Day 61):
    i. intravenously administer to the patient over a duration of 25 minutes 100 mL of regular saline solution;
    ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
    iii. add the remaining 40% by volume of the stromal vascular fraction obtained from the patient to the remaining first injectable pharmaceutical composition to form a second injectable pharmaceutical composition; and thereafter
    iv. intravenously administer to the patient in need thereof over a duration of about 30 minutes the second injectable pharmaceutical composition.

Example 9—Treatment of Amyotrophic Lateral Sclerosis (ALS)

A male human patient 71 years presented with ALS, showed gradual loss of weight, showed loss of muscle control, and had a lack of energy. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 1.5 billion cells of stromal vascular fraction. Percent viability of stem cells in the stromal vascular fraction was at least 92%.

Within 5 hours after obtaining the lipoaspirate from the patient, the stromal vascular fraction was injected into saline solution for injection, and the resulting mixture was administered to the patient by intravenous injection according to procedures for Session 1 of the Protocol for Treatment of ALS (see below). The patient subsequently completed Sessions 2, 3, and 4 of the Protocol for Treatment of ALS.

At a patient follow-up visit one week after Session 1, the patient reported that his appetite improved, he is gaining weight, his has increased energy level, and his overall muscle function has improved substantially. After Session 3, the patient reported he could walk much better, had a greater amount of energy, and improved overall use of bodily functions Protocol for Treatment of ALS a. Session 1 (Day 1):
    i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition;

b. Session 2 (Approximately Day 31):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition; and c. Session 3 (Approximately Day 61):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition.

Example 10—Treatment of Dementia

An 81-year-old male human patient presented with dementia featuring short term memory loss. The patient's family said he was getting worse and had difficulty remembering basic things, tasks and appointments. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 4.6 billion cells of stromal vascular fraction. Percent viability of stem cells in the stromal vascular fraction was at least 92%.

Within 5 hours after obtaining the lipoaspirate from the patient, the stromal vascular fraction was injected into saline solution for injection, and the resulting mixture was administered to the patient by intravenous injection according to the procedures for Session 1 of the Protocol for Treatment of Dementia (see below). The patient subsequently completed Sessions 2, 3, and 4 of the Protocol for Treatment of Dementia.

At the patient follow-up visit one week after Session 1, the patient and his family reported that he had improved memory retention and was not having a blank stare at times. After Session 3, the patient reported that he could recall things better and he has improved memory function.

Protocol for Treatment of Dementia a. Session 1 (Day 1):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition;

b. Session 2 (Approximately Day 31):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition; and c. Session 3 (Approximately Day 61):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition.

Example 11—Treatment of Chronic Traumatic Encephalopathy (CTE)

A 28-year-old male, ex-football player complained about CTE due to the multiple concussions, chronic headaches and pain due to sunlight. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 3.1 billion cells of stromal vascular fraction. Percent viability of stem cells in the stromal vascular fraction was at least 92%.

Within 5 hours after obtaining the lipoaspirate from the patient, the stromal vascular fraction was injected into saline solution for injection, and the resulting mixture was administered to the patient by intravenous injection according to the procedures for Session 1 of the Protocol for Treatment of CTE (see below). The patient subsequently completed Sessions 2, 3, and 4 of the Protocol for Treatment of CTE.

One week after completing Session 4, the patient reported reduced incidence of migraine headache, he is not experiencing sensitivity to sunlight, and is he now able to return to normal activity. The patient also reported overall improved quality of life.

Protocol for Treatment of CTE
a. Session 1 (Day 1):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition;
b. Session 2 (Approximately Day 31):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition; and
c. Session 3 (Approximately Day 61):
   i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition.

Example 12—Treatment of Stroke

A male former actor 32 years old suffered from paralysis on his entire left side. The patient was on a liquid diet and could not chew solid food. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 2.7 billion cells of stromal vascular fraction. Percent viability of stem cells in the stromal vascular fraction was at least 92%.

Within 5 hours after obtaining the lipoaspirate from the patient, the stromal vascular fraction was injected into saline solution for injection, and the resulting mixture was administered to the patient by intravenous injection according to the procedures for Session 1 of the Protocol for Treatment of Stroke (see below). The patient subsequently completed Sessions 2, 3, and 4 of the Protocol for Treatment of Stroke.

At the patient follow-up visit one week after Session 1, the patient reported that he was able to move his left hand and have feeling in his legs as well as able to chew food again. After Session 3, the patient was able to walk again using a walker, and eat and chew food, as well as have range of motion and use of his left arm.

Protocol for Treatment of Stroke
a. Session 1 (Day 1):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition;
b. Session 2 (Approximately Day 31):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition; and c. Session 3 (Approximately Day 61):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition.

Example 13—Treatment of Traumatic Brain Injury

A 32-year-old baseball player/coach was admitted to the hospital with a traumatic brain injury after being hit in the head with a 98 MPH fastball. The patient had brain bleed issues, multiple fractures, and facing permanent brain damage. The patient discharged himself from the hospital and was transported to a clinic for immediate stem cell therapy. Stem cell therapy was then performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 1.1 billion cells of stromal vascular fraction. Percent viability of stem cells in the stromal vascular fraction was at least 92%.

Within 5 hours after obtaining the lipoaspirate from the patient, the stromal vascular fraction was injected into saline solution for injection, and the resulting mixture was administered to the patient by intravenous injection according to the procedures for Session 1 of the Protocol for Treatment of Traumatic Brain Injury (see below).

One week after Session 1, the patient reported and shared pictures showing a substantial reduction in swelling, and the patient's headaches and pressure subsided within 2 days post treatment. The patient reported overall improved quality of life and has had no issues since the treatment. Due to the substantial improvement in the patient's condition after Session 1, the patient did not complete any further sessions.

Protocol for Treatment of Traumatic Brain Injury a. Session 1 (Day 1):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition;

b. Session 2 (Approximately Day 31):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition; and c. Session 3 (Approximately Day 61):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition.

Example 14—Treatment of Post-Traumatic Stress Disorder (PTSD)

A 23-year-old male human from the military presented with PTSD and suffered from chronic migraines, lack of sleep, difficulty reading, difficulty comprehending and difficulty remembering. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 1.9 billion cells of stromal vascular fraction. Percent viability of stem cells in the stromal vascular fraction was at least 92%.

Within 5 hours after obtaining the lipoaspirate from the patient, the stromal vascular fraction was injected into saline solution for injection, and the resulting mixture was administered to the patient by intravenous injection according to the procedures for Session 1 of the Protocol for Treatment of PTSD (see below). The patient subsequently completed Sessions 2 and 3 of the Protocol for Treatment of PTSD.

One week after completing Session 3, the patient reported that his migraines have went away, he was able to have a normal sleep pattern, and he was now able to read without pain. The patient reported overall improved quality of life and has had no issues since the treatment.

Protocol for Treatment of PTSD a. Session 1 (Day 1):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition;
b. Session 2 (Approximately Day 31):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition; and
c. Session 3 (Approximately Day 61):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition.

Example 15—Treatment of Diabetes Mellitus

A 54-year old male patient presented with chronic fatigue and was taking 60 units of insulin per day. The patient was taking naps in the middle of the day and was going to sleep by 9:30 PM. Patient complained of low sex drive and lack of energy. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 125 mL of stromal vascular fraction, which contained approximately 1.8 billion cells of stromal vascular fraction. Percent viability of stem cells in the stromal vascular fraction was at least 95%.

Within 3 hours after obtaining the lipoaspirate from the patient, the stromal vascular fraction was injected into saline solution for injection, and the resulting mixture was administered to the patient by intravenous injection according to the procedures for Session 1 of the Protocol for Treatment for Diabetes (see below). The patient subsequently completed Sessions 2, 3, and 4 of the Protocol for Treatment for Diabetes.

One week after Session 1, the patient reported that his insulin daily intake went from 60 units to less than 5 units, he was no longer taking naps, and his energy level was comparable to that when he was 21 years old. He mentioned that his sleep pattern improved, his cognitive ability improved, and his sexual libido improved. The patient reported overall improved quality of life and after 90 days and used only 5 units of insulin per day rather than 60 units per day. The patient also report that he lost 25 pounds of fat as he now had improved energy level to go to the gym.

Protocol for Treatment of Diabetes Mellitus a. Session 1 (Day 1):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition;
b. Session 2 (Approximately Day 15):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition; and c. Session 3 (Approximately Day 36):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition.
d. Session 4 (Approximately Day 66):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition.

Example 16—Treatment of Chronic Pain

A 73-year-old male patient presented with chronic pain in his legs and joints in his legs (e.g., knee joint) as well as plantar fasciitis due to a motor vehicle accident that occurred 18 months prior. The patient indicated on a WOMAC pain scale that his pain was an 8 out of 10 and continued to get worse especially on cold days. Range of motion was limited in his lower half, and the patient was using a cane to move about. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 140 mL of stromal vascular fraction, which contained approximately 2.8 billion cells of stromal vascular fraction. Percent viability of stem cells in the stromal vascular fraction was at least 85%.

Within 3 hours after obtaining the lipoaspirate from the patient, the stromal vascular fraction was injected into saline solution for injection, and the resulting mixture was administered to the patient by intravenous injection according to the procedure for Session 1 of the Protocol for Treatment of Chronic Pain (see below) as well as 4 local injections at sites of pain. The patient subsequently completed Sessions 2 and 3 of the Protocol for Treatment of Chronic Pain.

One week after completing Session 3, the patient reported that he is no longer using a cane to walk, he experiences much less pain (i.e., pain at level of 1 on a WOMAC pain scale), and he was able to get up in the morning with no difficulties and no pain. The patient reported overall improved quality of life and superior range of motion in the knees and ankles. At a patient follow-up visit three months after Session 3, the patient reported that the improvements reported one week after completing Session 3 were maintained and he has experienced an increased level of activity, energy, and sexual libido.

Protocol for Treatment of Chronic Pain
a. Session 1 (Day 1):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition;
b. Session 2 (Approximately Day 91):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition; and
c. Session 3 (Approximately Day 211):
   i. intravenously administer to the patient over a duration of 25 minutes 100 mL of regular saline solution;
   ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
   iii. add the remaining 40% by volume of the stromal vascular fraction obtained from the patient to the remaining first injectable pharmaceutical composition to form a second injectable pharmaceutical composition; and thereafter
   iv. intravenously administer to the patient in need thereof over a duration of about 30 minutes the second injectable pharmaceutical composition.

Example 17—Treatment of Arthritis Pain

A 55-year-old female patient presented with osteoarthritic ankle pain due to a skiing accident 14 months prior. She could not sleep without pain interruptions in the middle of the night, and it was painful to walk. Ankle pain was reported as 7 out of 10 on a WOMAC Pain Scale and the affected ankle had limited range of motion. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 1.6 billion cells of stromal vascular fraction. Percent viability of stem cells in the stromal vascular fraction was at least 95%.

Within 5 hours after obtaining the lipoaspirate from the patient, the stromal vascular fraction was injected into saline solution for injection, and the resulting mixture was administered to the patient by intravenous injection according to the procedure for Session 1 of the Protocol for Treatment of Chronic Pain (see below). The patient subsequently completed Sessions 2 and 3 of the Protocol for Treatment of Chronic Pain.

One week after completing Session 3, the patient reported that her joint pain due to osteoarthritis had subsided to a level of no greater than 2 out of 10, overall quality of life had improved, range of motion in the treated ankle has improved, and she returned to normal sleep patterns. Three months after completing Session 3, the patient reported that her knee joint pain due to osteoarthritis remained at a level of no greater than 2 out of 10.

Protocol for Treatment of Chronic Pain
a. Session 1 (Day 1):
 i. intravenously administer to the patient over a duration of 25 minutes 100 mL of regular saline solution;
 ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
 iii. add the remaining 40% by volume of the stromal vascular fraction obtained from the patient to the remaining first injectable pharmaceutical composition to form a second injectable pharmaceutical composition; and thereafter
 iv. intravenously administer to the patient in need thereof over a duration of about 30 minutes the second injectable pharmaceutical composition;
b. Session 2 (Approximately Day 91):
 i. intravenously administer to the patient over a duration of 25 minutes 100 mL of regular saline solution;
 ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
 iii. add the remaining 40% by volume of the stromal vascular fraction obtained from the patient to the remaining first injectable pharmaceutical composition to form a second injectable pharmaceutical composition; and thereafter
 iv. intravenously administer to the patient in need thereof over a duration of about 30 minutes the second injectable pharmaceutical composition; and
c. Session 3 (Approximately Day 211):
 i. intravenously administer to the patient over a duration of 25 minutes 100 mL of regular saline solution;
 ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
 iii. add the remaining 40% by volume of the stromal vascular fraction obtained from the patient to the remaining first injectable pharmaceutical composition to form a second injectable pharmaceutical composition; and thereafter
 iv. intravenously administer to the patient in need thereof over a duration of about 30 minutes the second injectable pharmaceutical composition.

Example 18—Treatment of Osteoarthritis Pain

A 54-year-old female patient presented with osteoarthritis pain in her knee. Pain was reported to be 6 out of 10 on a WOMAC Pain Scale, and the patient was diagnosed with limited range of motion in the affected knee. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 140 mL of stromal vascular fraction, which contained approximately 2.2 billion cells of stromal vascular fraction. Percent viability of stem cells in the stromal vascular fraction was at least 95%.

Within 5 hours after obtaining the lipoaspirate from the patient, the stromal vascular fraction was injected into saline solution for injection, and the resulting mixture was administered to the patient by intravenous injection according to the procedures for Session 1 of the Protocol for Treatment of Osteoarthritis (see below). The patient subsequently completed Sessions 2 and 3 of the Protocol for Treatment of Osteoarthritis.

One week after completing Session 3, the patient reported that the joint pain due to osteoarthritis had subsided to a level of no greater than 2 out of 10, overall quality of life has improved, and the treated knee now has an increased range of motion. Three months after completing Session 3, the patient reported that her knee joint pain due to osteoarthritis remained at a level of no greater than 2 out of 10.

Protocol for Treatment of Osteoarthritis
a. Session 1 (Day 1):
 i. intravenously administer to the patient over a duration of 25 minutes 100 mL of regular saline solution;
 ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
 iii. add the remaining 40% by volume of the stromal vascular fraction obtained from the patient to the remaining first injectable pharmaceutical composition to form a second injectable pharmaceutical composition; and thereafter
 iv. intravenously administer to the patient in need thereof over a duration of about 30 minutes the second injectable pharmaceutical composition;
b. Session 2 (Approximately Day 91):
 i. intravenously administer to the patient over a duration of 25 minutes 100 mL of regular saline solution;
 ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition; and c. Session 3 (Approximately Day 211):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition.

Example 19—Treatment of Fibromyalgia/Chronic Inflammatory Demyelinating Neuropathy (CIDP)

A male patient 57 years hold was diagnosed with CIDP and was taking 80 grams by intravenous injection (IV) of GAMUNEX®-C (immune globulin injection [human], 10% caprylate/chromatography purified) every two weeks and continued to have difficulty walking, getting out of bed, and being weight-bearing on his own. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 145 mL of stromal vascular fraction, which contained approximately 2.1 billion cells of stromal vascular fraction. Percent viability of stem cells in the stromal vascular fraction was at least 95%.

Within 5 hours after obtaining the lipoaspirate from the patient, the stromal vascular fraction was injected into saline solution for injection, and the resulting mixture was administered to the patient by intravenous injection according to the Protocol for Treatment of Chronic Pain (see below). The patient subsequently completed Sessions 2 and 3 of the Protocol for Treatment of Chronic Pain.

One week after completing Session 3, the patient reported that he is no longer taking GAMUNEX®-C (immune globulin injection [human], 10% caprylate/chromatography purified), was able to ride a bike for the first time in two years, is walking unassisted now, and can now walk up stairs, where that was not possible before. The patient reported overall improved quality of life.

Protocol for Treatment of Chronic Pain a. Session 1 (Day 1):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition;

b. Session 2 (Approximately Day 91):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition; and c. Session 3 (Approximately Day 211):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition.

Example 20—Treatment of Neck Pain

A 58-year-old man presented with chronic neck pain and osteoarthritis of the neck. He complained of pain in the neck, lack of range of motion, and headaches caused from neck pain. Stem cell therapy was performed on the patient as described below.

Following the process to obtain adipose tissue described in Example 1, approximately 125 mL of lipoaspirate was obtained from the patient. The lipoaspirate was processed according to the procedure to obtain stromal vascular fraction described in Example 1 to produce approximately 130 mL of stromal vascular fraction, which contained approximately 1.4 billion cells of stromal vascular fraction. Percent viability of stem cells in the stromal vascular fraction was at least 95%.

Within 5 hours after obtaining the lipoaspirate from the patient, the stromal vascular fraction was injected into saline solution for injection, and the resulting mixture was administered to the patient by intravenous injection according to the procedures for Session of 1 the Protocol for Treatment of Osteoarthritis. The patient subsequently completed Sessions 2 and 3 of the Protocol for Treatment of Osteoarthritis.

One week after completing Session 3, the patient reported that his neck pain had improved dramatically and his pain due to osteoarthritis had subsided to a level of no greater than 2 out of 10. The patient reported overall improved quality of life and superior range of motion in his neck. Three months after completing Session 3, the patient reported that his pain due to osteoarthritis remained at a level of no greater than 2 out of 10, and he still has improved range of motion in the treated area.

Protocol for Treatment of Osteoarthritis a. Session 1 (Day 1):
  i. intravenously administer to the patient over a duration of 25 minutes 100 mL of regular saline solution;
  ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
  iii. add the remaining 40% by volume of the stromal vascular fraction obtained from the patient to the remaining first injectable pharmaceutical composition to form a second injectable pharmaceutical composition; and thereafter
  iv. intravenously administer to the patient in need thereof over a duration of about 30 minutes the second injectable pharmaceutical composition;
b. Session 2 (Approximately Day 91):
  i. intravenously administer to the patient over a duration of 25 minutes 100 mL of regular saline solution;
  ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
  iii. add the remaining 40% by volume of the stromal vascular fraction obtained from the patient to the remaining first injectable pharmaceutical composition to form a second injectable pharmaceutical composition; and thereafter
  iv. intravenously administer to the patient in need thereof over a duration of about 30 minutes the second injectable pharmaceutical composition; and
c. Session 3 (Approximately Day 211):
  i. intravenously administer to the patient over a duration of 25 minutes 100 mL of regular saline solution;
  ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
  iii. add the remaining 40% by volume of the stromal vascular fraction obtained from the patient to the remaining first injectable pharmaceutical composition to form a second injectable pharmaceutical composition; and thereafter
  iv. intravenously administer to the patient in need thereof over a duration of about 30 minutes the second injectable pharmaceutical composition.

Example 21—Treatment of Back Pain

A 41-year-old male presented with chronic back pain and osteoarthritis. He was complaining of pain in the back and a WOMAC pain scale of 7 out of 10. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 2.6 billion cells of stromal vascular fraction. Percent viability of stem cells in the stromal vascular fraction was at least 95%.

Within 5 hours after obtaining the lipoaspirate from the patient, the stromal vascular fraction was injected into saline solution for injection, and the resulting mixture was administered to the patient by intravenous injection according to the procedures for Session 1 of the Protocol for Treatment of Osteoarthritis. The patient subsequently completed Sessions 2 and 3 of the Protocol for Treatment of Osteoarthritis.

One week after completing Session 3, the patient reported that his back pain had improved dramatically and his pain due to osteoarthritis had subsided to a level of no greater than 2 out of 10. The patient reported overall improved quality of life and superior range of motion in his lower back and was able to resume golf again. Three months after completing Session 3, the patient reported that his pain due to osteoarthritis remained at a level of no greater than 2 out of 10, and he still had improved range of motion in the treated area and continued to play golf on a weekly basis with no effects of pain.

Protocol for Treatment of Osteoarthritis a. Session 1 (Day 1):
  i. intravenously administer to the patient over a duration of 25 minutes 100 mL of regular saline solution;
  ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
  iii. add the remaining 40% by volume of the stromal vascular fraction obtained from the patient to the remaining first injectable pharmaceutical composition to form a second injectable pharmaceutical composition; and thereafter
  iv. intravenously administer to the patient in need thereof over a duration of about 30 minutes the second injectable pharmaceutical composition;
b. Session 2 (Approximately Day 91):
  i. intravenously administer to the patient over a duration of 25 minutes 100 mL of regular saline solution;
  ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition; and c. Session 3 (Approximately Day 211):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition.

Example 22—Treatment of Exemplary Pulmonary Indications

Human patients presenting with a pulmonary indication selected from edema, bronchitis, chronic bronchitis, or pneumonia were treated with the stem cell therapy described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 1.3 billion cells of stromal vascular fraction. Percent viability of all cells in the stromal vascular fraction was at least 95%. Saline was added to the stromal vascular fraction, in order to provide sufficient volume of stromal vascular fraction to complete Sessions 1, 2, and 3 of the Protocol for Treatment (see below).

Within 5 hours after obtaining the lipoaspirate from the patient, the stromal vascular fraction was injected into saline solution for injection, and the resulting mixture was administered to the patient by intravenous injection according to procedures for Session 1 in the Protocol for Treatment (see below). Sessions 2-4 were completed according to the Protocol for Treatment (see below)

Patients were observed for improvement in the pulmonary indication—improvement was observed in the form of reduced inflammation of pulmonary tissue and/or increase in pulse oxygen rate from mid-to-high 70's to the low-to-mid 90's.

Protocol for Treatment a. Session 1 (Day 1): intravenously administer to the patient over a duration of 35 minutes a first injectable pharmaceutical composition prepared by mixing 250 mL of saline and an aliquot of stromal vascular fraction in the range of 80 mL to 100 mL;

b. Session 2 (Day 2): intravenously administer to the patient over a duration of 35 minutes a second injectable pharmaceutical composition prepared by mixing 250 mL of saline and an aliquot of stromal vascular fraction in the range of 40 mL to 60 mL;

c. Session 3 (Day 3): intravenously administer to the patient over a duration of 35 minutes a second injectable pharmaceutical composition prepared by mixing 250 mL of saline and an aliquot of stromal vascular fraction in the range of 40 mL to 60 mL; and d. Session 4 (Day 4): intravenously administer to the patient over a duration of 35 minutes a second injectable pharmaceutical composition prepared by mixing 250 mL of saline and an aliquot of stromal vascular fraction in the range of 40 mL to 60 mL.

Example 23—Treatment of Post-Concussion Syndrome

A human patient presenting with post-concussion syndrome was treated with stem cell therapy as described below. Prior to receiving stem cell therapy, the patient presented with ringing in the ears, headache, and pain.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 1.1 billion cells of stromal vascular fraction. Percent viability of stem cells in the stromal vascular fraction was at least 92%.

Within 5 hours after obtaining the lipoaspirate from the patient, the stromal vascular fraction was injected into saline solution for injection, and the resulting mixture was administered to the patient by intravenous injection for Session 1 according to the Protocol for Treatment (see below). Sessions 2-3 were completed according to the Protocol for Treatment (see below).

Following receiving stem cell therapy, there was a substantial reduction in swelling, and reduction in the symptoms of concussion, including a reduction in ringing sensation in the ears, reduction in headache, and reduction in pain.

Protocol for Treatment a. Session 1 (Day 1):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition;

b. Session 2 (Approximately Day 31):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition; and c. Session 3 (Approximately Day 61):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition.

Example 24—Treatment of Neuropathy

A human patient presented with neuropathy. The patient was unable to walk, unable to feel their toes, and was unstable when standing without a walker or assistance. The patient was taking 80 grams of gammunex to help manage their symptoms. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 120 mL of stromal vascular fraction, which contained approximately 4.6 billion cells of stromal vascular fraction. Percent viability of stem cells in the stromal vascular fraction was at least 92%.

Within 5 hours after obtaining the lipoaspirate from the patient, the stromal vascular fraction was injected into saline solution for injection, and the resulting mixture was administered to the patient by intravenous injection according to the Protocol for Treatment (see below).

After receiving stem cell therapy, the patient was able to feel their toes, was able to walk, run, and ride a bicycle without assistance.

Protocol for Treatment a. Session 1 (Day 1):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition;

b. Session 2 (Approximately Day 31):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition; and c. Session 3 (Approximately Day 61):

i. intravenously administer to the patient over a duration of 25 minutes 100 mL of regular saline solution;

ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter iii. add the remaining 40% by volume of the stromal vascular fraction obtained from the patient to the remaining first injectable pharmaceutical composition to form a second injectable pharmaceutical composition; and thereafter iv. intravenously administer to the patient in need thereof over a duration of about 30 minutes the second injectable pharmaceutical composition, and thereafter v. the patient will need to continue this form of cell therapy every 12-15 months.

Example 25—Treatment of Functional Pain

A human patient presented with pain while walking and had been diagnosed as needing joint replacement to address the pain while walking. Stem cell therapy was performed on the patient as described below.

Following the process to obtain adipose tissue described in Example 1, approximately 120 mL of lipoaspirate was obtained from the patient. The lipoaspirate was processed according to the procedure to obtain stromal vascular fraction described in Example 1 to produce approximately 140 mL of stromal vascular fraction, which contained approximately 2.8 billion cells of stromal vascular fraction. Percent viability of stem cells in the stromal vascular fraction was at least 85%.

Within 3 hours after obtaining the lipoaspirate from the patient, the stromal vascular fraction was injected into saline solution for injection, and the resulting mixture was administered to the patient by intravenous injection according to the procedure for Session 1 of the Protocol for Treatment (see below). The patient subsequently completed Sessions 2 and 3 of the Protocol for Treatment.

After receiving stem cell therapy, the patient was able to walk without experiencing pain.

Protocol for Treatment a. Session 1 (Day 1):
    i. intravenously administer to the patient over a duration of 25 minutes 100 mL of regular saline solution;
    ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
    iii. add the remaining 40% by volume of the stromal vascular fraction obtained from the patient to the remaining first injectable pharmaceutical composition to form a second injectable pharmaceutical composition; and thereafter
    iv. intravenously administer to the patient in need thereof over a duration of about 30 minutes the second injectable pharmaceutical composition;

b. Session 2 (Approximately Day 91):
    i. intravenously administer to the patient over a duration of 25 minutes 100 mL of regular saline solution;
    ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
    iii. add the remaining 40% by volume of the stromal vascular fraction obtained from the patient to the remaining first injectable pharmaceutical composition to form a second injectable pharmaceutical composition; and thereafter
    iv. intravenously administer to the patient in need thereof over a duration of about 30 minutes the second injectable pharmaceutical composition; and c. Session 3 (Approximately Day 211):
    i. intravenously administer to the patient over a duration of 25 minutes 100 mL of regular saline solution;
    ii. intravenously administer to the patient over a duration of 45 minutes a 200 mL aliquot of a first injectable pharmaceutical composition prepared by mixing 400 mL of saline and 60% by volume of the stromal vascular fraction obtained from the patient; and thereafter
    iii. add the remaining 40% by volume of the stromal vascular fraction obtained from the patient to the remaining first injectable pharmaceutical composition to form a second injectable pharmaceutical composition; and thereafter
    iv. intravenously administer to the patient in need thereof over a duration of about 30 minutes the second injectable pharmaceutical composition.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of treating a pulmonary disorder, consisting of intravenously administering to a human patient in need thereof a stromal vascular fraction according to the following dosing schedule, in order to treat the pulmonary disorder:
    (a) on the first day, intravenously administer to the patient in need thereof over a duration of about 35 minutes a first injectable pharmaceutical composition consisting of saline and an aliquot of stromal vascular fraction containing from about 0.7 billion to about 3 billion cells;
    (b) on the day after the first day, intravenously administer to the patient in need thereof over a duration of about 35 minutes a second injectable pharmaceutical composition consisting of saline and an aliquot of stromal vascular fraction containing from about 0.3 billion to about 2 billion cells;
    (c) on the second day after the first day, intravenously administer to the patient in need thereof over a duration of about 35 minutes a third injectable pharmaceutical composition consisting of saline and an aliquot of stromal vascular fraction containing from about 0.3 billion to about 2 billion cells; and
    (d) on the third day after the first day, intravenously administer to the patient in need thereof over a duration of about 35 minutes a fourth injectable pharmaceutical composition consisting of saline and an aliquot of stromal vascular fraction containing from about 0.3 billion to about 2 billion cells;
    wherein the stromal vascular fraction is autologous stromal vascular fraction derived from adipose tissue through sonication of lipoaspirate and without the use of an enzyme or sonication probe; and
    wherein the patient has not received intravenously administered saline immediately prior to the start of said dosing scheduling for administering said stromal vascular fraction.

2. The method of claim 1, wherein the first injectable pharmaceutical composition consists of saline and an aliquot of autologous stromal vascular fraction containing from about 0.9 billion to about 1.5 billion cells.

3. The method of claim 2, wherein the second injectable pharmaceutical composition consists of saline and an aliquot of autologous stromal vascular fraction containing from about 0.4 billion to about 1 billion cells.

4. The method of claim 3, wherein the third injectable pharmaceutical composition consists of saline and an aliquot of autologous stromal vascular fraction containing from about 0.4 billion to about 1 billion cells.

5. The method of claim 4, wherein the fourth injectable pharmaceutical composition consists of saline and an aliquot of autologous stromal vascular fraction containing from about 0.4 billion to about 1 billion cells.

6. The method of claim 5, wherein at least 25% of cells in the stromal vascular fraction are mesenchymal stem cells.

7. The method of claim 1, wherein there is from about 240 mL to about 290 mL of saline in the first injectable pharmaceutical composition.

8. The method of claim 7, wherein there is from about 240 mL to about 290 mL of saline in the second injectable pharmaceutical composition.

9. The method of claim 8, wherein there is from about 240 mL to about 290 mL of saline in the third injectable pharmaceutical composition.

10. The method of claim 1, wherein the first injectable pharmaceutical composition has a volume of from about 330 mL to about 350 mL.

11. The method of claim 10, wherein the second injectable pharmaceutical composition has a volume of from about 290 mL to about 310 mL.

12. The method of claim 11, wherein the third injectable pharmaceutical composition has a volume of from about 290 mL to about 310 mL.

13. The method of claim 1, wherein the pulmonary disorder is chronic obstructive pulmonary disease.

14. The method of claim 1, wherein the pulmonary disorder is asthma.

15. The method of claim 1, wherein the pulmonary disorder is bronchitis.

16. The method of claim 1, wherein the pulmonary disorder is chronic bronchitis.

17. The method of claim 1, wherein the pulmonary disorder is emphysema.

18. The method of claim 1, wherein the pulmonary disorder is acute respiratory distress syndrome.

19. The method of claim 1, wherein the pulmonary disorder is an infection by a coronavirus.

20. The method of claim 1, wherein the pulmonary disorder is an infection by severe acute respiratory syndrome coronavirus 2 (SARS-COV-2).

21. The method of claim 1, wherein the pulmonary disorder is pneumonia or pleural effusion.

22. The method of claim 1, wherein the patient experiences at least a 25% reduction in a symptom from the pulmonary disorder within 1 week after the first day of the treatment method.

23. The method of claim 1, wherein the patient experiences at least a 50% reduction in a symptom from the pulmonary disorder within 1 week after the first day of the treatment method.

24. The method of claim 1, wherein at least 80% of cells in the aliquot of stromal vascular fraction are viable.

25. The method of claim 1, wherein at least 95% of cells in the aliquot of stromal vascular fraction are viable.

26. The method of claim 25, wherein from about 30% to about 40% of cells in the stromal vascular fraction are mesenchymal stem cells.

27. The method of claim 25, wherein at least 25% of cells in the stromal vascular fraction are mesenchymal stem cells.

28. The method of claim 1, wherein the stromal vascular fraction is derived from adipose tissue obtained from the abdomen of the patient.

29. The method of claim 1, wherein the stromal vascular fraction comprises cells having immunophenotype CD31, CD34, and CD45.

30. The method of claim 1, wherein the stromal vascular fraction comprises cells having immunophenotype CD31, CD34, CD45, and CD73.

31. The method of claim 1, wherein at least 25% of cells in the stromal vascular fraction are mesenchymal stem cells.

32. The method of claim 1, wherein the patient is an adult human.

33. The method of claim 1, wherein from about 30% to about 40% of cells in the stromal vascular fraction are mesenchymal stem cells.

34. A method of treating a pulmonary disorder, consisting of intravenously administering to a human patient in need thereof a stromal vascular fraction according to the following dosing schedule, in order to treat the pulmonary disorder:

(a) on the first day, intravenously administer to the patient in need thereof over a duration of about 35 minutes a first injectable pharmaceutical composition consisting of saline and an aliquot of stromal vascular fraction containing from about 0.7 billion to about 3 billion cells;

(b) on the day after the first day, intravenously administer to the patient in need thereof over a duration of about 35 minutes a second injectable pharmaceutical composition consisting of saline and an aliquot of stromal vascular fraction containing from about 0.3 billion to about 2 billion cells;

(c) on the second day after the first day, intravenously administer to the patient in need thereof over a duration of about 35 minutes a third injectable pharmaceutical composition consisting of saline and an aliquot of stromal vascular fraction containing from about 0.3 billion to about 2 billion cells; and (d) on the third day after the first day, intravenously administer to the patient in need thereof over a duration of about 35 minutes a fourth injectable pharmaceutical composition consisting of saline and an aliquot of stromal vascular fraction containing from about 0.3 billion to about 2 billion cells;

wherein prior to intravenously administering the first injectable pharmaceutical composition to the patient on the first day, adipose tissue is obtained from the patient and processed to provide autologous stromal vascular fraction used in the first injectable pharmaceutical composition, wherein the autologous stromal vascular fraction cells have not been stored at a temperature below 0° C.;

wherein the stromal vascular fraction is autologous stromal vascular fraction derived from adipose tissue through sonication of lipoaspirate and without the use of an enzyme or sonication probe; and wherein the patient has not received intravenously administered saline immediately prior to the start of said dosing schedule for administering said stromal vascular fraction.

* * * * *